United States Patent
Walensky et al.

(10) Patent No.: US 12,366,576 B2
(45) Date of Patent: Jul. 22, 2025

(54) COMPOSITIONS, ASSAYS, AND METHODS FOR DIRECT MODULATION OF FATTY ACID METABOLISM

(71) Applicant: Dana-Farber Cancer Institute, Inc., Boston, MA (US)

(72) Inventors: Loren D. Walensky, Newton, MA (US); Silvia Escudero, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 143 days.

(21) Appl. No.: 18/059,746

(22) Filed: Nov. 29, 2022

(65) Prior Publication Data
US 2023/0228759 A1    Jul. 20, 2023

Related U.S. Application Data

(62) Division of application No. 16/307,599, filed as application No. PCT/US2017/040360 on Jun. 30, 2017, now Pat. No. 11,567,082.

(60) Provisional application No. 62/357,866, filed on Jul. 1, 2016.

(51) Int. Cl.
| A61P 35/02 | (2006.01) |
| A61K 38/17 | (2006.01) |
| G01N 33/574 | (2006.01) |

(52) U.S. Cl.
CPC ... *G01N 33/57484* (2013.01); *A61K 38/1761* (2013.01); *A61P 35/02* (2018.01); *C12Y 103/08009* (2015.07); *G01N 2333/90206* (2013.01); *G01N 2500/02* (2013.01)

(58) Field of Classification Search
None
See application file for complete search history.

(56) References Cited

U.S. PATENT DOCUMENTS

| 5,128,326 | A | 7/1992 | Balazs et al. |
| 5,679,377 | A | 10/1997 | Bernstein et al. |
| 5,912,015 | A | 6/1999 | Bernstein et al. |
| 5,916,597 | A | 6/1999 | Lee et al. |
| 5,989,463 | A | 11/1999 | Tracy et al. |
| 9,079,970 | B2 | 7/2015 | Walensky et al. |
| 11,567,082 | B2 | 1/2023 | Walensky et al. |
| 2005/0250680 | A1 | 11/2005 | Walensky et al. |
| 2010/0286057 | A1 | 11/2010 | Walensky et al. |
| 2012/0172285 | A1 | 7/2012 | Walensky et al. |
| 2015/0045310 | A1 | 2/2015 | Link et al. |
| 2015/0246955 | A1 | 9/2015 | Walensky et al. |
| 2020/0408767 | A1 | 12/2020 | Walensky et al. |

FOREIGN PATENT DOCUMENTS

| EP | 1331227 A1 | 7/2003 |
| WO | WO 1999/15154 | 4/1999 |
| WO | WO 1999/20253 | 4/1999 |
| WO | WO 2006/034454 | 3/2006 |
| WO | WO 2008/121767 | 10/2008 |
| WO | WO 2010/060112 | 5/2010 |
| WO | WO 2010/068684 | 6/2010 |
| WO | WO 2016/054746 | 4/2016 |

OTHER PUBLICATIONS

Kauer et al. (J. Biol. Chem. Aug. 15, 1986 261(23): 10695-10700) (Year: 1986).*
Coleman et al. (Research in Immunology, 1994; 145(1): 33-36) (Year: 1994).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Escudero, "Direct Regulation of Mitochondrial Fatty Acid Oxidation by Anti-Apoptotic MCL-1," Dissertation for the Degree of Doctor of Philosophy, Harvard University, Apr. 2017, 174 pages.
U.S. Appl. No. 60/995,545, filed Sep. 26, 2007, Walensky et al.
Broadway et al., "Novel Methylenecyclopropyl-based acyl-CoA Dehydrogenase Inhibitor," FEBS Letters, 1998, 437:122-126.
Amundadittir et al., "Transgenic Mouse Models of Breast Cancer," Breast Cancer Res Treat., 1996, 39(1):119-135.
Appelbaum, "Graft versus leukemia (GVL) in the therapy of acute lymphoblastic leukemia (ALL)," *Leukemia*, 1997, 11(Suppl. 4):S15-S17.
Belmar et al., "Small molecule Mcl-1 inhibitors for the treatment of cancer," Pharmacology and Therapeutics., Jan. 2015, 145(1):76-84.
Beroukhim et al., "The landscape of somatic copy-number alteration across human cancers," Nature, 2010, 463(7283);899-905.
Billard, "BH3 mimetics: status of the field and new developments," *Mol Cancer Ther.*, 2013, 12(9):1691-700.
Bird et al., "Biophysical determinants for cellular uptake of hydrocarbon-stapled peptide helices," Nat Chem Biol., 2016, 12(10):845-52.
Bird, "Chemical synthesis of hydrocarbon-stapled peptides for protein interaction research and therapeutic targeting," Curr Protoc Chem Biol., 2011, 1;3(3):99-117.
Bird, "Synthesis and biophysical characterization of stabilized alpha-helices of BCL-2 domains," Meth Enzymol., 2008, 446:369-86.
Blackwell et al., "Highly Efficient Synthesis of Covalently Cross-Linked Peptide Helices by Ring-Closing Metathesis," Chem Int Ed., 1998 37:3281-3284.

(Continued)

*Primary Examiner* — Peter J Reddig
(74) *Attorney, Agent, or Firm* — Fish & Richardson P.C.

(57) ABSTRACT

This disclosure relates to the surprising and unexpected finding that the well-known cancer protein, Myeloid Cell Leukemia-1 (MCL-1), binds to and modulates the enzymatic activity of Very Long Chain Acyl CoA Dehydrogenase (VLCAD), thereby regulating fatty acid β-oxidation. This finding is employed in compositions and methods of treating cancer, metabolic diseases, or other conditions characterized by excessive fatty acid β-oxidation by blocking or reducing the energy production of cells (e.g., cancer) through inhibiting the MCL-1/VLCAD interaction and/or directly inhibiting VLCAD enzymatic activity. In addition, the disclosure features methods for identifying such agents that inhibit the interaction between MCL-1 and VLCAD or that inhibit VLCAD enzymatic activity.

28 Claims, 40 Drawing Sheets

Specification includes a Sequence Listing.

(56) References Cited

OTHER PUBLICATIONS

Blackwell et al., "Ring-closing metathesis of olefinic peptides: design, synthesis, and structural characterization of macrocyclic helical peptides," J Org Chem., 2001, 66(16):5291-5302.
Braun, "Photoreactive stapled BH3 peptides to dissect the BCL-2 family interactome," Chem Biol., 2010, 22;17(12):1325-33.
Brunel et al., "Synthesis of constrained helical peptides by thioether ligation: application to analogs of gp41," Chem. Commun., 2005, (20):2552-2554.
Buchwald et al., "Long-term, continuous intravenous heparin administration by an implantable infusion pump in ambulatory patients with recurrent venous thrombosis," Surgery, 1980, 88(4):507-516.
Chapter 317, "Principals of Neoplasia," in Harrison's: Principals of Internal Medicine, 13th Edition, Isselbacher et al., eds., McGraw-Hill, New York, p. 1814-1826.
Dankort et al., "Transgenic models of breast cancer metastasis," Cancer Treat Res., 1996, 83:71-88.
Derenne et al., "Antisense strategy shows that Mcl-1 rather than Bcl-2 or Bcl-x(L) is an essential survival protein of human myeloma cells," *Blood*, 2002, 100:194-199.
Ding et al., "Myeloid Cell leukemia-1 Inversely Correlates With Glycogen Synthase kinase-3beta Activity and Associates With Poor Prognosis in Human Breast Cancer," *Cancer Research*, 2007, 67(10):4564-71.
Donehower, "The p53-deficient mouse: a model for basic and applied cancer studies," Semin Cancer Biol., 1996, 7(5):269-278.
Doulias et al., "Nitric oxide regulates mitochondrial fatty acid metabolism through reversible protein S-nitrosylat," Sci Signal, 2013, 6(256).
During et al., "Controlled release of dopamine from a polymeric brain implant: in vivo characterization," Ann Neurol., 1989, 25(4):351-6.
EP Extended Search Report in European Appln. No. 17821388.0, dated Jan. 7, 2020, 11 pages.
Escudero et al., "Direct Regulation of Mitochondrial Fatty Acid Oxidation by MCL-1," Poster, Presented at Gordon Conference on Cell Death, Girona, Spain, Jul. 3-8, 2016, 1 page.
Escudero et al., "Dynamic Regulation of Long-Chain Fatty Acid Oxidation by a Noncanonical Interaction between the MCL-1 BH3 Helix and VLCAD," Molecular Cell, Mar. 2018, 69(5):729-743.
Frey, "Study of Immune Response to Tumors in the Rat," Methods, 1997, 12(2): 173-188.
Goodson, "Medical Applications of Controlled Release," Dental Applications, 1984, 2:115-138.
Gutman et al. "Biology of human colon cancer metastasis, " World J Surg., 1995, 19(2):226-234.
Haney et al., "Promoting peptide α-helix formation with dynamic covalent oxime side-chain cross-links," Chem. Commun., 2011, 47(39):10915-10917.
Howard et al., "Intracerebral drug delivery in rats with lesion-induced memory deficits," JNS Neurosurgry., 1989, 71(1)105-12.
Jackson et al., "General Approach to the Synthesis of Short a-Helical Peptides," Am Chem. Soc., 1991, 113:9391-9392.
Jarrett et al., "Model of human transitional cell carcinoma: tumor xenografts in upper urinary tract of nude rat," J Endourol., 1995, 9(1):1-7.
Kawamoto et al., "Design of Triazole-Stapled BCL9 α-Helical Peptides to Target the β-Catenin/B-Cell CLL/lymphoma 9 (BCL9) Protein-Protein Interaction," J Med Chem., 2012, 55:1137.
Kim et al., "Synthesis of all-hydrocarbon stapled α-helical peptides by ring-closing olefin metathesis," Nature protocols, Jun. 2011, 6(6):761-71.
Konopleva et al., "Mechanisms of apoptosis sensitivity and resistance to the BH3 mimetic ABT-737 in acute myeloid leukemia," *Cancer Cell*, 2006, 10(5):375-88.
Kurnita et al., "Photo-control of helix content in a short peptide," Proc. Natl. Acad. Sci., 2000, 97(8):3803-3808.
Langer et al., "Chemical and Physical Structure of Polymers as Carriers for Controlled Release of Bioactive Agents: A review," Journal of Macromolecular Science, 1983, 23(1):61-126.
Langer, "New methods of drug delivery," Science, 1990, 249(4976): 1527-1533.
Lau et al., "Functionalised staple linkages for modulating the cellular activity of stapled peptides," Chem. Sci., 2014, 5:1804-1809.
Lehman et al., "An acyl-coenzyme A dehydrogenase assay utilizing the ferricenium ion," Anal. Biochem., 1990, 186(2):280-284.
Leshchiner et al., "Direct inhibition of oncogenic KRAS by hydrocarbon-stapled SOS1 helices," Proc Natl Acad Sci USA, 2015, 10;112(6):1761-6.
Levy et al., "Inhibition of calcification of bioprosthetic heart valves by local controlled-release diphosphonate," Science, 1985, 228(4696):190-2.
Lovejoy et al., "Animal models and the molecular pathology of cancer," J Pathol., 1997, 181(2):130-135.
Madden et al., "Synthesis of cell-permeable stapled peptide dual inhibitors of the p53-Mdm2/Mdmx interactions via photoinduced cycloaddition," Bioorg. Med. Chem. Lett., 2011, 21(5):1472-1475.
Malone et al., "Mcl-1 Regulates the Survival of Adult Neural Precursor Cells," Mol Cell Neurosci., 2012, 49(4):439-47.
Mcandrew et al., "Structural Basis for Substrate Fatty Acyl Chain Specificity Crystal Structure of Human Very-Long-Chain ACY L-CoA Dehyd Rogenase," The Journal of Biological Chemistry, 2008, 283(14):9435-9443.
Oberstein et al., "Crystal structure of the Bcl-XL-Beclin 1 peptide complex: Beclin 1 is a novel BH3-only protein," J Biol Chem., 2007, 282(17):13123-32.
Opferman et al., "Development and Maintenance of B and T Lymphocytes Requires Antiapoptotic MCL-1," Nature, 2003, 426(6967):671-676.
Opferman et al., "Obligate Role of Anti-Apoptotic MCL-1 in the Survival of Hematopoietic Stem Cells," Science, 2005, 307(5712):1101-4.
Oyasu, "Epithelial tumours of the lower urinary tract in humans and rodents," Food Chem Toxicol., 1995, 33(9):747-755.
PCT International Preliminary Report and Patentability in International Appln. No. PCT/US2017/040360, dated Jan. 1, 2019, 11 pages.
PCT International Search Report and Written Opinion in International Appln. No. PCT/US2017/040360, dated Dec. 14, 2017, 6 pages.
Perciavalle et al., "Anti-apoptotic MCL-1 localizes to the mitochondrial matrix and couples mitochondrial fusion to respiration," Nat Cell Biol., 2012, 14(6):575-83.
Phelan et al., "A General Method for Constraining Short Peptides to an α-Helical Conformation," J Am. Chem. Soc., 1997, 119(3):455-460.
Pitter et al., "Dissection of the BCL-2 family signaling network with stabilized alpha-helices of BCL-2 domains," Meth Enzymol., 2008, 446:387-408.
Polakis, "The adenomatous polyposis coli (APC) tumor suppressor," Biochim Biophys Acta, 1997, 1332(3):F127-F147.
Rinkenberger et al., "Mcl-1 Deficiency Results in Peri-implanation Embryonic Lethality," Genes Dev., 2000, 14(1):23-27.
Royal et al., "Preclinical models of prostate cancer," Semin Oncol., 1996, 23(14):35-40.
Russo et al., "Experimentally induced mammary tumors in rats," Breast Cancer Res Treat., 1996, 39(1):7-20.
Saudek et al., "A preliminary trial of the programmable implantable medication system for insulin delivery," N Engl J Med., 1989, 31;321(9): 574-9.
Sefton, "Implantable Pumps," *CRC Crit Ref Biomed Eng.*, 1987, 14(3):201-240.
Shepherd et al., "Single Turn Peptide Alpha Helices with Exceptional Stability in Water," J Am. Chem. Soc., 2005, 127:2974-2983.
Shoemaker et al., "Studies of neoplasia in the Min mouse," Biochim Biophys Acta, 1997, 1332(2):F25-F48.
Spokoyny et al., A perfluoroaryl-cysteine S(N)Ar chemistry approach to unprotected peptide stapling, J Am. Chem. Soc., 2013, 135(16):5946-5949.

(56) References Cited

OTHER PUBLICATIONS

Stewart et al., "The MCL-1 BH3 helix is an exclusive MCL-1 inhibitor and apoptosis sensitizer," Nat Chem Biol., 2010, 6(8):595-601.
Tanaka et al., "Molecular basis of isovaleric acidemia and medium-chain acyl-CoA dehydrogenase deficiency," Enzyme, 1987, 38(1-4):91-107.
Tarran et al., "Normal and Cystic Fibrosis Airway Surface Liquid Homeostasis, The Effects of Phasic Shear Stress and Viral Infections," *Journal of Biological Chemistry*, 2005, 280(42):3571-35759.
Tcheng et al., "Inhibiting very long chain Acyl-CoA dehydrogenase (VLCAD) induces selective leukemia cell death," Blood, Nov. 13, 2019, 134(Suppl.1), p. 3922.
Thorpe et al., "Structure and mechanism of action of the acyl-CoA dehydrogenases," FASEB J, 1995, 9(9):718-25.
Walensky et al., "A stapled Bid BH3 helix directly binds and activates BAX," Mol Cell, 2006, 24(2):199-210.
Walensky et al., "BAX unleashed: the biochemical transformation of an inactive cytosolic monomer into a toxic mitochondrial pore," Trends in Bio Chem. Sci., 2011, 36(12):642-52.
Wang et al., "Establishment of an experimental intrapulmonary tumor nodule model," Ann Thorac Surg., 1997, 64(1):216-219.
Wang et al., "H3.3 Actively Marks Enhancers and Primes Gene Transcription Via Opening Higher-Ordered Chromatin," Genes Dev., 2013, 27(19):2109-2124.
Warren, "Cytokines in the cotton top tamarin model of human ulcerative colitis," Aliment Pharmacol Ther., 1996, 10(Supp 2):45-47.
Winter et al., "Drug Development. Phthalimide conjugation as a strategy for in vivo target protein degradation," Science, Jun. 19, 2015, 348(6241):1376-1381.
Yono et al., "Novel metastasis model of human lung cancer cells representing different histological types in SCID mice depleted of NK cells," Gan To Kagaku Ryoho, 1997, 24(4):489-494.
Zhang et al., "Myeloid Cell factor-1 Is a Critical Survival Factor for Multiple Myeloma," *Blood*, 2002, 99(6):1885-93.
Zhong et al., "Mule/ARF-BP1, a BH3-Only E3 Ubiquitin Ligase, Catalyzes the Polyubiquitination of Mcl-1 and Regulates Apoptosis," Cell, vol. 2005, 121:1085-1095.
Caro et al., "Metabolic Signatures Uncover Distinct Targets in Molecular Subsets of Diffuse Large B-Cell Lymphoma," Cancer Cell, Oct. 16, 2013, 22(4):547-560.
Matsubara et al., "Molecular Cloning and Nucleotide Sequence of cDNAs Encoding the Precursors of Rat Long Chain Acyl-Coenzyme A, Short Chain Acyl-Coenzyme A, and Isovaleryl-Coenzyme A Dehydrogenases: Sequence Homology of Four Enzymes of the Acyl-CoA Dehydrogenase Family," Journal of Biological Chemistry, Sep. 25, 1989, 264(27):16321-16331.

* cited by examiner

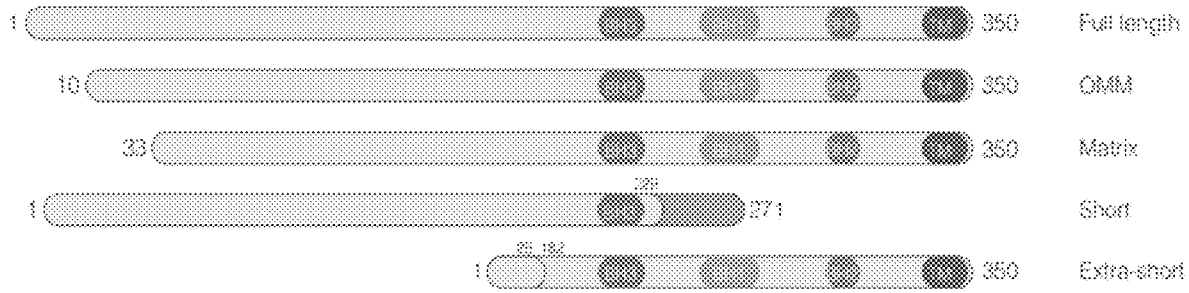

Human full length MCL-1
MFGLKRNAVIGLNLYCGGAGLGAGSGGATRPGGRLLATEKEASARREIGGGEAGAVIGGS
AGASPPSTLTPDSRRVARPPPIGAEVPDVTATPARLLFFAPTRRAAPLEEMEAPAADAIM
SPEEELDGYEPEPLGKRPAVLPLLELVGESGNNTSTDGSLPSTPPPAEEEEDELYRQSLE
IISRYLREQATGAKDTKPMGRSGATSRKALETLRRVGDGVQRNHETAFQGMLRKLDIKNE
DDVKSLSRVMIHVFSDGVTNWGRIVTLISFGAFVAKHLKTINQESCIEPLAESITDVLVR
TKRDWLVKQRGWDGFVEFFHVEDLEGGIRNVLLAFAGVAGVGAGLAYLIR (SEQ ID NO: 1)

Mouse full length MCL-1
MFGLRRNAVIGLNLYCGGASLGAGGGSPAGARLVAEEAKARREGGGEAALLPGARVVARP
PPVGAEDPDVTASAERRLHKSPGLLAVPPEEMAASAAAAIVSPEEELDGCEPEAIGKRPA
VLPLLERVSEAAKSSGADGSLPSTPPPPEEEEDDLYRQSLEIISRYLREQATGSKDSKPL
GEAGAAGRRALETLRRVGDGVQRNHETAFQGMLRKLDIKNEGDVKSFSRVMVHVFKDGVT
NWGRIVTLISFGAFVAKHLKSVNQESFIEPLAETITDVLVRTKRDWLVKQRGWDGFVEFF
HVQDLEGGIRNVLLAFAGVAGVGAGLAYLIR (SEQ ID NO: 2)

Mouse matrix MCL-1
LVAEEAKARREGGGEAALLPGARVVARPPPVGAEDPDVTASAERRLHKSPGLLAVPPEE
MAASAAAAIVSPEEELDGCEPEAIGKRPAVLPLLERVSEAAKSSGADGSLPSTPPPPEE
EEDDLYRQSLEIISRYLREQATGSKDSKPLGEAGAAGRRALETLRRVGDGVQRNHETAF
QGMLRKLDIKNEGDVKSFSRVMVHVFKDGVTNWGRIVTLISFGAFVAKHLKSVNQESFI
EPLAETITDVLVRTKRDWLVKQRGWDGFVEFFHVQDLEGGIRNVLLAFAGVAGVGAGLA
YLIR (SEQ ID NO: 3)

Human matrix MCL-1
LLATEKEASARREIGGGEAGAVIGGSAGASPPSTLTPDSRRVARPPPIGAEVPDVTATP
ARLLFFAPTRRAAPLEEMEAPAADAIMSPEEELDGYEPEPLGKRPAVLPLLELVGESGN
NTSTDGSLPSTPPPAEEEEDELYRQSLEIISRYLREQATGAKDTKPMGRSGATSRKALE
TLRRVGDGVQRNHETAFQGMLRKLDIKNEDDVKSLSRVMIHVFSDGVTNWGRIVTLISF
GAFVAKHLKTINQESCIEPLAESITDVLVRTKRDWLVKQRGWDGFVEFFHVEDLEGGIR
NVLLAFAGVAGVGAGLAYLIR (SEQ ID NO: 4)

XKALXTLRRVGDGVQRNHETAF (SEQ ID NO: 5)
RXALEXLRRVGDGVQRNHETAF (SEQ ID NO: 6)
RKXLETXRRVGDGVQRNHETAF (SEQ ID NO: 7)
RKAXETLXRVGDGVQRNHETAF (SEQ ID NO: 8)
RKALXTLRXVGDGVQRNHETAF * (SEQ ID NO: 9)
RKALEXLRRXGDGVQRNHETAF (SEQ ID NO: 10)
RKALETXRRVXDGVQRNHETAF (SEQ ID NO: 11)
RKALETLXRVGXGVQRNHETAF (SEQ ID NO: 12)
RKALETLRXVGDXVQRNHETAF (SEQ ID NO: 13)
RKALETLRRXGDGXQRNHETAF (SEQ ID NO: 14)
RKALETLRRVXDGVXRNHETAF (SEQ ID NO: 15)
RKALETLRRVGXGVQXNHETAF (SEQ ID NO: 16)
RKALETLRRVGDXVQRXHETAF (SEQ ID NO: 17)
RKALETLRRVGDGXQRNXETAF (SEQ ID NO: 18)
RKALETLRRVGDGVXRNHXTAF ** (SEQ ID NO: 19)
RKALETLRRVGDGVQXNHEXAF (SEQ ID NO: 20)
RKALETLRRVGDGVQRXHETXF (SEQ ID NO: 21)
RKALETLRRVGDGVQRNXETAX (SEQ ID NO: 22)

8KALETLXRVGDGVQRNHETAF (SEQ ID NO: 23)
R8ALETLRXVGDGVQRNHETAF (SEQ ID NO: 24)
RK8LETLRRXGDGVQRNHETAF (SEQ ID NO: 25)
RKA8ETLRRVXDGVQRNHETAF (SEQ ID NO: 26)
RKAL8TLRRVGXGVQRNHETAF (SEQ ID NO: 27)
RKALE8LRRVGDXVQRNHETAF (SEQ ID NO: 28)
RKALET8RRVGDGXQRNHETAF (SEQ ID NO: 29)
RKALETL8RVGDGVXRNHETAF (SEQ ID NO: 30)
RKALETLR8VGDGVQXNHETAF (SEQ ID NO: 31)
RKALETLRR8GDGVQRXHETAF (SEQ ID NO: 32)
RKALETLRRV8DGVQRNXETAF (SEQ ID NO: 33)
RKALETLRRVG8GVQRNHXTAF (SEQ ID NO: 34)
RKALETLRRVGD8VQRNHEXAF (SEQ ID NO: 35)
RKALETLRRVGDG8QRNHETXF (SEQ ID NO: 36)
RKALETLRRVGDGV8RNHETAX (SEQ ID NO: 37)

```
YAREATQAVL DKPETLSSDA STREKPARAE SKSFAVGMFK GQLTIDQVFP
YPSVLSEEQA QFLKELVGPV ARFFEEVNDP AKNDALEKVE DDTLQGLKEL
GAFGLQVPSE LGGLGLSNTQ YARLAEIVGM HDLGVSVTLG AHQSIGFKGI
LLYGTKAQRE KYLPRVASGQ ALAAFCLTEP SSGSDVASIR SSAIPSPCGK
YYTLNGSKIW ISNGGLADIF TVFAKTPIKD AATGAVKEKI TAFVVERSFG
GVTHGLPEKK MGIKASNTSE VYFDGVKVPS ENVLGEVGDG FKVAVNILNN
GRFGMAATLA GTMKSLIAKA VDHATNRTQF GDKIHNFGVI QEKLARMAIL
QYVTESMAYM LSANMDQGFK DFQIEAAISK IFCSEAAWKV ADECIQIMGG
MGFMKEPGVE RVLRDIRIFR IFEGANDILR LFVALQGCMD KGKELTGLGN
ALKNPFGNVG LLMGEAGKQL RRRTGIGSGL SLSGIVHPEL SRSGELAVQA
LDQFATVVEA KLVKHKKGIV NEQFLLQRLA DGAIDLYAMV VVLSRASRSL
SEGYPTAQHE KMLCDSWCIE AATRIRENMA SLQSSPQHQE LFRNFRSISK
AMVENGGLVT GNPLGI    (SEQ ID NO: 38)
```

FIG. 7B

Human Full length VLCAD
MQAARMAASLGRQLLRLGGGSSRLTALLGQPRPGPARRPYAGGAAQLALDKSDSHPSDAL
TRKKPAKAESKSFAVGMFKGQLTTDQVFPYPSVLNEEQTQFLKELVEPVSRFFEEVNDPA
KNDALEMVEETTWQGLKELGAFGLQVPSELGGVGLCNTQYARLVEIVGMHDLGVGITLGA
HQSIGFKGILLFGTKAQKEKYLPKLASGETVAAFCLTEPSSGSDAASIRTSAVPSPCGKY
YTLNGSKLWISNGGLADIFTVFAKTPVTDPATGAVKEKITAFVVERGFGGITHGPPEKKM
GIKASNTAEVFFDGVRVPSENVLGEVGSGFKVAMHILNNGRFGMAAALAGTMRGIIAKAV
DHATNRTQFGEKIHNFGLIQEKLARMVMLQYVTESMAYMVSANMDQGATDFQIEAAISKI
FGSEAAWKVTDECIQIMGGMGFMKEPGVERVLRDLRIFRIFEGTNDILRLFVALQGCMDK
GKELSGLGSALKNPFGNAGLLLGEAGKQLRRRAGLGSGLSLSGLVHPELSRSGELAVRAL
EQFATVVEAKLIKHKKGIVNEQFLLQRLADGAIDLYAMVVVLSRASRSLSEGHPTAQHEK
MLCDTWCIEAAARIREGMAALQSDPWQQELYRNFKSISKALVERGGVVTSNPLGF (SEQ ID NO: 39)

Human VLCAD isoform 2
MQAARMAASLGRQLLRLGGGSSRLTALLGQPRPGPARRPYAGGAAQESKSFAVGMFKGQL
TTDQVFPYPSVLNEEQTQFLKELVEPVSRFFEEVNDPAKNDALEMVEETTWQGLKELGAF
GLQVPSELGGVGLCNTQYARLVEIVGMHDLGVGITLGAHQSIGFKGILLFGTKAQKEKYL
PKLASGETVAAFCLTEPSSGSDAASIRTSAVPSPCGKYYTLNGSKLWISNGGLADIFTVF
AKTPVTDPATGAVKEKITAFVVERGFGGITHGPPEKKMGIKASNTAEVFFDGVRVPSENV
LGEVGSGFKVAMHILNNGRFGMAAALAGTMRGIIAKAVDHATNRTQFGEKIHNFGLIQEK
LARMVMLQYVTESMAYMVSANMDQGATDFQIEAAISKIFGSEAAWKVTDECIQIMGGMGF
MKEPGVERVLRDLRIFRIFEGTNDILRLFVALQGCMDKGKELSGLGSALKNPFGNAGLLL
GEAGKQLRRRAGLGSGLSLSGLVHPELSRSGELAVRALEQFATVVEAKLIKHKKGIVNEQ
FLLQRLADGAIDLYAMVVVLSRASRSLSEGHPTAQHEKMLCDTWCIEAAARIREGMAALQ
SDPWQQELYRNFKSISKALVERGGVVTSNPLGF (SEQ ID NO: 40)

Human VLCAD isoform 3
MLGGLAAAAGTRIMGKEIEAEAQRPLRQTWRPGQPPAMTAKTMSSRLTALLGQPRPGPAR
RPYAGGAAQLALDKSDSHPSDALTRKKPAKAESKSFAVGMFKGQLTTDQVFPYPSVLNEE
QTQFLKELVEPVSRFFEEVNDPAKNDALEMVEETTWQGLKELGAFGLQVPSELGGVGLCN
TQYARLVEIVGMHDLGVGITLGAHQSIGFKGILLFGTKAQKEKYLPKLASGETVAAFCLT
EPSSGSDAASIRTSAVPSPCGKYYTLNGSKLWISNGGLADIFTVFAKTPVTDPATGAVKE
KITAFVVERGFGGITHGPPEKKMGIKASNTAEVFFDGVRVPSENVLGEVGSGFKVAMHIL
NNGRFGMAAALAGTMRGIIAKAVDHATNRTQFGEKIHNFGLIQEKLARMVMLQYVTESMA
YMVSANMDQGATDFQIEAAISKIFGSEAAWKVTDECIQIMGGMGFMKEPGVERVLRDLRI
FRIFEGTNDILRLFVALQGCMDKGKELSGLGSALKNPFGNAGLLLGEAGKQLRRRAGLGS
GLSLSGLVHPELSRSGELAVRALEQFATVVEAKLIKHKKGIVNEQFLLQRLADGAIDLYA
MVVVLSRASRSLSEGHPTAQHEKMLCDTWCIEAAARIREGMAALQSDPWQQELYRNFKSI
SKALVERGGVVTSNPLGF (SEQ ID NO: 41)

Mouse VLCAD
MQSARMTPSVGRQLLRLGARSSRSTTVLQGQPRPISAQRLYAREATQAVLDKPETLSSDA
STREKPARAESKSFAVGMFKGQLTIDQVFPYPSVLSEEQAQFLKELVGPVARFFEEVNDP
AKNDALEKVEDDTLQGLKELGAFGLQVPSELGGLGLSNTQYARLAEIVGMHDLGVSVTLG
AHQSIGFKGILLYGTKAQREKYLPRVASGQALAAFCLTEPSSGSDVASIRSSAIPSPCGK
YYTLNGSKIWISNGGLADIFTVFAKTPIKDAATGAVKEKITAFVVERSFGGVTHGLPEKK
MGIKASNTSEVYFDGVKVPSENVLGEVGDGFKVAVNILNNGRFGMAATLAGTMKSLIAKA
VDHATNRTQFGDKIHNFGVIQEKLARMAILQYVTESMAYMLSANMDQGFKDFQIEAAISK
IFCSEAAWKVADECIQIMGGMGFMKEPGVERVLRDIRIFRIFEGANDILRLFVALQGCMD
KGKELTGLGNALKNPFGNVGLLMGEAGKQLRRRTGIGSGLSLSGIVHPELSRSGELAVQA
LDQFATVVEAKLVKHKKGIVNEQFLLQRLADGAIDLYAMVVVLSRASRSLSEGYPTAQHE
KMLCDSWCIEAATRIRENMASLQSSPQHQELFRNFRSISKAMVENGGLVTGNPLG (SEQ ID NO: 42)

FIG. 18A

| | |
|---|---|
| AKALETLRRVGDGVXRNHXTAF (SEQ ID NO: 43) | R207A |
| RAALETLRRVGDGVXRNHXTAF (SEQ ID NO: 44) | K208A |
| RKAAETLRRVGDGVXRNHXTAF (SEQ ID NO: 45) | L210A |
| RKALATLRRVGDGVXRNHXTAF (SEQ ID NO: 46) | E211A |
| RKALEALRRVGDGVXRNHXTAF (SEQ ID NO: 47) | T212A |
| RKALETARRVGDGVXRNHXTAF (SEQ ID NO: 48) | L213A |
| RKALETLARVGDGVXRNHXTAF (SEQ ID NO: 49) | R214A |
| RKALETLRAVGDGVXRNHXTAF (SEQ ID NO: 50) | R215A |
| RKALETLRRAGDGVXRNHXTAF (SEQ ID NO: 51) | V216A |
| RKALETLRRVADGVXRNHXTAF (SEQ ID NO: 52) | G217A |
| RKALETLRRVGAGVXRNHXTAF (SEQ ID NO: 53) | D218A |
| RKALETLRRVGDAVXRNHXTAF (SEQ ID NO: 54) | G219A |
| RKALETLRRVGDGAXRNHXTAF (SEQ ID NO: 55) | V220A |
| RKALETLRRVGDGVXANHXTAF (SEQ ID NO: 56) | R222A |
| RKALETLRRVGDGVXRAHXTAF (SEQ ID NO: 57) | N223A |
| RKALETLRRVGDGVXRNAXTAF (SEQ ID NO: 58) | H224A |
| RKALETLRRVGDGVXRNHXAAF (SEQ ID NO: 59) | T226A |
| RKALETLRRVGDGVXRNHXTAA (SEQ ID NO: 60) | F228A |

COMPOSITIONS, ASSAYS, AND METHODS FOR DIRECT MODULATION OF FATTY ACID METABOLISM

CROSS-REFERENCE TO RELATED APPLICATIONS

This application is a division of U.S. patent application Ser. No. 16/307,599, filed Dec. 6, 2018, issued as U.S. Pat. No. 11,567,082, which is a U.S. National Stage Application of International Application No. PCT/US2017/040360, filed Jun. 30, 2017, which claims the benefit of priority of U.S. Provisional Appl. No. 62/357,866, filed Jul. 1, 2016, the contents of each of which are incorporated by reference in their entireties herein.

SEQUENCE LISTING

This application contains a Sequence Listing that has been submitted electronically as an XML file named 00530-0332002_SL_ST26.xml. The XML file, created on Dec. 19, 2024, is 109,133 bytes in size. The material in the XML file is hereby incorporated by reference in its entirety.

TECHNICAL FIELD

This disclosure relates to compositions, assays, and methods for applying Myeloid Cell Leukemia-1 (MCL-1) and MCL-1 mimetics (e.g., stapled peptides) to the modulation of fatty acid metabolism (more specifically, fatty acid β-oxidation (which produces ATP/energy for cell growth/proliferation), e.g., for the treatment of cancer or conditions with excessive fatty acid β-oxidation.

BACKGROUND OF THE INVENTION

Mitochondrial apoptosis is essential to normal development and tissue homeostasis. BCL-2 family proteins regulate this process through heterodimeric and homo-oligomeric protein interactions, which ultimately dictate whether a cell will live or die. Engagement of multidomain pro-apoptotic members BAX and BAK by select BH3-only proteins, such as BID, BIM, and PUMA, conformationally activates BAX and BAK, transforming them from monomeric proteins into oligomeric pores that pierce the mitochondrial outer membrane, resulting in apoptosis induction (see, e.g., Walensky and Gavathiotis, *Trends Biochem Sci.*, 36(12):642-52 (2011)). Anti-apoptotic proteins, such as BCL-$X_L$ and MCL-1, bind and block BH3-only and multidomain pro-apoptotic members to prevent mitochondrial apoptosis.

Cancer cells overexpress BCL-2 family anti-apoptotic proteins to exploit this mechanism and enforce cellular immortality. Myeloid Cell Leukemia-1 (MCL-1), an anti-apoptotic BCL-2 family survival protein, has been implicated in the development, maintenance, and chemoresistance of a broad range of cancers and is one of the top ten most widely expressed pathologic factors in human cancers (see, e.g., Beroukhim, *Nature*, 463(7283):899-905 (2010)). Highly overexpressed in human cancers, MCL-1 mounts formidable apoptotic resistance by binding and sequestering the essential BH3 domain helices of pro-apoptotic BCL-2 family members. Underscoring the physiologic importance of MCL-1, mouse models of MCL-1 deletion have revealed severe consequences, including embryonic lethality, hematopoietic stem cell loss, cardiomyopathy, mitochondrial dysfunction, and more (see, e.g., Rinkenberger, *Genes Dev.*, 14(1):23-27 (2000), Malone, *Mol Cell Neurosci.*, 49(4):439-47 (2012), Opferman, *Science*, 307(5712):1101-4 (2005), Opferman, *Nature*, 426(6967):671-6 (2003), Wang, *Genes Dev.* 2013). Ironically, the MCL-1 BH3 domain is itself the most potent and selective natural inhibitor of MCL-1's anti-apoptotic function (see, e.g., Stewart, *Nat Chem Biol.*, 6(6):595-601(2010)).

Fatty acid metabolism is a distinct process that, like mitochondrial apoptosis, is also essential to normal development and tissue homeostasis. To support the energetic needs of tissues, both normal and oncologic fatty acids that enter the cell undergo mitochondrial β-oxidation (FIG. 35). Fatty acids are first charged by acyl-CoA synthetase long-chain family member 1 (ACSL1) to generate the corresponding acyl-CoA species. Because long chain acyl-CoAs cannot reach the mitochondrial matrix by passive diffusion, they are first converted to acylcarnitines and then transported via the carnitine-acylcamitine translocase (CACT). Once in the mitochondrial matrix, acylcarnitines are converted back to acyl-CoAs by carnitine palmitoyltransferase 2 (CPT2), enabling entry into the β-oxidation pathway. The critically important enzyme Very Long Chain Acyl CoA Dehydrogenase (VLCAD) catalyzes the first of four steps in a process that mobilizes fatty acids to produce cellular fuel/energy by reducing the length of long-chain acyl-CoAs by two carbons, sequentially releasing acetyl-CoA. VLCAD deficiency in humans can cause an early-onset severe condition characterized by life-threatening cardiomyopathy and a later-onset disease that manifests as repeated episodes of hypoglycemia.

SUMMARY

The present disclosure provides assays, compositions, and methods of modulating fatty acid metabolism, and methods of treatment of cancer or conditions with excessive fatty acid β-oxidation.

In a first aspect, the disclosure features a method for treating or preventing a Myeloid Cell Leukemia-1 (MCL-1)-associated disease or disorder in a human subject in need thereof. The method involves administering to the human subject an agent that inhibits interaction between MCL-1 and Very Long Chain Acyl CoA Dehydrogenase (VLCAD), or directly inhibits VLCAD, thereby treating or preventing the disease or disorder in the human subject.

In certain embodiments, the agent comprises a Bcl-2 homology 3 (BH3) domain polypeptide. In some embodiments, the BH3 domain polypeptide comprises a stapled BH3 domain polypeptide. In some embodiments, the BH3 domain polypeptide comprises a hydrocarbon-stapled BH3 domain polypeptide. In some embodiments, the stapled BH3 domain polypeptide comprises a MCL-1 Stabilized Alpha-Helix of BCL-2 domain (SAHB) peptide. In a particular embodiment, the MCL-1 SAHB peptide is MCL-1 SAHB$_D$. In some instances, the MCL-1 SAHB peptide has an amino acid sequence that is identical to the amino acid sequence set forth in SEQ ID NO:19, except for 1 to 6 (i.e., 1, 2, 3, 4, 5, or 6) amino acid substitutions. In certain instances, the substitutions are on the face of the helix formed by SEQ ID NO:19 that does not interact with VLCAD. In certain instances, the substitutions are on the face of the helix formed by SEQ ID NO:19 that does not interact with MCL-1. In certain instances, the substitutions are on the face of the helix formed by SEQ ID NO:19 that interacts with VLCAD. In some embodiments of this case, the substitutions are conservative substitutions. In some embodiments of this case, the substitutions can be non-conservative so long as they do not disrupt the key molecular interactions with the binding surface. In certain instances, the substitutions are on the face of the helix formed by SEQ ID NO:19 that interacts with MCL-1. In some embodiments of this case, the substitutions are conservative substitutions. In some embodiments of this case, the substitutions can be non-conservative so long as they do not disrupt the key molecular interactions with the binding surface.

In some instances, the MCL-1 SAHB peptide has an amino acid sequence that is identical to the amino acid sequence set forth in any one of SEQ ID NOs:43-60, except for 1 to 6 (i.e., 1, 2, 3, 4, 5, or 6) amino acid substitutions. In some instances, the MCL-1 SAHB peptide has an amino acid sequence that is identical to an amino acid sequence set forth in any one of SEQ ID NOs: 43-60, except for 1 to 2 amino acid substitutions. In certain instances, the substitutions are on the face of the helix formed by any one of SEQ ID NOs: 43-60 that does not interact with VLCAD. In certain instances, the substitutions are on the face of the helix formed by any one of SEQ ID NOs: 43-60 that does not interact with MCL-1. In certain instances, the substitutions are on the face of the helix formed by any one of SEQ ID NOs: 43-60 that interacts with VLCAD. In some embodiments of this case, the substitutions are conservative substitutions. In some embodiments of this case, the substitutions can be non-conservative so long as they do not disrupt the key molecular interactions with the binding surface. In certain instances, the substitutions are on the face of the helix formed by any one of SEQ ID NOs: 43-60 that interacts with MCL-1. In some embodiments of this case, the substitutions are conservative substitutions. In some embodiments of this case, the substitutions can be non-conservative so long as they do not disrupt the key molecular interactions with the binding surface.

In some instances, the MCL-1 SAHB peptide has an amino acid sequence that is identical to the amino acid sequence set forth in any one of SEQ ID NOs:43-60. In some instances, the MCL-1 SAHB peptide has an amino acid sequence that is identical to the amino acid sequence set forth in any one of SEQ ID NOs:43-47, 50-57, and 59. In one instance, the MCL-1 SAHB peptide has an amino acid sequence that is identical to the amino acid sequence set forth in SEQ ID NO: 53. In another instance, the MCL-1 SAHB peptide has an amino acid sequence that is identical to the amino acid sequence set forth in SEQ ID NO: 55. In certain instances, the MCL-1 peptide is 20-100 amino acids in length. In certain instances, the MCL-1 polypeptide is 20-80 amino acids in length. In certain instances, the MCL-1 peptide is 20-50 amino acids in length. In certain instances, the MCL-1 polypeptide is 20-40 amino acids in length. In certain instances, the MCL-1 peptide is 20-30 amino acids in length. In certain instances, the MCL-1 peptide is 22 amino acids in length. In certain instances, the MCL-1 peptide is 25 amino acids in length.

The agent is administered at an amount that is effective to treat or prevent the Myeloid Cell Leukemia-1 (MCL-1)-associated disease or disorder. In certain instances, the agent is administered at a dose of 1000 µM or less, 500 µM or less, 250 µM or less, 100 µM or less, 50 µM or less, 25 µM or less, 20 µM or less, 15 µM or less, 14 µM or less, 13 µM or less, 12 µM or less, 11 µM or less, 10 µM, 5 µM or less. In other instances, the agent is administered at a dose of 1000 µM, 500 µM, 250 µM, 100 µM, 50 µM, 25 µM, 20 µM, 19 µM, 18 µM, 17 µM, 16 µM, 15 µM, 14 µM, 13 µM, 12 µM, 11 µM, 10 µM, 9 µM, 8 µM, 7 µM, 6 µM, 5 µM, 4 µM, 3 µM, 2 µM, 1 µM or 0.5 µM. In certain instances, the agent is administered at a dose such that apoptosis is not triggered by blocking the anti-apoptotic functionality of MCL-1. In certain instances, the agent is administered at any dose where apoptosis of cancer cells or hyperproliferative cells is not necessarily or exclusively triggered by blocking the canonical anti-apoptotic functionality of MCL-1. In certain embodiments, the disease or disorder is characterized by MCL-1 expression or dependence in cancer. In certain embodiments, the disease or disorder is a disease or disorder that expresses MCL-1. In certain embodiments, the disease or disorder is a disease or disorder that relies on fatty acid β-oxidation. In certain embodiments, the disease or disorder is a disease or disorder that expresses MCL-1 and relies on fatty acid β-oxidation. In certain embodiments, the disease or disorder is a cancer that expresses MCL-1. In certain embodiments, the disease or disorder is a cancer of the breast, respiratory tract, brain, reproductive organs, digestive tract, urinary tract, eye, liver, lung, skin, head and neck, thyroid, parathyroid or a metastasis of a solid tumor. In some embodiments, the disease or disorder is a lymphoma, a leukemia, a carcinoma, a multiple myeloma, a melanoma, or a sarcoma. In some embodiments, the disease or disorder is selected from the group consisting of lymphoma, leukemia, carcinoma, multiple myeloma, melanoma, sarcoma, colorectal cancer, breast cancer, liver cancer, renal cancer, lung cancer, stomach cancer, glioma, and thyroid cancer. In specific embodiments, the disease or disorder is selected from the group consisting of breast cancer (e.g., triple negative, i.e., negative for estrogen receptor, progesterone receptor, and the HER-2/neu receptor), diffuse large B-cell lymphoma, acute myeloid leukemia (AML), acute lymphoblastic leukemia (ALL), multiple myeloma, lung carcinoma, glioma, breast sarcoma, and breast carcinoma. In certain embodiments, the method further involves administering an effective amount of a chemotherapeutic agent to the subject. The administration of the agent that inhibits interaction between MCL-1 and VLCAD and the chemotherapeutic agent can be simultaneous or sequential. In certain embodiments, the disease or disorder is one that is characterized by excessive fatty acid β-oxidation.

In a second aspect, the disclosure features a method of reducing or lowering fatty acid β-oxidation in a cell. Thus, this method can be used to decrease ATP/energy production in the cell. The method involves contacting the cell with a composition comprising an agent that inhibits the interaction between MCL-1 and VLCAD, or directly inhibits VLCAD. The method results in reducing or lowering fatty acid β-oxidation in the cell relative to fatty acid β-oxidation in the cell not contacted with the agent.

In certain embodiments, the cell is a cancer cell. In other embodiments, the cell is one that is characterized by excessive fatty acid β-oxidation. In certain instances, the cell is in a human subject in need of reducing or lowering fatty acid β-oxidation. In certain embodiments, the agent comprises a Bcl-2 homology 3 (BH3) domain polypeptide. In certain instances, the BH3 domain is from MCL-1. In some embodiments, the BH3 domain polypeptide comprises a stapled BH3 domain polypeptide. In some embodiments, the stapled BH3 domain polypeptide comprises a MCL-1 Stabilized Alpha-Helix of BCL-2 domain (SAHB) peptide. In a particular embodiment, the MCL-1 SAHB peptide is MCL-1 SAHB$_D$. In some instances, the MCL-1 SAHB peptide has an amino acid sequence that is identical to the amino acid sequence set forth in SEQ ID NO: 19, except for 1 to 6 (i.e., 1, 2, 3, 4, 5, or 6) amino acid substitutions. In certain instances, the substitutions are on the face of the helix formed by SEQ ID NO:19 that does not interact with VLCAD. In certain instances, the substitutions are on the face of the helix formed by SEQ ID NO:19 that does not interact with MCL-1. In certain instances, the substitutions are on the face of the helix formed by SEQ ID NO:19 that interacts with VLCAD. In some embodiments of this case, the substitutions are conservative substitutions. In some embodiments of this case, the substitutions can be non-conservative so long as they do not disrupt the key molecular interactions with the binding surface. In certain instances, the substitutions are on the face of the helix formed by SEQ ID NO:19 that interacts with MCL-1. In some embodiments of this case, the substitutions are conservative substitutions. In some embodiments of this case, the substitutions can be non-conservative so long as they do not disrupt the key molecular interactions with the binding surface.

In some instances, the MCL-1 SAHB peptide has an amino acid sequence that is identical to the amino acid sequence set forth in any one of SEQ ID NOs:43-60, except for 1 to 6 (i.e., 1, 2, 3, 4, 5, or 6) amino acid substitutions. In some instances, the MCL-1 SAHB peptide has an amino acid sequence that is identical to an amino acid sequence set forth in any one of SEQ ID NOs: 43-60, except for 1 to 2 amino acid substitutions. In certain instances, the substitutions are on the face of the helix formed by any one of SEQ ID NOs: 43-60 that does not interact with VLCAD. In certain instances, the substitutions are on the face of the helix formed by any one of SEQ ID NOs: 43-60 that does not interact with MCL-1. In certain instances, the substitutions are on the face of the helix formed by any one of SEQ ID NOs: 43-60 that interacts with VLCAD. In some embodiments of this case, the substitutions are conservative substitutions. In some embodiments of this case, the substitutions can be non-conservative so long as they do not disrupt the key molecular interactions with the binding surface. In certain instances, the substitutions are on the face of the helix formed by any one of SEQ ID NOs: 43-60 that interacts with MCL-1. In some embodiments of this case, the substitutions are conservative substitutions. In some embodiments of this case, the substitutions can be non-conservative so long as they do not disrupt the key molecular interactions with the binding surface.

In some instances, the MCL-1 SAHB peptide has an amino acid sequence that is identical to the amino acid sequence set forth in any one of SEQ ID NOs:43-60. In some instances, the MCL-1 SAHB peptide has an amino acid sequence that is identical to the amino acid sequence set forth in any one of SEQ ID NOs:43-47,50-57, and 59. In one instance, the MCL-1 SAHB peptide has an amino acid sequence that is identical to the amino acid sequence set forth in SEQ ID NO: 53. In another instance, the MCL-1 SAHB peptide has an amino acid sequence that is identical to the amino acid sequence set forth in SEQ ID NO: 55. In certain instances, the MCL-1 peptide is 20-100 amino acids in length. In certain instances, the MCL-1 polypeptide is 20-80 amino acids in length. In certain instances, the MCL-1 peptide is 20-50 amino acids in length. In certain instances, the MCL-1 polypeptide is 20-40 amino acids in length. In certain instances, the MCL-1 peptide is 20-30 amino acids in length. In certain instances, the MCL-1 peptide is 22 amino acids in length. In certain instances, the MCL-1 peptide is 25 amino acids in length. In certain instances, the method further involves determining that fatty acid β-oxidation or ATP/energy production in the cell is lowered. In other instances, the method further involves determining that cell proliferation is decreased or blocked.

In a third aspect, the disclosure features a method for inhibiting the interaction between MCL-1 and VLCAD. The method involves contacting a mixture comprising MCL-1 and VLCAD with an agent that binds VLCAD and/or MCL-1 to disrupt VLCAD activity. In certain embodiments, the method further involves determining that the agent inhibits the interaction between MCL-1 and VLCAD.

In a fourth aspect, the disclosure provides a method for identifying a compound that modulates MCL-1/VLCAD interaction. The method involves contacting an MCL-1 polypeptide (e.g., a BH3 domain containing MCL-1 polypeptide or a mimetic thereof) and a VLCAD polypeptide (e.g., any VLCAD polypeptide shown in FIG. 7B or an enzymatically active fragment thereof) with a test compound and detecting a reduction in interaction between the MCL-1 polypeptide and the VLCAD polypeptide relative to the interaction between the MCL-1 polypeptide and the VLCAD polypeptide in the absence of the test compound. Detection of a reduced interaction between the MCL-1 polypeptide and the VLCAD polypeptide identifies the test compound as a compound that modulates the MCL-1/VLCAD interaction.

In certain embodiments, the test compound is a polypeptide. In certain instances, the polypeptide is a BH3 domain polypeptide. In some instances, the BH3 domain polypeptide is a SAHB. In certain embodiments, the test compound is a small molecule. In other embodiments, the test compound is a monobody or intrabody. In other embodiments, the test compound comprises a degron (e.g., a compound comprising a BH3 domain (e.g., from MCL-1) or a mimetic thereof attached to a degron).

In a fifth aspect, the disclosure provides a method for identifying an agent that inhibits the enzymatic activity of VLCAD. The method involves contacting a VLCAD polypeptide (e.g., any VLCAD polypeptide shown in FIG. 7B or an enzymatically active fragment thereof) with a test compound, and determining that the test compound decreases the enzymatic activity of VLCAD relative to the enzymatic assay of VLCAD determined in the absence of contacting the VLCAD polypeptide with the test compound. The test compound is identified as an inhibitor of the enzymatic activity of VLCAD.

In certain embodiments, the VLCAD polypeptide and the test compound are contacted in the presence of palmitoyl-CoA and ferrocenium hexafluorophosphate. In some embodiments, the test compound is a polypeptide. In certain instances, the polypeptide is a BH3 domain polypeptide. In certain instances, the BH3 domain is from MCL-1. In some instances, the BH3 domain polypeptide is a SAHB. In certain instances, the test compound is a small molecule. In other embodiments, the test compound is a monobody or intrabody. In other embodiments, the test compound comprises a degron (e.g., a compound comprising a BH3 domain (e.g., from MCL-1) or a mimetic thereof attached to a degron).

In a sixth aspect, the disclosure features a method for identifying a test compound for treating a cancer that expresses MCL-1. The method involves contacting a VLCAD polypeptide e.g., any VLCAD polypeptide shown in FIG. 7B or an enzymatically active fragment thereof, with a MCL-1 BH3 polypeptide or mimetic thereof; determining that the MCL-1 BH3 polypeptide or mimetic thereof binds the VLCAD polypeptide; and identifying the MCL-1 BH3 polypeptide or mimetic thereof that binds VLCAD as a compound for treating the cancer.

In certain embodiments, the MCL-1 BH3 polypeptide or mimetic thereof that binds VLCAD inhibits VLCAD enzymatic activity. In certain embodiments, the cancer that expresses MCL-1 is selected from the group consisting of lymphoma, leukemia, carcinoma, multiple myeloma, melanoma, sarcoma, colorectal cancer, breast cancer, liver cancer, renal cancer, lung cancer, stomach cancer, glioma, and thyroid cancer.

In a seventh aspect, the disclosure features a chimeric compound comprising a molecule described herein attached or linked to a degron. In certain embodiments, the molecule attached to the degron comprises a Bcl-2 homology 3 (BH3) domain polypeptide. In certain instances, the BH3 domain is from MCL-1. In some embodiments, the BH3 domain polypeptide comprises a stapled BH3 domain polypeptide. In some embodiments, the stapled BH3 domain polypeptide comprises a MCL-1 Stabilized Alpha-Helix of BCL-2 domain (SAHB) peptide. In a particular embodiment, the MCL-1 SAHB peptide is MCL-1 SAHB$_D$.

In an eighth aspect, the disclosure provides a method for identifying a test compound for treating a subject with excessive fatty acid β-oxidation. The method involves contacting a VLCAD polypeptide with a MCL-1 BH3 polypeptide or a mimetic thereof and determining that the MCL-1 BH3 polypeptide or a mimetic thereof binds the VLCAD polypeptide. The MCL-1 BH3 polypeptide or a mimetic thereof that binds the VLCAD polypeptide is identified as a compound for treating excessive fatty acid β-oxidation.

In some embodiments, the MCL-1 BH3 polypeptide or a mimetic thereof that binds VLCAD inhibits VLCAD enzymatic activity. In some instances, the cell manifesting excessive fatty acid β-oxidation is a metabolically stressed cell, a hypoxic cell, a fasted cell, a VLCAD deficient cell, a blood cell, an immune cell, a smooth muscle cell, a skeletal muscle cell, a heart muscle cell, a neuronal cell, a liver cell, an islet cell, or a fat cell.

In a ninth aspect, the disclosure provides a stabilized MCL-1 peptide.

In some instances of this aspect, the stabilized peptide is a stapled MCL-1 SAHB peptide. In some instances of this aspect, the stabilized peptide is a hydrocarbon stapled MCL-1 SAHB peptide. In some instances, the stabilized peptide is a MCL-1 SAHB peptide with a triazole-containing crosslink. In some instances, the stabilized peptide is a MCL-1 SAHB peptide with a lactam-containing crosslink. In some instances, the stabilized peptide is a MCL-1 SAHB peptide that is disulfide stapled. In some instances, the stabilized peptide is a MCL-1 SAHB peptide that is UV-cycloaddition stapled. In some instances, the stabilized peptide is a MCL-1 SAHB peptide that is oxime stapled. In some instances, the stabilized peptide is a MCL-1 SAHB peptide that is thioether stapled. In some instances, the stabilized peptide is a MCL-1 SAHB peptide that is photoswitchable stapled. In some instances, the stabilized peptide is a MCL-1 SAHB peptide that is double-click stapled. In some instances, the stabilized peptide is a MCL-1 SAHB peptide that is bis-lactam stapled. In some instances, the stabilized peptide is a MCL-1 SAHB peptide that is bis-arylation stapled. In certain instances, the stabilized MCL-1 peptide comprises a degron.

In certain embodiments of this aspect, the stabilized MCL-1 peptide is identical to an amino acid sequence set forth in any one of SEQ ID NOs.:43-60, except for 1 to 6 (i.e., 1, 2, 3, 4, 5, or 6) amino acid substitutions, and the stabilized MCL-1 peptide binds to MCL-1 and/or VLCAD. In certain embodiments, the stabilized MCL-1 peptide is identical to an amino acid sequence set forth in any one of SEQ ID NOs.:43-47, 50-57, or 59, except for 1 to 6 (i.e., 1, 2, 3, 4, 5, or 6) amino acid substitutions, and the stabilized MCL-1 peptide binds to MCL-1 and/or VLCAD. In one embodiment, the stabilized MCL-1 peptide is identical to an amino acid sequence set forth in any one of SEQ ID NOs.:43-47, 50-57, or 59, except for 1 to 2 amino acid substitutions, and the stabilized MCL-1 peptide binds to MCL-1 and/or VLCAD. In certain instances, the substitutions are on the face of the helix formed by any one of SEQ ID NOs: 43-47, 50-57, or 59 that does not interact with VLCAD. In certain instances, the substitutions are on the face of the helix formed by any one of SEQ ID NOs: 43-47, 50-57, or 59 that does not interact with MCL-1. In certain instances, the substitutions are on the face of the helix formed by any one of SEQ ID NOs: 43-47, 50-57, or 59 that interacts with VLCAD. In some embodiments of this case, the substitutions are conservative substitutions. In some embodiments of this case, the substitutions can be non-conservative so long as they do not disrupt the key molecular interactions with the binding surface. In certain instances, the substitutions are on the face of the helix formed by any one of SEQ ID NOs: 43-47, 50-57, or 59 that interacts with MCL-1. In some embodiments of this case, the substitutions are conservative substitutions. In some embodiments of this case, the substitutions can be non-conservative so long as they do not disrupt the key molecular interactions with the binding surface.

In certain embodiments, the stabilized MCL-1 peptide is identical to an amino acid sequence set forth in SEQ ID NO: 53 or 55. In certain embodiments, the stabilized MCL-1 peptide is identical to an amino acid sequence set forth in SEQ ID NO:46 or 47. In certain embodiments, the stabilized MCL-1 peptide is identical to an amino acid sequence set forth in any one of SEQ ID NOs.:47, 51, 52, or 55. In certain embodiments, the stabilized MCL-1 peptide is identical to an amino acid sequence set forth in SEQ ID NO:45 or 50. In certain embodiments, the stabilized MCL-1 peptide is identical to an amino acid sequence set forth in any one of SEQ ID NOs.: 19, 46, 53, or 54. In one embodiment, the stabilized MCL-1 peptide is identical to an amino acid sequence set forth in SEQ ID NO.:53. In another embodiment, the stabilized MCL-1 peptide is identical to an amino acid sequence set forth in SEQ ID NO.:55. In certain embodiments, the stabilized MCL-1 peptide comprises a benzophenone moiety. In some instances, the two "X's" in each of the sequences set forth in SEQ ID NOs.: 43-60 are the same non-natural amino acid. In other instances, the two "X's" in each of the sequences set forth in SEQ ID NOs.: 43-60 are different non-natural amino acids. In one particular embodiment, the two "X's" in each of the sequences set forth in SEQ ID NOs.: 43-60 are S5 (i.e., (S)-2-(4-pentenyl) Ala-OH). In certain embodiments, the stabilized MCL-1 peptide is combined with, or administered with, an anti-cancer agent/therapy. In one embodiment, the stabilized MCL-1 peptide is combined with, or administered with, a chemotherapeutic agent. In another embodiment, the stabilized MCL-1 peptide is combined with, or administered with, a radiotherapeutic agent.

In certain embodiments, the stabilized MCL-1 peptide binds VLCAD better than MCL-1. Such peptides include those set forth under SEQ ID NOs.: 47, 51, 52, and 55. In certain embodiments, the stabilized MCL-1 peptide binds MCL-1 better than VLCAD. Such peptides include those set forth under SEQ ID NOs.: 45 and 50. In certain embodiments, the stabilized MCL-1 peptide binds both MCL-1 and VLCAD. Such peptides include those set forth under SEQ ID NOs.: 19, 46, 53, and 54.

In a tenth aspect, the disclosure features a photoreactive stabilized peptide.

In some embodiments of this aspect, the photoreactive stabilized peptide is a stapled MCL-1 SAHB peptide. In some embodiments of this aspect, the photoreactive stabilized peptide is a hydrocarbon stapled MCL-1 SAHB peptide. In some instances, the photoreactive stabilized peptide is a MCL-1 SAHB peptide with a triazole-containing cross-link. In some instances, the photoreactive stabilized peptide is a MCL-1 SAHB peptide with a lactam-containing cross-link. In some instances, the photoreactive stabilized peptide is a MCL-1 SAHB peptide that is disulfide stapled. In some instances, the photoreactive stabilized peptide is a MCL-1 SAHB peptide that is UV-cycloaddition stapled. In some instances, the photoreactive stabilized peptide is a MCL-1 SAHB peptide that is oxime stapled. In some instances, the photoreactive stabilized peptide is a MCL-1 SAHB peptide that is thioether stapled. In some instances, the photoreactive stabilized peptide is a MCL-1 SAHB peptide that is photo-switchable stapled. In some instances, the photoreactive stabilized peptide is a MCL-1 SAHB peptide that is double-click stapled. In some instances, the photoreactive stabilized peptide is a MCL-1 SAHB peptide that is bis-lactam stapled. In some instances, the photoreactive stabilized peptide is a MCL-1 SAHB peptide that is bis-arylation stapled. In certain instances, the photoreactive stabilized MCL-1 peptide comprises a degron.

In certain embodiments of this aspect, the photoreactive stabilized MCL-1 peptide is identical to an amino acid sequence set forth in any one of SEQ ID NOs.:43-60, except for 1 to 6 (i.e., 1, 2, 3, 4, 5, or 6) amino acid substitutions. In certain embodiments, the photoreactive stabilized MCL-1 peptide is identical to an amino acid sequence set forth in any one of SEQ ID NOs.:43-47, 50-57, or 59, except for 1 to 6 (i.e., 1, 2, 3, 4, 5, or 6) amino acid substitutions, and the stabilized MCL-1 peptide binds to MCL-1 and/or VLCAD. In one embodiment, the photoreactive stabilized MCL-1 peptide is identical to an amino acid sequence set forth in any one of SEQ ID NOs.:43-47, 50-57, or 59, except for 1 to 2 amino acid substitutions, and the stabilized MCL-1 peptide binds to MCL-1 and/or VLCAD. In certain instances, the substitutions are on the face of the helix formed by any one of SEQ ID NOs: 43-47, 50-57, or 59 that does not interact with VLCAD. In certain instances, the substitutions are on the face of the helix formed by any one of SEQ ID NOs: 43-47, 50-57, or 59 that does not interact with MCL-1. In certain instances, the substitutions are on the face of the helix formed by any one of SEQ ID NOs: 43-47, 50-57, or 59 that interacts with VLCAD. In some embodiments of this case, the substitutions are conservative substitutions. In some embodiments of this case, the substitutions can be non-conservative so long as they do not disrupt the key molecular interactions with the binding surface. In certain instances, the substitutions are on the face of the helix formed by any one of SEQ ID NOs: 43-47, 50-57, or 59 that interacts with MCL-1. In some embodiments of this case, the substitutions are conservative substitutions. In some embodiments of this case, the substitutions can be non-conservative so long as they do not disrupt the key molecular interactions with the binding surface.

In certain embodiments, the photoreactive stabilized MCL-1 peptide is identical to an amino acid sequence set forth in SEQ ID NO:61. In certain embodiments, the photoreactive stabilized MCL-1 peptide is identical to an amino acid sequence set forth in SEQ ID NO:62. In certain embodiments, the photoreactive stabilized MCL-1 peptide is identical to an amino acid sequence set forth in SEQ ID NO:63. In certain embodiments, the photoreactive stabilized MCL-1 peptide comprises a benzophenone moiety. In some instances, the two "X's" in each of the sequences set forth in SEQ ID NOs.:61-63 are the same non-natural amino acid. In other instances, the two "X's" in each of the sequences set forth in SEQ ID NOs.:61-63 are different non-natural amino acids. In one particular embodiment, the two "X's" in each of the sequences set forth in SEQ ID NOs.:61-63 are S5.

As used herein, the terms "about" and "approximately" are defined as being within plus or minus 10% of a given value or state, preferably within plus or minus 5% of said value or state.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 1A is a schematic of known MCL-1 isoforms—outer mitochondrial matrix (OMM) and matrix forms are produced via proteolytic cleavage of the full length polypeptide chain, while short and extra-short forms are produced via alternative splicing events.

FIG. 1B lists the full-length sequences of human and mouse MCL-1, and human matrix and mouse matrix MCL-1.

FIG. 2 is a series of exemplary sequence templates from the MCL-1 BH3 domain depicting an i, i+4 (top) and an i, i+7 (bottom) staple walk. Exemplary non-natural stapling amino acids are indicated by X, S-pentenyl alanine and 8, R-octenyl alanine. *, MCL-1 SAHB$_B$; **, MCL-1 SAHB$_D$.

FIG. 7A is a depiction of the MS sequence coverage (bold) of the mitochondrial matrix enzyme, VLCAD, which repeatedly emerged as a high-stringency hit from MCL-1 SAHB$_D$ eluates.

FIG. 7B lists the full-length sequences of human and mouse VLCAD, and human VLCAD isoforms 2 and 3.

FIG. 18A provides the amino acid sequences of stapled MCL-1 BH3 peptides bearing sequential alanine scanning point mutations. X is a non-natural amino acid. The two X's in any of the sequences provided can be the same non-natural amino acid or different non-natural amino acids. In some instances, the two X's in any of these sequences are S5 [i.e., (S)-2-(4-pentenyl)Ala-OH].

DETAILED DESCRIPTION

Figure 3:
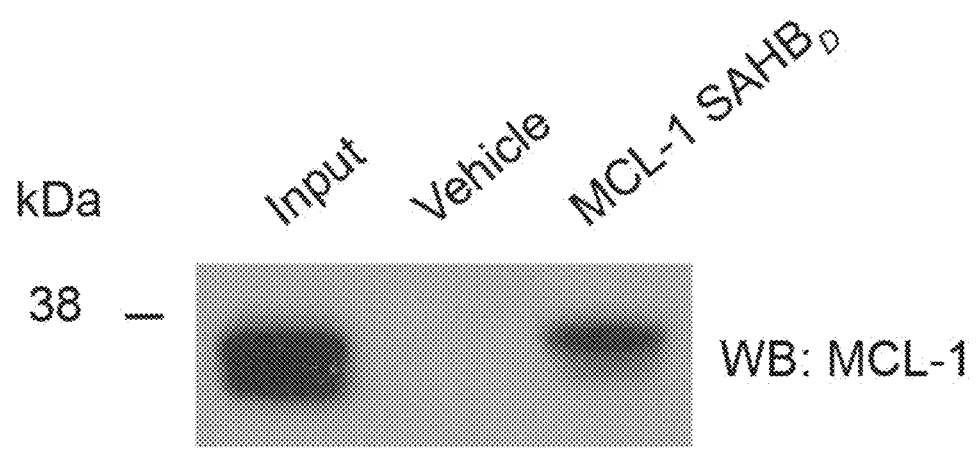
FIG. 3 is a Western blot showing that N-terminal-biotinylated MCL-1 SAHB$_D$ can directly bind to and pull down endogenous/native MCL-1 from cellular lysates.

This disclosure is based on the unexpected and surprising finding that the key apoptosis inhibitor MCL-1 also has an unrelated, distinct role in regulating mitochondrial fatty acid metabolism. In particular, we found that the MCL-1 BH3 α-helix directly and selectively engages VLCAD (Examples 1-3), revealing a novel role for MCL-1 in regulating fatty acid β-oxidation through VLCAD interaction. Upon Mcl-1 deletion (Examples 6-7) or treatment with an MCL-1 stapled peptide mimicking the MCL-1 BH3 domain (i.e., a MCL-1 Stabilized Alpha-Helix of BCL-2 Domain (SAHB)) such as MCL-1 SAHB$_D$ (Example 8), long-chain fatty acid oxidation is impaired, leading to increased levels of long chain acylcamitines. Importantly, the in vitro and cellular observations of an inhibition of fatty acid β-oxidation translate to the in vivo context (Examples 9-10), where we confirmed that targeted MCL-1 deletion in the liver likewise causes suppression of VLCAD function (Example 9). Consistent with MCL-1's key role in regulating metabolism, loss of MCL-1 inhibits cellular proliferation (Example 11). Thus, MCL-1 expression is required for homeostatic fatty acid β-oxidation and the homeostatic function of VLCAD. This non-canonical role for MCL-1 in inhibiting fatty acid metabolism could potentially be the cause of the fatal cardiomyopathy phenotype shared by mice with targeted Mcl-1 deletion in the heart (see, e.g., Wang, Genes Dev. 2013) and children who inherit the severe, early-onset form of VLCAD deficiency.

The ability of MCL-1 to bind and modulate VLCAD informs anew pathway for MCL-1 control over metabolism. In particular, the capacity of overexpressed MCL-1 in cancer cells to enhance VLCAD-mediated fuel generation through fatty acid oxidation can confer a critically important survival advantage on tumor cells, relative to normal cells. Targeting this pathway in cancer cells can inhibit or block the fuel/ energy/ATP production required for cell division and survival and thereby treat the cancer.

Thus, this disclosure provides for novel treatment strategies to treat MCL-1-associated disorders by inhibiting fatty acid β-oxidation, e.g., to inhibit or block cell growth or proliferation in the context of conditions of cellular excess, e.g., any cancers that maintain expression of MCL-1, such as lung cancer, lymphoma, leukemia, carcinoma, multiple myeloma, melanoma, sarcoma, breast cancer, colorectal cancer, liver cancer, renal cancer, stomach cancer, thyroid cancer and glioma. Such strategies can include, e.g., the administration of MCL-1 domain analogs or mimetics (e.g., MCL-1 SAHBs such as MCL-1 SAHB$_D$ or any one of the SAHB$_D$ Ala variants of FIG. 18A) that target VLCAD and thereby disrupt the native MCL-1/VLCAD complex and/or VLCAD enzymatic activity. Typically, the agent (e.g., a MCL-1 SAHB) is substantially purified prior to administration. The subject can be an animal, including but not limited to, cows, pigs, horses, chickens, cats, dogs, and the like, and is typically a mammal, and in a particular aspect human.

Stabilized Peptides

Stapled (e.g., hydrocarbon stapled) peptides (including MCL-1 SAHBs) are polypeptides having at least two modified amino acids, stably cross-linked to help conformationally bestow the native secondary structure of the polypeptide.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., *J Org Chem.*, 66: 5291-5302, 2001; Angew et al., *Chem Int Ed.* 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008121767 and WO 2010/068684, which are both hereby incorporated by reference in their entirety. In some instances, staples, as used herein, can retain the unsaturated bond or can be reduced (e.g., as mentioned below in the stitching paragraph description).

Hydrocarbon stapling allows a polypeptide, predisposed to have an α-helical secondary structure, to maintain its native α-helical conformation. This secondary structure increases resistance of the polypeptide to proteolytic cleavage and heat, and also may increase target binding affinity, hydrophobicity, and cell permeability. Accordingly, the hydrocarbon stapled (cross-linked) polypeptides described herein have improved biological activity relative to a corresponding non-hydrocarbon stapled (un-cross-linked) polypeptide. For example, the cross-linked polypeptide can include an α-helical domain of a BH3 BCL-2 homology domain, which, at least in the case of exemplary NOXA, BOK, and MCL-1 BH3 domains, can competitively interfere with the interaction of MCL-1 protein with native ligands (including, e.g., formation of MCL-1 dimers and/or multimers and/or the MCL-1/BAK heterodimer), thereby modulating MCL-1 activity in a cell. Modulation of MCL-1 activity can produce a number of effects, including, e.g., promotion of apoptosis in a cell, modulation of cell cycle regulation in a cell, modulation of autophagy in a cell, modulation of cellular inflammatory responses, modulation of cellular autoimmune responses, and modulation of RNA splicing. The cross-linked polypeptides described herein can be used prophylactically or therapeutically, e.g., to treat or prevent hyperproliferative diseases, such as cancer. In certain embodiments, the polypeptides described herein can inhibit fatty acid β-oxidation to block cell growth and thus are useful for reducing or lowering fatty acid metabolism in cancer cells.

In certain instances, the stabilized peptide comprises a hydrocarbon staple. The hydrocarbon staple can be formed between two or more (e.g., 2, 3, 4, 5, 6) non-natural amino acids. There are many known non-natural or unnatural amino acids any of which may be included in the peptides of the present disclosure. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/or para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated, to name a few.

Hydrocarbon stapled polypeptides include one or more tethers (linkages) between two non-natural amino acids, which tether significantly enhances the α-helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful hydrocarbon stapled forms of that peptide, as are cross-links between X2 and X5, or between X2 and X6, or between X2 and X9, etc. The use of multiple cross-links (e.g., 2, 3, 4, or more) is also contemplated. The use of multiple cross-links is very effective at stabilizing and optimizing the peptide, especially with increasing peptide length. Thus, the disclosure encompasses the incorporation of more than one cross-link within the polypeptide sequence to either further stabilize the sequence or facilitate the structural stabilization, proteolytic resistance, acid stability, thermal stability, cellular permeability, and/or biological activity enhancement of longer polypeptide stretches. Additional description regarding making and use of hydrocarbon stapled polypeptides can be found, e.g., in U.S. Patent Publication Nos. 2012/0172285, 2010/0286057, and 2005/0250680, the contents of all of which are incorporated by reference herein in their entireties.

Stable or stabilized polypeptides are polypeptides which have been hydrocarbon stapled to maintain their natural α-helical structure, improve protease resistance, improve acid stability, improve thermal stability, improve cellular permeability, improve target binding affinity, and/or improve biological activity.

In one aspect, a SAHB polypeptide has the formula (I),

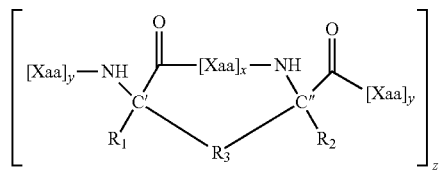

wherein:

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

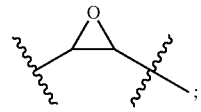

$R_6$ is H, alkyl, or a therapeutic agent;

n is an integer from 1-4;

x is an integer from 2-10;

each y is independently an integer from 0-100;

z is an integer from 1-10 (e.g., 1, 2, 3, 4, 5, 6, 7, 8, 9, 10);

and each Xaa is independently an amino acid. In some embodiments, the N-terminal [Xaa]$_y$ of formula (I) is RKALETLRRVGDG(A/V) (SEQ ID NO:64). In some embodiments, [Xaa]$_x$ is RNH. In some embodiments, the C-terminal [Xaa]$_y$ of formula (I) is TAF. The SAHB polypeptides can include an amino acid sequence described herein.

The tether can include an alkyl, alkenyl, or alkynyl moiety (e.g., $C_5$, $C_8$, or $C_{11}$ alkyl, a $C_5$, $C_8$, or $C_{11}$ alkenyl, or $C_5$, $C_8$, or $C_{11}$ alkynyl). The tethered amino acid can be alpha disubstituted (e.g., $C_1$-$C_3$ or methyl).

In some instances, x is 2, 3, or 6. In some instances, each y is independently an integer between 1 and 15, or 3 and 15. In some instances, $R_1$ and $R_2$ are each independently H or $C_1$-$C_6$ alkyl. In some instances, $R_1$ and $R_2$ are each independently $C_1$-$C_3$ alkyl. In some instances, at least one of $R_1$ and $R_2$ are methyl. For example, $R_1$ and $R_2$ can both be methyl. In some instances, $R_3$ is alkyl (e.g., $C_8$ alkyl) and x is 3. In some instances, $R_3$ is $C_{11}$ alkyl and x is 6. In some instances, $R_3$ is alkenyl (e.g., $C_8$ alkenyl) and x is 3. In some instances, x is 6 and $R_3$ is $C_{11}$ alkenyl. In some instances, $R_3$ is a straight chain alkyl, alkenyl, or alkynyl. In some instances, $R_3$ is —CH$_2$—CH$_2$—CH$_2$—CH=CH—CH$_2$—CH$_2$—CH$_2$—.

In another aspect, the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as:

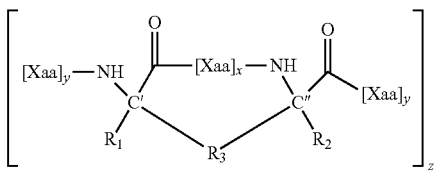

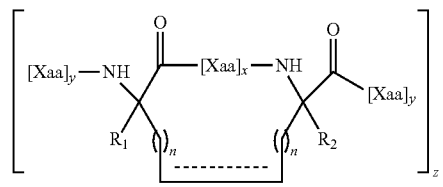

the C' and C" disubstituted stereocenters can both be in the R configuration or they can both be in the S configuration, e.g., when x is 3. When x is 6, the C' disubstituted stereocenter is in the R configuration and the C" disubstituted stereocenter is in the S configuration. The $R_3$ double bond can be in the E or Z stereochemical configuration.

In some instances, $R_3$ is $[R_4—K—R_4]_n$; and $R_4$ is a straight chain alkyl, alkenyl, or alkynyl.

In another aspect, the SAHB polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more contiguous amino acids of a BH3 domain (e.g., from MCL-1). Each $[Xaa]_y$ is a peptide that can independently comprise at least 5, 6, 7, 8, 9, 10, 11, 12, 13, 14, 15, 16, 17, 18, 19, 20, 25 or more contiguous amino acids of a BH3 domain. $[Xaa]_x$ is a peptide that can comprise 3 or 6 contiguous amino acids of acids of a BH3 domain (e.g., from MCL-1).

The SAHB polypeptide can comprise 3, 4, 5, 6, 7, 8, 9, 10, 11, 12, 13, 14, 15, 16, 17, 18, 19, 20, 25, 30, 35, 40, 45, or 50 or more contiguous amino acids of acids of a BH3 domain (e.g., from MCL-1), wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as:

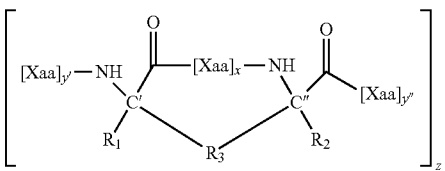

$[Xaa]_{y'}$ and $[Xaa]_{y''}$ can each comprise contiguous polypeptide sequences from the same or different BH3 domains. In some embodiments, the N-terminal $[Xaa]_{y'}$ of formula (I) is RKALETLRRVGDG(A/V) (SEQ ID NO:64). In some embodiments, $[Xaa]_x$ is RNH. In some embodiments, the C-terminal $[Xaa]_{y''}$ of formula (I) is TAF.

The disclosure features cross-linked polypeptides comprising 10 (11, 12, 13, 14, 15, 16, 17, 18, 19, 20, 21, 22, 23, 24, 25, 30, 35, 40, 45, 50 or more) contiguous amino acids of a BH3 domain, wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another aspect, the SAHB polypeptides of the invention have the formula (II), wherein:
each $R_1$ and $R_2$ are independently H, alkyl, alkenyl, alkynyl, arylalkyl, cycloalkylalkyl, heteroarylalkyl, or heterocyclylalkyl;
each n is independently an integer from 1-15;
x is 2, 3, or 6;
each y is independently an integer from 0-100;
z is an integer from 1-10 (e.g., 1, 2, 3, 4, 5, 6, 7, 8, 9, 10); and
each Xaa is independently an amino acid. In some embodiments, the N-terminal $[Xaa]_y$ of formula (I) is RKALETLRRVGDG(A/V) (SEQ ID NO:64). In some embodiments, $[Xaa]_x$ is RNH. In some embodiments, the C-terminal $[Xaa]_y$ of formula (I) is TAF.

The modified polypeptide forms an alpha-helix and can have an amino acid sequence which is 30% or more identical to an amino acid sequence disclosed herein.

In another aspect, the SAHB polypeptides of the invention have the formula (III),

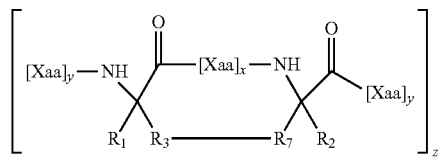

wherein:
each $R_1$ and $R_2$ are independently H, alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$ or a naturally occurring amino acid side chain; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_E$, $SO_2R_6$, $CO_2R_6$, $R_6$, a fluorescent moiety, or a radioisotope;
K is O, S, SO, $SO_2$, CO, $CO_2$, $CONR_6$, or

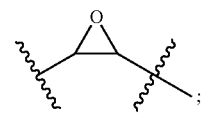 [SMILES: *C1OC1*]

$R_6$ is H, alkyl, or a therapeutic agent;
$R_7$ is alkyl, alkenyl, alkynyl; $[R_4—K—R_4]_n$ or an naturally occurring amino acid side chain; each of which is substituted with 0-6 $R_5$;
n is an integer from 1-4;
x is an integer from 2-10;
each y is independently an integer from 0-100;
z is an integer from 1-10 (e.g., 1, 2, 3, 4, 5, 6, 7, 8, 9, 10); and each Xaa is independently an amino acid. In some embodiments, the N-terminal [Xaa]$_y$ of formula (I) is RKALETLRRVGDG(A/V) (SEQ ID NO:64). In some embodiments, [Xaa]$_x$ is RNH. In some embodiments, the C-terminal [Xaa]$_y$ of formula (I) is TAF.

The polypeptide forms an alpha-helix and includes an amino acid sequence which is about 30%, about 50%, about 70%, about 80%, about 90%, about 95%, about 96%, about 97%, about 98%, or about 99% or more identical to an amino acid sequence described herein (e.g., MCL-1 SAHB$_D$ or any one of the SAHB's of SEQ ID NOs: 43-60).

While hydrocarbon tethers have been described, other tethers can also be employed in the MCL-1 BH3 peptides described herein. For example, the tether can include one or more of an ether, thioether, ester, amine, or amide, or triazole moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid. Triazole-containing (e.g., 1, 4 triazole or 1, 5 triazole) crosslinks are described in the art (e.g., in Kawamoto et al. 2012 *J. Med Chem.* 55:1137; WO 2010/060112). In addition, other methods of performing different types of stapling are well known in the art and can be employed with the MCL-1 BH3 peptides described herein (see, e.g., Lactam stapling: Shepherd et al., *J. Am. Chem. Soc.*, 127:2974-2983 (2005); UV-cycloaddition stapling: Madden et al., *Bioorg. Med. Chem. Lett.*, 21:1472-1475 (2011); Disulfide stapling: Jackson et al., *Am. Chem. Soc.*, 113:9391-9392 (1991); Oxime stapling: Haney et al., *Chem. Commun.*, 47:10915-10917 (2011); Thioether stapling: Brunel and Dawson, *Chem. Commun.*, 552-2554 (2005); Photoswitchable stapling: J. R. Kumita et al., *Proc. Natl. Acad. Sci. U.S.A*, 97:3803-3808 (2000); Double-click stapling: Lau et al., *Chem. Sci.*, 5:1804-1809 (2014); Bis-lactam stapling: J. C. Phelan et al., *J Am. Chem. Soc.*, 119:455-460 (1997); and Bis-arylation stapling: A. M. Spokoyny et al., *J Am. Chem. Soc.*, 135:5946-5949 (2013)).

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4, and i to i+7 have been described in order to provide a tether that is primarily on a single face of the alpha helix, the tethers can be synthesized to span any combinations of numbers of amino acids and also used in combination to install multiple tethers.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, e.g., those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

As will be appreciated by the skilled artisan, insights derived from those sequences that bind MCL-1 (both pan-binders and selective binders) can be used to define the essential binding residues for MCL-1 targeting. Such insights can, in turn, be used to develop optimized binders, e.g., via methods such as mutagenesis and incorporation of other non-natural amino acids.

Stabilized MCL-1 Peptide Variants

The disclosure provides MCL-1 SAHB peptides. In certain embodiments, the MCL-1 SAHB peptide binds VLCAD better than MCL-1. For example, such a peptide includes one with an amino acid sequence set forth in SEQ ID NOs.: 47, 51, 52, or 55. In certain embodiments, the MCL-1 SAHB peptide binds MCL-1 better than VLCAD. For example, such a peptide includes one with an amino acid sequence set forth in SEQ ID NOs.: 45 or 50. In other embodiments, the MCL-1 SAHB peptide binds both MCL-1 and VLCAD. For example, such a peptide includes one with an amino acid sequence set forth in SEQ ID NOs.: 19, 46, 53, or 54.

In one embodiment, the MCL-1 SAHB peptide is SAHB$_D$. In certain instances, the MCL-1 SAHB peptide has a sequence that is identical to SEQ ID NO:19, except for 1 to 6 amino acid substitutions (i.e., 1, 2, 3, 4, 5, or 6). In certain instances, the MCL-1 SAHB peptide has a sequence that is identical to any one of SEQ ID NOs: 43-60, except for 1 to 6 amino acid substitutions. In a particular embodiment, the MCL-1 SAHB peptide has a sequence that is identical to SEQ ID NO:53, except for 1 to 6 amino acid substitutions. In another particular embodiment, the MCL-1 SAHB peptide has a sequence that is identical to SEQ ID NO:55, except for 1 to 6 amino acid substitutions.

Figure 18B:
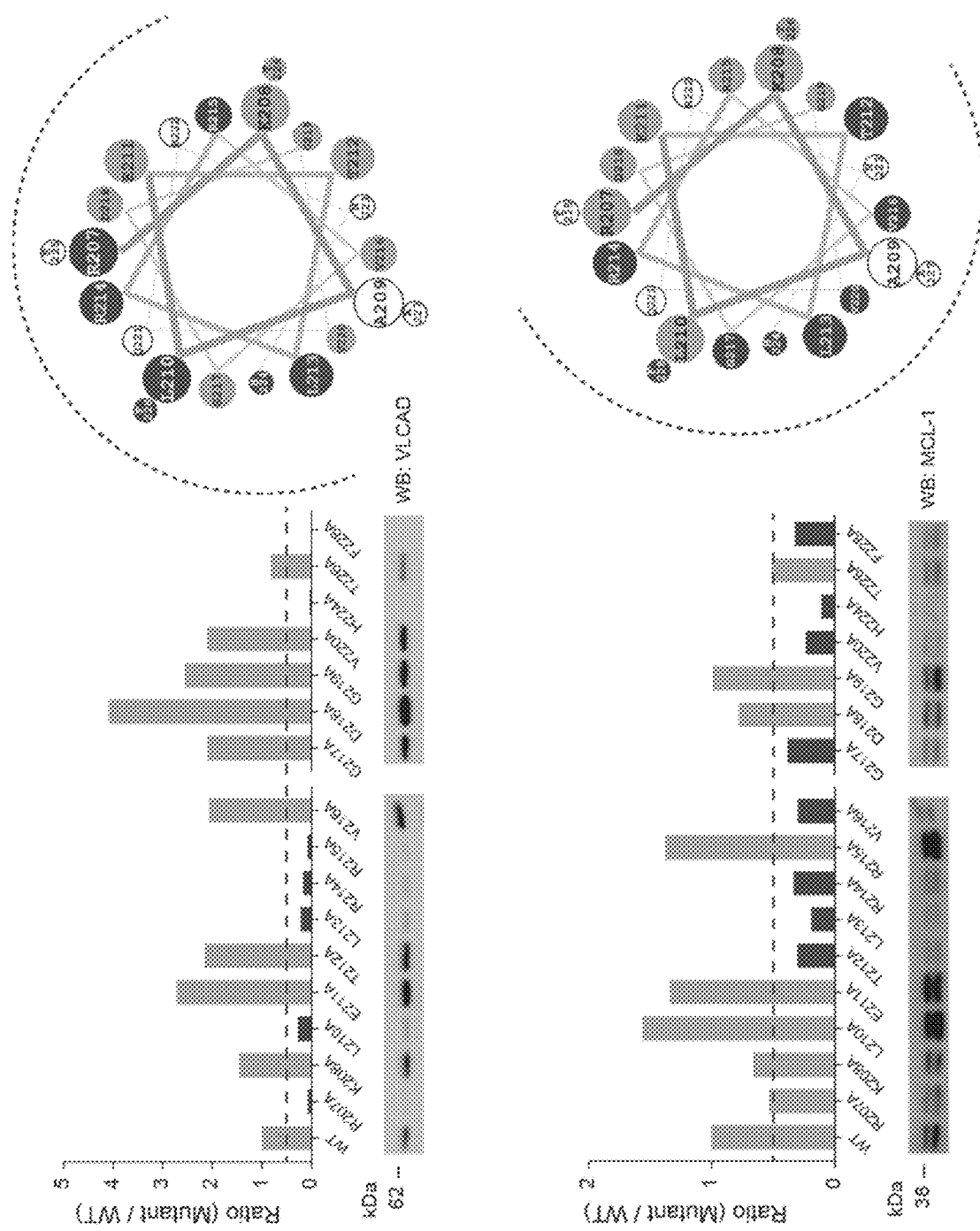
FIG. 18B provides bar graph depicting the differential influence of alanine mutagenesis on the interactions between biotinylated MCL-1 SAHB$_D$ and native VLCAD (top) or MCL-1 (bottom). The helical wheel shown to the right of the bar graphs shows the interacting face of the MCL-1 SAHB$_D$ alpha-helix (dotted curve).
Figure 19A:
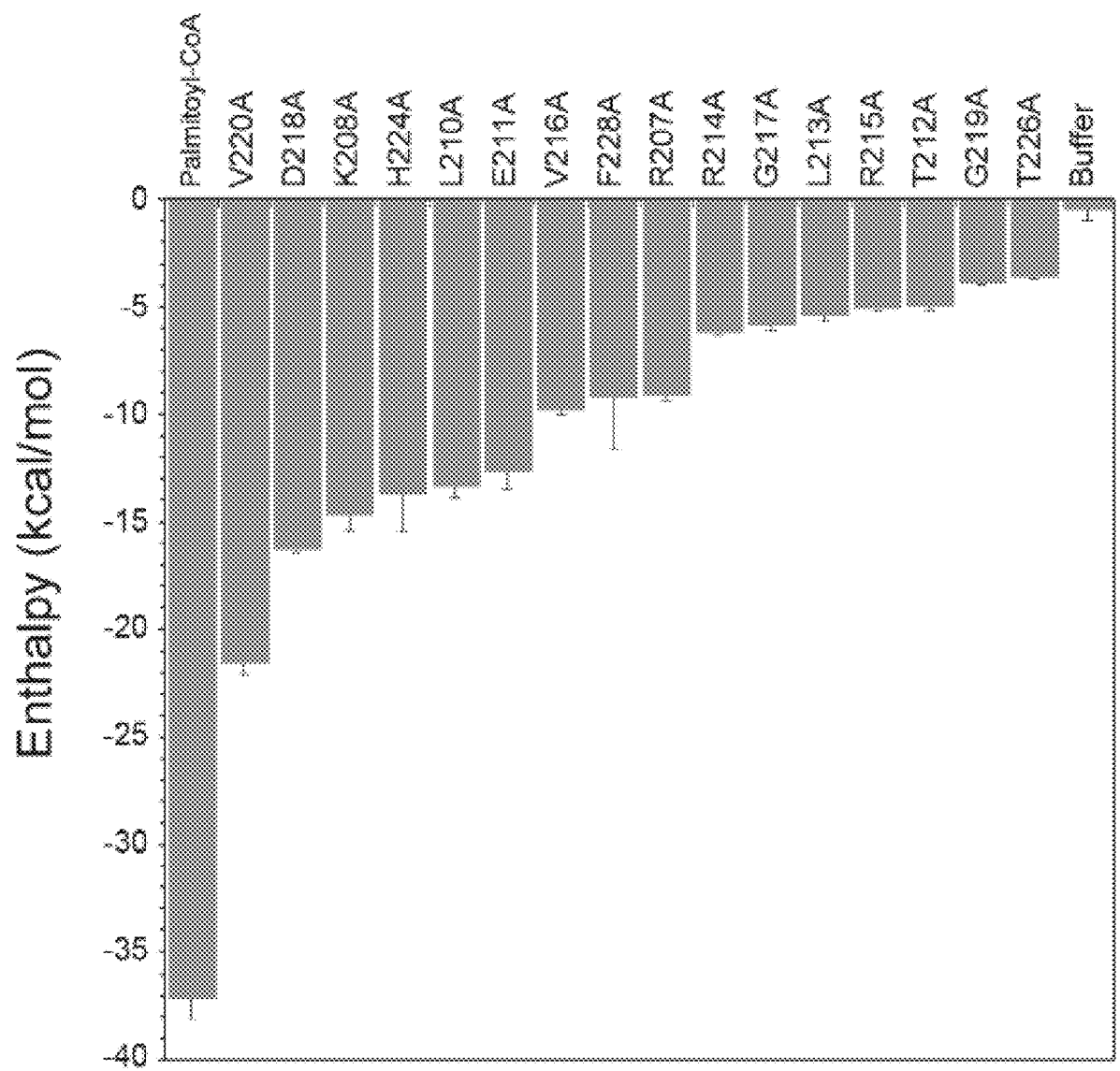
FIG. 19A is a bar graph providing the results of isothermal calorimetry binding analyses of the interactions between MCL-1 SAHB$_D$ alanine point mutants and recombinant VLCAD protein.

This disclosure provide guidance regarding where a substitution or substitutions can be made in an MCL-1 SAHB peptide (see, e.g., FIG. 18B and/or FIG. 19A). The substitutions can be based taking into account the property of the peptide (e.g., the MCL-1 peptide is a peptide that binds VLCAD but not MCL-1; or a peptide that binds both MCL-1 and VLCAD; or a peptide that binds MCL-1 but not VLCAD), and whether that property is to be maintained or altered (e.g., increased or reduced). To retain the property of an MCL-1 SAHB peptide that binds VLCAD but not MCL-1 one can choose not to introduce substitutions at positions where alanine mutations abrogated VLCAD binding (e.g., L213, R214, R215). Or if one does introduce substitutions at one or more of those sites (i.e., sites where alanine mutations abrogated VLCAD binding), introduce conservative substitutions (e.g., a hydrophobic amino acid replaced with a hydrophobic amino acid; a negatively charged amino acid replaced with a negatively charged amino acid; a positively charged amino acid replaced with a positively charged amino acid). To retain the property of an MCL-1 SAHB peptide that binds both VLCAD and MCL-1 one can choose not to introduce substitutions at positions where alanine mutations abrogated VLCAD and/or MCL-1 binding (e.g., L213, R214, R215, H224). However, if one does introduce substitutions at one or more of those sites, it is suggested that one introduce conservative amino acid substitutions.

In certain instances, the substitution(s) in the above sequences are made on the non-interacting face of the MCL-1 SAHB peptide (i.e., the face of the helix that does not interact with MCL-1 or VLCAD). In certain instances, the substitution(s) in the above sequences are made on the interacting face of the MCL-1 SAHB peptide and such substitutions are preferentially conservative substitutions, or those substitutions that do not disrupt the key molecular interactions with the binding surface. The "interacting face" of the stabilized polypeptides described herein includes those amino acid residues of the alpha helix that interact (e.g., interact specifically or bind specifically) with a MCL-1 or VLCAD protein, respectively (see, e.g., FIG. 18B). For example, the residues on MCL-1 SAHB$_D$ that are on the interacting face of the helix that interacts with VLCAD are: L213, H224, G217, L210, F228, Q221, R214, R207, E225, D218, E2111, R222, and R215 (see, FIG. 18B, top right). In certain instances, one or more of R207, L210, L213, R214, R215, H224, and F228 are not substituted in MCL-1 peptides that are required to bind VLCAD. In certain instances, if one or more of R207, L210, L213, R214, R215, H224, and F228 are substituted in MCL-1 peptides that are required to bind VLCAD, the substitutions are preferentially conservative substitutions, or those substitutions that do not disrupt the key molecular interactions with the binding surface. The residues on MCL-1 SAHB$_D$ that are on the interacting face of the helix that interacts with MCL-1 are: R214, Q221, F228, L210, G217, H224, L213, V220, A209, A227, V216, N223, and T212 (see, FIG. 18B, bottom right). In certain instances, one or more of T212, L213, R214, V216, G217, V220, H224, and F228 are not substituted in MCL-1 peptides that are required to bind MCL-1. In certain instances, if one or more of T212, L213, R214, V216, G217, V220, H224, and F228 are substituted in MCL-1 peptides that are required to bind MCL-1, the substitutions are preferentially conservative substitutions, or those substitutions that do not disrupt the key molecular interactions with the binding surface.

In certain instances, one or more (e.g., 1, 2, 3, 4, 5, 6, 7, 8) of the amino acid(s) at positions 1, 4, 7, 8, 9, 18, and/or 22 in SEQ ID NOs.:19 or 43-60 is/are not substituted. In certain instances, one or more (e.g., 1, 2, 3, 4, 5, 6, 7, 8) of the amino acid(s) at positions 7, 8, and/or 9, in SEQ ID NOs.:19 or 43-60 is/are not substituted. In certain instances, one or more (e.g., 1, 2, 3, 4, 5, 6, 7, 8) of the amino acid(s) at positions 1, 7, 8, 9, and/or 18 in SEQ ID NOs.:19 or 43-60 is/are not substituted. In some instances, the substitutions in SEQ ID NOs.:19 or 43-60 are preferentially conservative amino acid substitutions, or those substitutions that do not disrupt the key molecular interactions with the binding surface.

In one embodiment, the MCL-1 SAHB peptide has a sequence that is identical to SEQ ID NO:53, except for 1 to 6 amino acid substitutions, wherein one or more (e.g., 1, 2, 3, 4, 5, 6, 7, 8) of the amino acid(s) at positions 1, 4, 7, 8, 9, 14, 18, and/or 22 in SEQ ID NO.:53 is/are not substituted. In another embodiment, the MCL-1 SAHB peptide has a sequence that is identical to SEQ ID NO:53, except for 1 to 6 amino acid substitutions, wherein one or more (e.g., 1, 2, 3, 4, 5, 6, 7, 8) of the amino acid(s) at positions 7, 8, and/or 9 in SEQ ID NO.:53 is/are not substituted. In another embodiment, the MCL-1 SAHB peptide has a sequence that is identical to SEQ ID NO:53, except for 1 to 6 amino acid substitutions, wherein one or more (e.g., 1, 2, 3, 4, 5, 6, 7, 8) of the amino acid(s) at positions 1, 7, 8, 9, and/or 18 in SEQ ID NO.:53 is/are not substituted. In another particular embodiment, the MCL-1 SAHB peptide has a sequence that is identical to SEQ ID NO:55, except for 1 to 6 amino acid substitutions, wherein one or more (e.g., 1, 2, 3, 4, 5, 6, 7, 8) of the amino acid(s) at positions 1, 4, 7, 8, 9, 14, 18, and/or 22 in SEQ ID NO.:55 is/are not substituted. In another embodiment, the MCL-1 SAHB peptide has a sequence that is identical to SEQ ID NO:55, except for 1 to 6 amino acid substitutions, wherein one or more (e.g., 1, 2, 3, 4, 5, 6, 7, 8) of the amino acid(s) at positions 7, 8, and/or 9 in SEQ ID NO.:55 is/are not substituted. In another embodiment, the MCL-1 SAHB peptide has a sequence that is identical to SEQ ID NO:55, except for 1 to 6 amino acid substitutions, wherein one or more (e.g., 1, 2, 3, 4, 5, 6, 7, 8) of the amino acid(s) at positions 1, 7, 8, 9, and/or 18 in SEQ ID NO.:55 is/are not substituted.

In some embodiments, the MCL-1 SAHB peptide has a sequence that is identical to any one of SEQ ID NOs:43-47, 50-57, and 59. In other cases, the MCL-1 SAHB peptide has a sequence that is identical to one of SEQ ID NOs:47, 51, or 52. In some cases, the MCL-1 SAHB peptide has a sequence that is identical to SEQ ID NO: 19. In other cases, the MCL-1 SAHB peptide has a sequence that is identical to SEQ ID NO:53. In yet other cases, the MCL-1 SAHB peptide has a sequence that is identical to SEQ ID NO:55. In other cases, the MCL-1 SAHB peptide has a sequence that is identical to SEQ ID NO:45. In other cases, the MCL-1 SAHB peptide has a sequence that is identical to SEQ ID NO:50. In other cases, the MCL-1 SAHB peptide has a sequence that is identical to SEQ ID NO:46. In other cases, the MCL-1 SAHB peptide has a sequence that is identical to SEQ ID NO:54. In other cases, the MCL-1 SAHB peptide has a sequence that is identical to one of SEQ ID NOs:47, 51, or 52.

In certain cases, the SAHB is a photoreactive SAHB (pSAHB), e.g., an MCL-1 BH3 pSAHB. In some instances, the MCL-1 BH3 pSAHB comprises a benzophenone moiety. In certain cases, the pSAHB comprises the sequence of SEQ ID NO:61. In other cases, the pSAHB comprises the sequence of SEQ ID NO:62. In yet other cases, the pSAHB comprises the sequence of SEQ ID NO:63.

The disclosure also features a chimeric compound comprising a molecule described herein attached or linked to a degron (see, e.g., Winter et al., Science, 2015 Jun. 19; 348(6241):1376-81). As a non-limiting example, a chimeric compound (e.g., a compound consisting of MCL-1 SAHB$_D$ or any one of SEQ ID NOs.: 43-60 attached or linked to a degron) could bind to one or more targets (e.g., in the case of MCL-1 SAHB$_D$, MCL-1 and VLCAD), whereupon the degron moiety brings the protein to an E3 ligase for degradation. In certain embodiments, the molecule attached to the degron comprises a Bcl-2 homology 3 (BH3) domain polypeptide. In some embodiments, the BH3 domain polypeptide comprises a stapled BH3 domain polypeptide. In some embodiments, the stapled BH3 domain polypeptide comprises a MCL-1 Stabilized Alpha-Helix of BCL-2 domain (SAHB) peptide. In a particular embodiment, the MCL-1 SAHB peptide is MCL-1 SAHB$_D$.

The stabilized peptides described herein can also be combined with an anti-cancer agent (e.g., a chemotherapeutic agent; a radiotherapeutic agent, an anti-cancer antibody, a small molecule inhibitor).

Identification of Agents that Disrupt MCL-1 Binding to VLCAD or Inhibit VLCAD Activity The disclosure provides methods for using an MCL-1 domain (e.g., BH3 domain) or a mimetic thereof (e.g., stapled peptide version of an MCL-1 BH3 domain) to modulate MCL-1/VLCAD binding and/or VLCAD enzymatic activity. As described in the Examples of this disclosure, MCL-1 binds VLCAD. Thus, agents that disrupt this interaction through direct VLCAD interaction, could disrupt or impair VLCAD activity. Disrupting the MCL-1/VLCAD interaction and/or negatively affecting VLCAD enzymatic activity can be useful in treatment of hyperproliferative disorders such as cancers (especially MCL-1 expressing or MCL-1 dependent cancers or other diseases with excessive fatty acid 3-oxidation.

Agents that disrupt or impair MCL-1 binding to VLCAD can be identified using the methods described in the Examples of this application or any other method(s) known in the art. The amino acid sequences of MCL-1 proteins are shown in FIG. 1B. In certain instances, a polypeptide derived from any of those MCL-1 proteins (e.g., a BH3 domain containing fragment) or a mimetic thereof can be used to determine if it interacts with a VLCAD polypeptide or an enzymatically active fragment thereof. In certain instances, the MCL-1 BH3 polypeptide comprises or consists of the sequence: LETLRRVGDGV (SEQ ID NO: 65). In certain instances, the MCL-1 BH3 polypeptide comprises or consists of the sequence: LETLRRVGDGVQRN (SEQ ID NO: 66). In certain instances, the MCL-1 BH3 polypeptide comprises or consists of the sequence: ALETLRRVGDGVQRNHE (SEQ ID NO: 67). In certain instances, the MCL-1 BH3 polypeptide comprises or consists of the sequence: RKALETLRRVGDGVQRNHETAF (SEQ ID NO: 68). In certain instances, the MCL-1 BH3 polypeptide comprises or consists of any one of the sequences set forth in SEQ ID NOs: 65-68, except that two amino acids are replaced by non-natural amino acids with olefinic side chains that can form a hydrocarbon staple. The amino acid sequences of VLCAD proteins are provided in FIG. 7B. In one embodiment, a VLCAD polypeptide has the amino acid sequence set forth in SEQ ID NO:39. In one embodiment, a VLCAD polypeptide has the amino acid sequence set forth in SEQ ID NO:40. In one embodiment, a VLCAD polypeptide has the amino acid sequence set forth in SEQ ID NO:41. In one embodiment, a VLCAD polypeptide has the amino acid sequence set forth in SEQ ID NO:42. These methods can be used to identify agents (e.g., MCL-1 BH3 polypeptides or mimetics thereof) that inhibit the interaction between MCL-1 and VLCAD.

Agents that disrupt or impair VLCAD activity can also be identified using the methods described in the Examples of this application or any other method(s) known in the art. The amino acid sequences of VLCAD proteins are provided in FIG. 7B. Full length VLCAD polypeptides or fragments thereof that have enzymatic activity can be used to determine if an agent (e.g., MCL-1 SAHB) can inhibit VLCAD enzymatic activity.

In some instances, the MCL-1 domain that binds to and/or modulates (e.g., inhibits) VLCAD enzymatic activity is a Bcl-2 homology 3 (BH3) domain polypeptide. In certain instances, the BH3 domain polypeptide comprises a stapled BH3 domain polypeptide. For example, the stapled BH3 domain polypeptide can comprise a MCL-1 Stabilized Alpha-Helix of BCL-2 domain (SAHB) peptide. In a particular embodiment, the MCL-1 SAHB peptide is MCL-1 SAHB$_D$. In another embodiment, the MCL-1 SAHB peptide is a peptide having an amino acid sequence selected from the group consisting of SEQ ID NOs.:19 and 43-60.

Uses

MCL-1 polypeptides (e.g., BH3 domain polypeptides such as those provided in SEQ ID NOs.:19 or 43-60), or mimetics thereof that modulate VLCAD binding or enzymatic activity, can be used to treat hyperproliferative disorders (e.g., cancer). MCL-1 polypeptides (e.g., BH3 domain polypeptides such as those provided in SEQ ID NOs.:19 or 43-60), or mimetics thereof that modulate VLCAD binding or enzymatic activity, can be used to treat conditions characterized by excessive fatty acid p3-oxidation. In certain embodiments, the MCL polypeptide comprises or consists of an amino acid sequence selected from the group consisting of SEQ ID NOs.: 19, and 43-60. In one embodiment, the MCL polypeptide comprises or consists of a peptide with the amino acid sequence set forth in SEQ ID NO:19. In one embodiment, the MCL polypeptide comprises or consists of a peptide with the amino acid sequence set forth in SEQ ID NO:55. In one embodiment, the MCL polypeptide comprises or consists of a peptide with the amino acid sequence set forth in SEQ ID NO:53. In certain embodiments, the MCL polypeptide comprises or consists of at least one (e.g., 1, 2, 3) amino acid sequence selected from the group consisting of SEQ ID NOs.: 47, 51, 52, or 55. In certain embodiments, the MCL polypeptide comprises or consists of an amino acid sequence set forth in SEQ ID NO.45 or 50. In certain embodiments, the MCL polypeptide comprises or consists of an amino acid sequence set forth in SEQ ID NO.:46 or 54.

A vast number of animal models of hyperproliferative disorders, including tumorigenesis and metastatic spread, are known in the art and are disclosed herein (see, e.g., Chapter 317, "Principals of Neoplasia," in Harrison's: Principals of Internal Medicine, 13th Edition, Isselbacher et al., eds., McGraw-Hill, New York, p. 1814, and Lovejoy et al., 1997, *J Pathol.* 181:130-135). Specific examples include, e.g., for lung cancer, transplantation of tumor nodules into rats (see, e.g., Wang et al., 1997, *Ann Thorac Surg.* 64:216-219) or establishment of lung cancer metastases in SCID mice depleted of NK cells (see, e.g., Yono and Sone, 1997, Gan To Kagaku Ryoho 24:489-494); for colon cancer, e.g., colon cancer transplantation of human colon cancer cells into nude mice (see, e.g., Gutman and Fidler, 1995, *World J Surg.* 19:226-234), the cotton top tamarin model of human ulcerative colitis (see, e.g., Warren, 1996, *Aliment Pharmacol Ther. Supp* 12:45-47), and mouse models with mutations of the adenomatous polyposis tumor suppressor (see, e.g., Polakis, 1997, *Biochim Biophys Acta* 1332:F127-F147); for breast cancer, e.g., transgenic models of breast cancer (see, e.g., Dankort and Muller, 1996, *Cancer Treat Res.* 83:71-88; Amundadittir et al., 1996, *Breast Cancer Res Treat.* 39:119-135) and chemical induction of tumors in rats (see, e.g., Russo and Russo, 5 1996, *Breast Cancer Res Treat.* 39:7-20); for prostate cancer, e.g., chemically-induced and transgenic rodent models and human xenograft models (see, e.g., Royal et al., 1996, *Semin Oncol.* 23:35-40), for genitourinary cancers, e.g., induced bladder neoplasm in rats and mice (see, e.g., Oyasu, 1995, *Food Chem Toxicol.* 33:747-755) and xenografts of human transitional cell carcinomas into nude rats (see, e.g., Jarrett et al., 1995, *J Endourol.* 9:1-7); and for hematopoietic cancers, e.g., transplanted allogeneic marrow in animals (see, e.g., Appelbaum, 1997, *Leukemia* 11 (Suppl. 4):S15-S17). Further, general animal models applicable to many types of cancer have been described, including, but not limited to, the p53-deficient mouse model (see, e.g., Donehower, 1996, *Semin Cancer Biol.* 7:269-278), the Min mouse (see, e.g., Shoemaker et al., 1997, *Biochim Biophys Acta,* 1332:F25-F48), and immune responses to tumors in rat 15 (see, e.g., Frey, 1997, *Methods,* 12:173-188).

For example, a compound of the invention (e.g., a MCL-1 BH3 domain polypeptide such as a sequence set forth in any one of SEQ ID NOs.:19 or 43-60, or a mimetic thereof) can be administered to a test animal, in one aspect a test animal predisposed to develop a type of tumor, and the test animal subsequently examined for a decreased incidence of tumor formation in comparison with an animal not administered the compound. Alternatively, a compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the compound. A compound of the invention is considered effective in treating a hyperproliferative disorder when administration of a therapeutically effective amount increases time to tumor progression or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Similarly, a compound of the invention is considered effective in treating a hyperproliferative disorder when administration of a therapeutically effective amount decreases the rate of tumor growth, decreases tumor mass, decreases the number of metastases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Such results can be determined by one having ordinary skill in the relevant art, e.g., an oncologist or veterinarian.

In certain instances a variant of an MCL-1 polypeptide, e.g., a variant of the amino acid sequences shown in FIG. 1B can be employed. MCL-1 polypeptide variants refer to polypeptides that vary from a reference MCL-1 family polypeptide by the addition, deletion, and/or substitution of at least one amino acid to a natural amino acid or a non-natural amino acid or a mimetic thereof. It is known in the art that some amino acids may be changed to others with broadly similar properties without changing the nature of the activity of the polypeptide (e.g., conservative amino acid substitutions, such as glutamine for glutamate, hydrophobic for hydrophobic, and/or positively charged for positively charged) as described hereinafter. MCL-1 polypeptide variants possess at least 30% amino acid sequence identity with a reference MCL-1 BCL-2 homology domain (e.g., MCL-1 BH3 domain) within a protein or any other functional domain thereof. More specifically, polypeptide variants include, but are not limited to, an MCL-1 polypeptide comprising an active site characterized by a three dimensional structure comprising the relative structural coordinates of alpha helices 3, 4 and 5 of MCL-1 (PDB #1pqk), including residues V216, V220, H224, A227, and M231 of helix 3, residues V249, V253, and D255 of helix 4, and residues G262, R263, T266, and F270 of helix 5 or of alpha helices 3, 4, and 5 of MCL-1 (PDB #2jm6), including residues V201, H205, and M212 of helix 3, residues S226, H233, and V234 of helix 4, and residues R244, T247, L249, and F251 of helix 5, in each case, +/−a root mean square deviation from the conserved backbone atoms of those residues of not more than 1.1 angstroms, not more than 1.0 angstroms, or not more than 0.5 angstroms. MCL-1 polypeptide variants further include those polypeptides, or their biologically active fragments, that comprise an amino acid sequence which is at least 30%, 40%, 50%, 60%, 70%, 80%, 90%, 95%, 96%, 97%, 98%, 99%, or more similar to an amino acid sequence of an MCL-1 BCL-2 homology domain (e.g., BH3 domain). The BCL-2 homology domain can comprise one or more conserved amino acid residues, such as amino acid residues corresponding to L213, G217, and/or D218 of MCL-1 or conservative substitutions thereof. In certain instances, the MCL-1 polypeptide is 20-100 amino acids in length. In certain instances, the MCL-1 polypeptide is 20-80 amino acids in length. In certain instances, the MCL-1 polypeptide is 20-50 amino acids in length. In certain instances, the MCL-1 polypeptide is 20-40 amino acids in length. In certain instances, the MCL-1 polypeptide is 20-30 amino acids in length. In certain instances, the MCL-1 polypeptide is 22 amino acids in length. In certain instances, the MCL-1 polypeptide is 25 amino acids in length.

Broadly, BCL-2 family polypeptides refer to an evolutionarily conserved family of proteins having as few as one to as many as four conserved BCL-2 homology domains (BH1, BH2, BH3, and/or BH4). The BH domains are α-helical segments and are present in both the anti-apoptotic and pro-apoptotic polypeptides of BCL-2 family proteins, which are conserved across many species, both at the sequence level and functionally (e.g., mouse BCL-2 family proteins bind human MCL-1). BCL-2 family polypeptides include BCL-2, BCL-$X_L$, BCL-w, MCL-1, BCL-B, A1/BFL-1, BOO/DIVA, Nr-13, CED-9, BAX, BAK, BOK/MTD, BID, BAD, BIK/NBK, BLK, HRK, BIM/BOD, BNIP3, NIX, NOXA, PUMA, BMF, EGL-, and viral homologues. Functional BCL-2 family homology domains can also be found in non-BCL-2 family proteins, such as Beclin-1 (see, e.g., Oberstein, *J Biol Chem.* 2007) and MULE (see, e.g., Zhong, *Cell* 2005), which is a non-BCL-2 family protein that contains a BH3 domain. Exemplary methods and compositions for modulating BCL-2 family polypeptides are described, e.g., in U.S. Patent Application Ser. No. 13/133,883 and 60/995,545, the contents of which are incorporated by reference herein in their entireties.

Anti-apoptotic BCL-2 polypeptides are those BCL-2 family polypeptides characterized by having one or more amino acid homology domains, BH1, BH2, BH3, and/or BH4, and that promote cell survival by attenuating or inhibiting apoptosis. Anti-apoptotic BCL-2 polypeptides can further include those proteins, or their biologically active fragments, that are at least 30%, 40%, 50%, 60%, 70%, 80%, 90%, 95%, 96%, 97%, 98%, 99%, or more similar in amino acid sequence to an anti-apoptotic BCL-2 homology domain within a BCL-2 family polypeptide. The BCL-2 homology domain can comprise one or more conserved amino acid residue, such as amino acid residues corresponding to residues L213, G217, and/or D218 of MCL-1's BH3 domain (PDB #1pqk). Anti-apoptotic BCL-2 polypeptides include MCL-1, BCL-2, BCL-$X_L$, BCL-w, BCL-B, A1/BFL-1, BOO/DIVA, Nr-13, CED-9, and viral homologues.

"BH3 SAHB" refers to the BCL-2 homology domain 3 of a BCL-2 family polypeptide and/or a BH3 domain-containing polypeptide (e.g., MCL-1) that has been hydrocarbon stapled so as to form a stabilized α-helix. The amino acid sequences of numerous BH3 domains are described herein and in the art; likewise, methods of making BH3 SAHBs are known in the art. See, e.g., U.S. Patent Publication Nos. 2012/0172285 and 2005/0250680, which are herein incorporated by reference in their entireties. Non-limiting examples include the amino acid sequences set forth in any one of SEQ ID NOs.:19 or 43-60.

Inhibition (e.g., by a MCL-1 SAHB such as a sequence set forth in any one of SEQ ID NOs.:19 or 43-60) generally refers to a decrease or blocking of one or more activities (e.g., binding to a physiological ligand) of a BCL-2 family polypeptide, or other defined biochemical activity based upon protein-protein interaction (e.g., inhibition of VLCAD enzymatic activity). For example, a compound that inhibits a pro-apoptotic activity can bind to an active site of a BCL-2 family polypeptide and prevent activation or reduce the activity of the BCL-2 family polypeptide. Thus, the compound will inhibit or decrease the effects of a pro-apoptotic activity. Likewise, a compound that inhibits a protein-protein interaction can prevent or reduce the binding of a BCL-2 family polypeptide to one or more physiological ligands (e.g., inhibition of MCL-1/VLCAD interaction). Inhibition can be partial or complete; e.g., a compound can reduce the binding of a BCL-2 family polypeptide to one or more physiological ligands by 10%, 20%, 30%, 40%, 50%, 60%, 70%, 80%, 90%, 95%, 96%, 97%, 98%, 99%, or more compared to when the compound is not present.

One or more MCL-1 agents that inhibit the MCL-1/VLCAD interaction or VLCAD activity (e.g., a MCL-1 BH3 polypeptide or a mimetic thereof) can be administered to a subject at, e.g., a dose below that which would directly (as opposed to indirectly) inhibit the canonical anti-apoptotic function of MCL-1 at the mitochondria. Such a concentration can nevertheless be sufficient to partially or completely inhibit the MCL-1/VLCAD interaction or VLCAD activity or the capacity of MCL-1 to exert its VLCAD-modulatory activity. The concentration of the MCL-1 agent that inhibits the MCL-1/VLCAD interaction or VLCAD activity (e.g., a MCL-1 SAHB such as MCL-1 SAHB$_D$ or a sequence set forth in any one of SEQ ID NOs.:43-60) or the capacity of MCL-1 to exert its VLCAD-modulatory activity administered to a subject can be, e.g., a concentration less than about, 1000, 750, 500, 250, 200, 100, 75, 50, 40, 30, 25, 20, 19, 18, 17, 16, 15, 14, 13, 12, 11, 10, 9, 8, 7, 6, 5, 4, 3, 2, or 1 µM or less, or any dose where apoptosis of cancer cells or hyperproliferative cells is not necessarily or exclusively triggered by blocking the canonical anti-apoptotic functionality of MCL-1. In certain aspects, this concentration is 10-20 µM (e.g., of MCL-1 SAHB$_D$ or a sequence set forth in any one of SEQ ID NOs.:43-60). In certain aspects, this concentration is 5-20 µM (e.g., of MCL-1 SAHB$_D$ or a sequence set forth in any one of SEQ ID NOs.:43-60). In other aspects, the sub-apoptotic concentration is 1-10 µM (e.g., of MCL-1 SAHB$_D$ or a sequence set forth in any one of SEQ ID NOs.:43-60). In yet other aspects, the sub-apoptotic concentration is 5-15 µM (e.g., of MCL-1 SAHB$_D$ or a sequence set forth in any one of SEQ ID NOs.:43-60). In yet other aspects, the sub-apoptotic concentration is 5-50 µM (e.g., of MCL-1 SAHB$_D$ or a sequence set forth in any one of SEQ ID NOs.:43-60). In yet other aspects, the sub-apoptotic concentration is 5-100 µM (e.g., of MCL-1 SAHB$_D$ or a sequence set forth in any one of SEQ ID NOs.:43-60).

In some instances, one or more MCL-1 agents that inhibit the MCL-1/VLCAD interaction or VLCAD activity (e.g., a MCL-1 BH3 polypeptide or a mimetic thereof) have a specific point mutation that abrogates the direct (as opposed to indirect) inhibition of the canonical anti-apoptotic function of MCL-1 at the mitochondria. MCL-1 agents bearing such mutants may thus be exclusive binders of VLCAD, or even show enhanced binding to VLCAD, compared to no binding activity toward the canonical anti-apoptotic function of MCL-1 at the mitochondria.

Inhibitors can include small molecules, which refer to chemical compounds having a molecular weight below 2,000 daltons, between 300 and 1,000 daltons, or between 400 and 700 daltons. Such small molecules can be organic molecules.

MCL-1 associated disorders are disorders associated with a deregulated MCL-1 polypeptide, particularly increased expression of MCL-1. An MCL-1 associated disorder is characterized by having at least a 10%, 20%, 30%, 40%, 50%, 60%, 70%, 80%, 90%, or more increase in the level of MCL-1 expression as compared to a normal control cell, preferably from the same subject and tissue type. MCL-1 associated disorders are associated with excessive cellular survival and/or proliferation, e.g., cancer. An MCL-1 associated disorder need not be diagnosed by identification of deregulated MCL-1. Instead, the disorder can initially be diagnosed by typical methods known in the art, e.g., imaging studies, physical examination, biopsy, blood analysis, and confirmed to be an MCL-1 associated disorder by histological analysis, PCR, or other methods known in the art. MCL-1 associated disorders include those described herein.

Hyperproliferative disorders include cancer, neoplastic growth, hyperplastic or proliferative growth, and/or a pathological state of abnormal cellular development or survival. Such disorders include, e.g., solid tumors, non-solid tumors, and any abnormal cellular proliferation or accumulation, such as that seen in leukemia. Such disorders also include, e.g., cellular proliferation, growth, differentiation, or migration disorders and diseases or disorders where there is decreased apoptosis or cell death. Thus, hyperproliferative disorders include, e.g., cancer, e.g., carcinoma, sarcoma, lymphoma, or leukemia, examples of which include, but are not limited to, ovarian, lung, breast, endometrial, uterine, hepatic, gastrointestinal, prostate, colorectal, liver, and brain cancer; tumor angiogenesis and metastasis; skeletal dysplasia; and hematopoietic and/or myeloproliferative disorders. Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, and Kaposi sarcoma.

Further examples of proliferative disorders include hematopoietic neoplastic disorders. Such disorders involve hyperplastic/neoplastic cells of hematopoietic origin, e.g., arising from myeloid, lymphoid or erythroid lineages, or precursor cells thereof. For example, the diseases can arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stromal tumors such as, granulosa-theca cell tumors, thecomafibromas, androblastomas, hill cell tumors, and gonadoblastoma; and metastatic tumors such as Krukenberg tumors.

Many anticancer agents and drugs are known in the art. Such agents and drugs include, e.g., chemotherapeutic compounds and/or molecular therapeutic compounds, antisense therapies, antibody therapies, peptide therapies, nucleic acid therapies (e.g., RNAi), radiation therapies, or combinations thereof, used in the treatment of hyperproliferative diseases such as cancer.

Refractory cancer refers to cancers which have not achieved complete remission after a first course of chemotherapy, or which have failed to achieve complete or partial remission on subsequent chemotherapy. Relapsed cancer refers to cancers which have recurred following prior complete or partial remission in response to a prior treatment. Recurrence can be defined in any way, including a reappearance or re-growth of a tumor as detected by clinical, radiological, or biochemical assays, or by an increased level of a cancer marker. Prior treatments can include, but are not limited to, chemotherapy, radiation therapy, and bone marrow transplantation.

In one aspect, the compounds of the invention are administered to a human subject as monotherapy for the prevention, treatment, and/or management of cancer. The disclosure includes a method of preventing, treating, and/or managing cancer in a patient (e.g., a human patient), the method comprising administering to the patient a prophylactically effective regimen or a therapeutically effective regimen, the regimen comprising administering to the patient a compound of the invention or a composition of the invention, wherein the patient has been diagnosed with cancer. The amount of a compound of the invention used in the prophylactic and/or therapeutic regimens which will be effective in the prevention, treatment, and/or management of cancer can be based on the currently prescribed dosage of the compound as well as assessed by methods disclosed herein.

In another aspect, the patient has received or is receiving another therapy. In another aspect, the patient has not previously received a therapy for the prevention, treatment, and/or management of the cancer.

Another aspect of the invention relates to a method of preventing, treating, and/or managing cancer, the method comprising administering to a patient in need thereof a prophylactically effective regimen or a therapeutically effective regimen, the regimen comprising administering to the patient a compound of the invention (as described above), or a pharmaceutically acceptable salt thereof wherein the patient received another therapy. In some embodiments, the prior therapy is, for example, chemotherapy, radioimmunotherapy, toxin therapy, prodrug-activating enzyme therapy, antibody therapy, surgical therapy, immunotherapy, radiation therapy, targeted therapy or any combination thereof.

In some aspects, the prior therapy has failed in the patient. In some aspects, the therapeutically effective regimen comprising administration of a compound of the invention is administered to the patient immediately after patient has undergone the prior therapy. For instance, in certain aspects, the outcome of the prior therapy may be unknown before the patient is administered a compound of the invention.

In certain aspects, the regimens comprise administering a prophylactically effective regimen and/or a therapeutically effective regimen, wherein the regimen results in a reduction in the cancer cell population in the patient. In one aspect, the patient undergoing the regimen is monitored to determine whether the regimen has resulted in a reduction in the cancer cell population in the patient.

Typically, the monitoring of the cancer cell population is conducted by detecting the number or amount of cancer cells in a specimen extracted from the patient. Methods of detecting the number or amount of cancer cells in a specimen are known in the art. This monitoring step is typically performed at least 1, 2, 4, 6, 8, 10, 12, 14, 15, 16, 18, 20, or 30 days after the patient begins receiving the regimen.

In some aspects, the specimen may be a blood specimen, wherein the number or amount of cancer cells per unit of volume (e.g., 1 mL) or other measured unit (e.g., per unit field in the case of a histological analysis) is quantitated. The cancer cell population, in certain embodiments, can be determined as a percentage of the total blood cells.

In other aspects, the specimen extracted from the patient is a tissue specimen (e.g., a biopsy extracted from suspected cancerous tissue), where the number or amount of cancer cells can be measured, e.g., on the basis of the number or amount of cancer cells per unit weight of the tissue.

The number or amount of cancer cells in the extracted specimen can be compared with the numbers or amounts of cancer cells measured in reference samples to assess the efficacy of the regimen and amelioration of the cancer under therapy. In one aspect, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another aspect, the reference sample is extracted from a healthy, non-cancer-afflicted patient.

In other aspects, the cancer cell population in the extracted specimen can be compared with a predetermined reference range. In a specific aspect, the predetermined reference range is based on the number or amount of cancer cells obtained from a population(s) of patients suffering from the same type of cancer as the patient undergoing the therapy.

If the reduction in the cancer cell population is judged too small upon comparing the number, amount, or percentage of cancer cells in the specimen extracted from the patients undergoing therapy with the reference specimen, then the medical practitioner has a number of options to adjust the therapeutic regimen. For instance, the medical practitioner can then either increase the dosage of the compound or composition of the invention administered, the frequency of the administration, the duration of administration, or any combination thereof. In a specific embodiment, after the determination is made, a second effective amount of a compound or composition of the invention can be administered to the patient.

In an aspect, the regimens comprise administering a compound or composition of the invention, wherein the regimen results in a reduction in the number, amount, or percentage of cancer cells and a reduction in the number, amount, or percentage of cancer cells in the patient.

The amount of a compound of the invention used in the prophylactic and/or therapeutic regimens which will be effective in the prevention, treatment, and/or management of cancer can be based on the currently prescribed dosage of the compound as well as assessed by methods disclosed herein and known in the art. The frequency and dosage will vary also according to factors specific for each patient depending on the specific compounds administered, the severity of the cancerous condition, the route of administration, as well as age, body, weight, response, and the past medical history of the patient. For example, the dosage of a compound of the invention which will be effective in the treatment, prevention, and/or management of cancer can be determined by administering the compound to an animal model such as, e.g., the animal models disclosed herein or known to those skilled in the art. In addition, in vitro assays may optionally be employed to help identify optimal dosage ranges.

In some aspects, the prophylactic and/or therapeutic regimens comprise titrating the dosages administered to the patient so as to achieve a specified measure of therapeutic efficacy. Such measures include a reduction in the cancer cell population in the patient.

In certain aspects, the dosage of the compound of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one aspect, the reference sample is a specimen extracted from the same patient, prior to receiving the prophylactic and/or therapeutic regimen. In specific embodiments, the number or amount of cancer cells in the test specimen is at least 2%, 5%, 10%, 15%, 20%, 30%, 40%, 50%, 60%, 70%, 80%, 90%, 95% or 99% lower than in the reference sample.

In some aspects, the dosage of the compound of the invention in the prophylactic and/or therapeutic regimen is adjusted so as to achieve a number or amount of cancer cells that falls within a predetermined reference range. In these aspects, the number or amount of cancer cells in a test specimen is compared with a predetermined reference range.

In other aspects, the dosage of the compound of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, non-cancer-afflicted patient. In specific aspects, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these embodiments, the dosage of the compounds of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., mg/m$^2$) to provide an equivalent human dose.

The prophylactic and/or therapeutic regimens disclosed herein comprise administration of compounds of the invention or pharmaceutical compositions thereof to the patient in a single dose or in multiple doses (e.g., 1, 2, 3, 4, 5, 6, 7, 8, 10, 15, 20, or more doses).

In one aspect, the prophylactic and/or therapeutic regimens comprise administration of the compounds of the invention or pharmaceutical compositions thereof in multiple doses. When administered in multiple doses, the compounds or pharmaceutical compositions are administered with a frequency and in an amount sufficient to prevent, treat, and/or manage the condition. In an aspect, the frequency of administration ranges from once a day up to about once every eight weeks. In an aspect, the frequency of administration ranges from about once a week up to about once every six weeks. In an aspect, the frequency of administration ranges from about once every three weeks up to about once every four weeks.

In some aspects, the prophylactic and/or therapeutic regimen comprises administration of a compound of the invention in combination with one or more additional anticancer therapeutics. Preferably, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., *Goodman & Gilman's The Pharmacological Basis Of Basis Of Therapeutics*, 10th ed., Mc-Graw-Hill, New York, 2001; *Physician's Desk Reference* (60th ed., 2006).

The compounds of the invention and the one or more additional anticancer therapeutics can be administered separately, simultaneously, or sequentially. In various aspects, the compound of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In some aspects, two or more anticancer therapeutics are administered within the same patient visit.

In certain aspects, the compound of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies.

In an aspect, the anticancer therapeutics are administered concurrently to a subject in separate compositions. The combination anticancer therapeutics of the invention may be administered to a subject by the same or different routes of administration.

In a specific aspect, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Compositions

The present disclosure provides compositions that are suitable for veterinary and/or human administration (e.g., pharmaceutical compositions). In certain embodiments, the pharmaceutical composition comprises at least one (e.g., 1, 2, 3) amino acid sequence selected from the group consisting of SEQ ID NOs.: 19, and 43-60. In one embodiment, the pharmaceutical composition comprises a peptide with the amino acid sequence set forth in SEQ ID NO:19. In one embodiment, the pharmaceutical composition comprises a peptide with the amino acid sequence set forth in SEQ ID NO:55. In one embodiment, the pharmaceutical composition comprises a peptide with the amino acid sequence set forth in SEQ ID NO:53. In certain embodiments, the pharmaceutical composition comprises at least one (e.g., 1, 2, 3) amino acid sequence selected from the group consisting of SEQ ID NOs.: 47, 51, 52, or 55. In certain embodiments, the pharmaceutical composition comprises an amino acid sequence set forth in SEQ ID NO.:45 or 50. In certain embodiments, the pharmaceutical composition comprises an amino acid sequence set forth in SEQ ID NO.:46 or 54. The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., more preferably a mammal, most preferably a human.

The formulation of a compound of the invention used in the prophylactic and/or therapeutic regimens which will be effective in the prevention, treatment, and/or management of cancer can be based on the currently available formulation. Alternatively, the compounds can be reformulated based on knowledge within the art and the teachings herein. For example, the compound may be in the form of a solid, liquid or gas (aerosol). Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow a compound of the invention to be bioavailable upon administration of the composition to a subject. Compositions can take the form of one or more dosage units, where, for example, a tablet can be a single dosage unit, and a container of a compound of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the compound of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid or topical cream. In addition, the carrier(s) can be gaseous, so as to provide an aerosol composition useful in, e.g., inhalatory administration.

The term "carrier" refers to a diluent, adjuvant or excipient, with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the compounds of the invention and pharmaceutically acceptable carriers are sterile. Water is a preferred carrier when the compound of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin, or a fatty oil.

The pharmaceutical composition can be in the form of a liquid, e.g., an elixir, syrup, solution, emulsion, or suspension. The liquid can be useful for oral administration, topical administration, or delivery by injection. When intended for oral administration, a composition can comprise one or more of a sweetening agent, preservative, dye or colorant, and flavor enhancer. In a composition for administration by injection, one or more of a surfactant, preservative, wetting agent, dispersing agent, suspending agent, buffer, stabilizer, and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions comprise an effective amount of a compound of the invention such that a suitable dosage will be obtained. The pharmaceutical compositions may comprise the known effective amount of the compounds as currently prescribed for their respective disorders.

Typically, the effective amount is at least 0.01% of a compound of the invention by weight of the composition. When intended for oral administration, this amount can be varied to be between 0.1% and 80% by weight of the composition. Preferred oral compositions can comprise from between 4% and 50% of the compound of the invention by weight of the composition. Preferred compositions of the present invention are prepared so that a parenteral dosage unit contains from between 0.01% and 2% by weight of the compound of the invention.

The compounds of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a compound of the invention. In certain embodiments, more than one compound of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a pre-cancerous condition).

In specific aspects, it can be desirable to administer one or more compounds of the invention locally to the area in need of treatment (e.g., location of the tumor or ischemic condition). This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as silastic membranes, or fibers. In one aspect, administration can be by direct injection at the site (or former site) of a cancer, tumor, or precancerous tissue.

Pulmonary administration can also be employed, e.g., by use of an inhaler or nebulizer, and formulation with an aerosolizing agent, or via perfusion in a fluorocarbon or synthetic pulmonary surfactant. In certain aspects, the compounds of the invention can be formulated as a suppository, with traditional binders and carriers such as triglycerides.

In yet another aspect, the compounds of the invention can be delivered in a controlled release system. In one aspect, a pump can be used (see, e.g., Sefton, *CRC Crit Ref Biomed Eng.* 1987, 14, 201; Buchwald et al., *Surgery* 1980, 88: 507; Saudek et al., *N Engl J Med.* 1989, 321: 574). In another aspect, polymeric materials can be used (see, e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, *J Macromol Sci Rev Macromol Chem.* 1983, 23, 61; see also Levy et al., *Science* 1985, 228, 190; During et al., *Ann Neurol.*, 1989, 25, 351; Howard et al., *J Neurosurg.*, 1989, 71, 105). In yet another aspect, a controlled-release system can be placed in proximity of the target of the compounds of the invention, e.g., the brain, thus requiring only a fraction of the systemic dose (see, e.g., Goodson, in Medical Applications of Controlled Release, supra, vol. 2, 1984, pp. 115-138). Other controlled-release systems discussed in the review by Langer (*Science* 1990, 249, 1527-1533) can be used.

In another aspect, polymeric materials can be used to achieve controlled or sustained release of the compounds of the invention (see, e.g., U.S. Pat. Nos. 5,679,377; 5,916,597; 5,912,015; 5,989,463; 5,128,326; PCT Publication No. WO 99/15154; and PCT Publication No. WO 99/20253, all of which are hereby incorporated by reference in their entireties). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a preferred aspect, the polymer used in a sustained release formulation is inert, free of leachable impurities, stable on storage, sterile, and biodegradable.

Whether in solid, liquid or gaseous form, the compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance, in a particular aspect, the pharmaceutical composition comprises a compound of the invention, an additional anticancer agent, and a pharmaceutically acceptable carrier or vehicle.

The disclosure also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In addition, optionally associated with such kit or pharmaceutical pack will be instructions for use of such kit or pack.

Screening Methods

The disclosure also provides methods for identifying agents that inhibit the interaction between MCL-1 and VLCAD. A test compound can be used to contact a mixture or composition comprising an MCL-1 polypeptide and a VLCAD polypeptide. If the test compound is able to inhibit the interaction between MCL-1 and VLCAD then it is identified as being useful for inhibiting fatty acid β-oxidation to block cell growth in the context of conditions of cellular hyperproliferation (e.g., cancer). In some instances, the test compound is identified as being useful for treating an MCL-1 expressing cancer.

The disclosure also provides methods for identifying agents that inhibit the enzymatic activity of VLCAD. A test compound can be used to contact a composition comprising a VLCAD polypeptide under conditions that enable the assessment the enzymatic activity of VLCAD. If the test compound is able to inhibit the enzymatic activity of VLCAD then it is identified as being useful for inhibiting fatty acid β-oxidation to block cell growth in the context of conditions of cellular hyperproliferation (e.g., cancer). In some instances, the test compound is identified as being useful for treating an MCL-1 expressing cancer.

In the above methods, the MCL-1 polypeptide can be any one of the polypeptides of FIG. 1B or a BH3 domain-containing fragment thereof. In certain instances, the MCL-1 polypeptide comprises or consists of the BH3 domain of MCL-1. In certain instances, the MCL-1 polypeptide comprises or consists of any one of the sequences set forth in SEQ ID NOs.: 65-67. In the above methods, the VLCAD polypeptide can be any one of the polypeptides of FIG. 7B or an enzymatically active fragment thereof. The test compound can be e.g., a small molecule or polypeptide. In certain instances, the test compound is a SAHB. In one embodiment, the test compound is a BH3 SAHB. In one embodiment, the test compound is a MCL-1 BH3 SAHB. In one embodiment, the test compound is a MCL-1 BH3 SAHB that is identical to any one of SEQ ID NOs:19, 53 or 55, except for 1 to 6 (e.g., 1, 2, 3, 4, 5, or 6) amino acid substitutions.

The following are examples of the practice of the invention. They are not to be construed as limiting the scope of the invention in any way.

EXAMPLES

Example 1: MCL-1 BH3 Helix is a Protein-Interacting Ligand

To understand the molecular basis for MCL-1 specificity, an anti-apoptotic protein binding screen was conducted of all natural BH3 domain sequences bearing an installed all-hydrocarbon staple to reinforce the bioactive alpha-helical structure. Ironically, only the BH3 helix of MCL-1 itself was an exclusive MCL-1 binder (see, e.g., Stewart, *Nat Chem Biol.*, 6(6):595-601 (2010)). The crystal structure of the MCL-1 SAHB$_D$/MCL-1ΔNΔC complex indicated that the hydrophobic surface of MCL-1 BH3 directly engages the canonical BH3-binding groove of MCL-1ΔNΔC. Thus, in addition to serving as a structural component of the MCL-1 groove, the MCL-1 BH3 helix, upon exposure, can potentially also function as a protein-interacting ligand.

Example 2: VLCAD is an MCL-1 BH3 Interactor

Figure 4A:
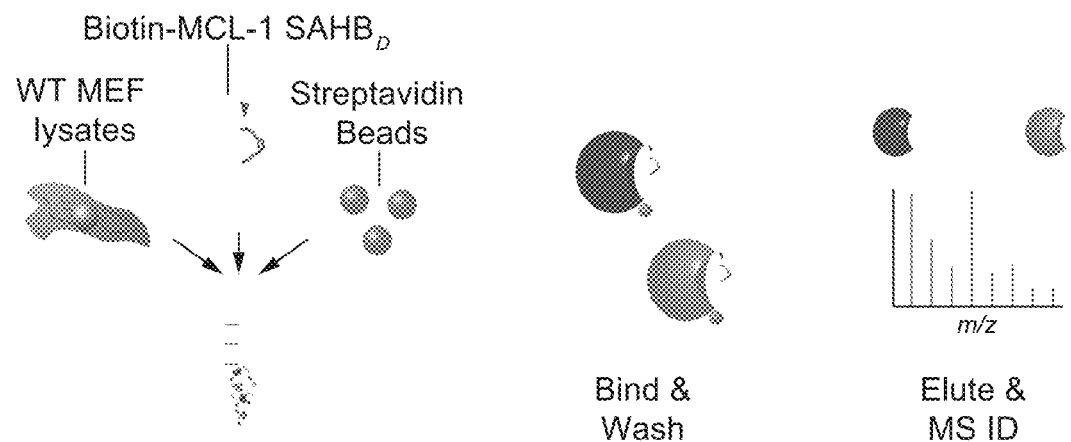
FIG. 4A is a schematic showing the protein capture workflow using biotinylated SAHB, wild-type MEF lysates, and streptavidin pulldown, followed by washing, elution, and mass spectrometry (MS)-based protein identification.
Figure 4B:
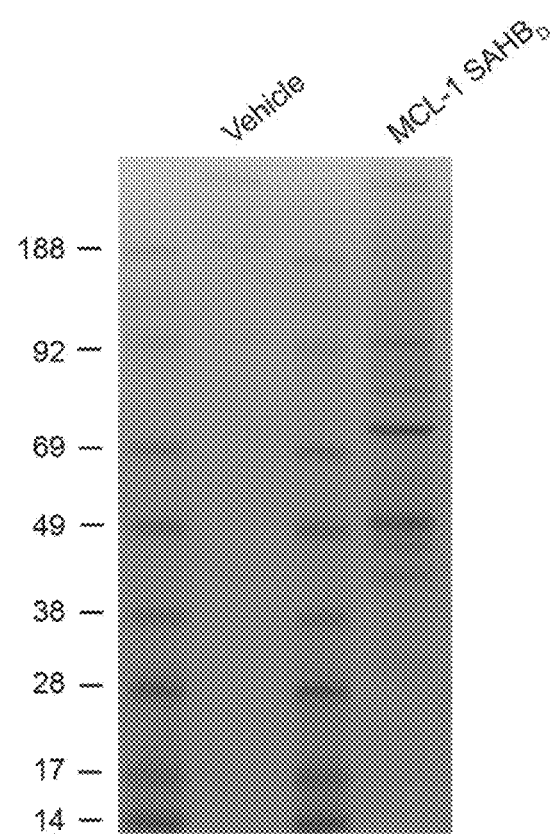
FIG. 4B is a Coomassie stained gel showing that MCL-1 SAHB$_D$ pulls down significantly more proteins from MEF lysates than the vehicle control.
Figure 5:
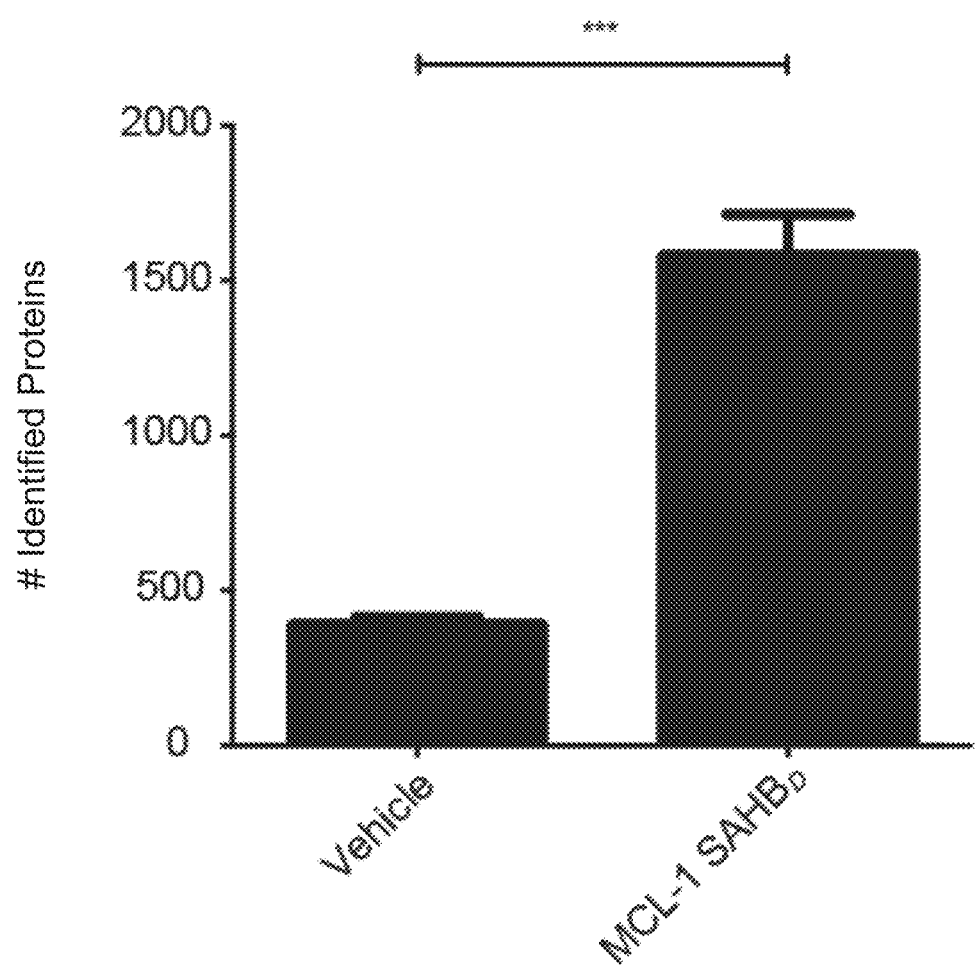
FIG. 5 is a bar graph showing the number of MS-identified proteins in eluates from vehicle and MCL-1 SAHB$_D$ pulldowns.
Figure 6:
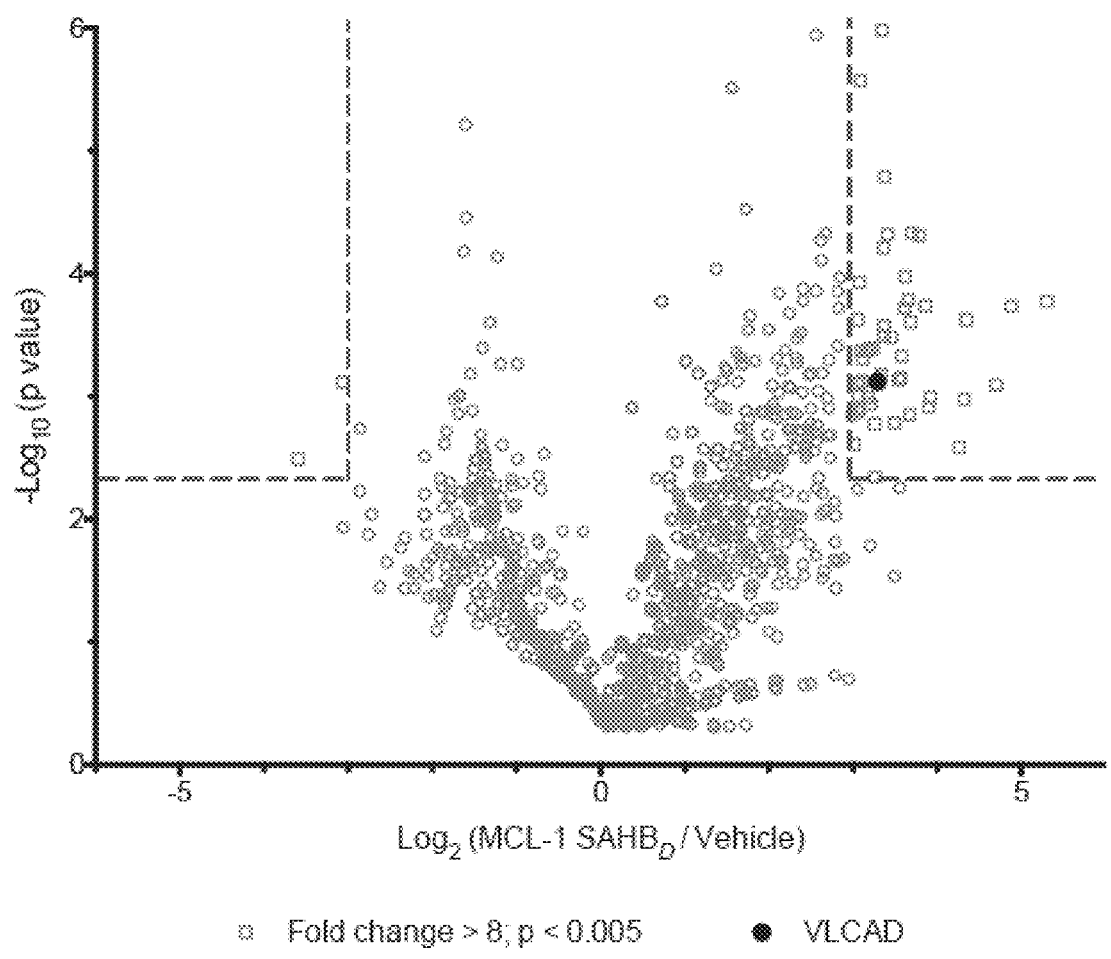
FIG. 6 is a Volcano plot showing MEF proteins that were significantly enriched in MCL-1 SAHB$_D$ pulldowns as compared to vehicle control. Interactor specificity thresholds were set at fold change >8 and p<0.005.

An exploratory proteomics analysis was conducted to identify proteins that interact with the MCL-1 BH3 domain helix. An extensive library of MCL-1 stapled BH3 peptides (FIG. 2) was generated to both identify novel protein interactors by mass spectrometry and then deploy the stapled peptide constructs as novel probes to dissect and pharmacologically modulate the identified protein interactors and associated signaling pathways. As an example, an N-terminally biotinylated stapled peptide designed based on the sequence of MCL-1's BH3 domain (Btn-MCL-1 SAHB$_D$), or vehicle, was incubated with wild-type mouse embryonic fibroblast (MEF) lysates, followed by high stringency streptavidin capture. To validate the proteomics workflow and ensure that Btn-MCL-1 SAHB$_D$ could, in fact, engage protein interactors in a lysate, eluates were first run on a gel for anti-MCL-1 Western analysis. Endogenous MCL-1 protein from MEFs was readily identified in the eluates but not in the vehicle pulldown, indicating that MCL-1 SAHB$_D$ pulldowns could robustly and specifically be used to identify interactors (FIG. 3). For mass spectrometry (MS) analysis, eluates were run on a reducing/denaturing gel followed by Coomassie staining (FIG. 4) and in-gel digestion was performed before injection on the instrument. MS identification of proteins in eluates showed an enrichment of proteins in the MCL-1 SAHB$_D$ pulldown versus vehicle control (FIG. 5). Fold enrichment in MCL-1 SAHB$_D$ versus vehicle, and p-value analysis of the MS data over three biological replicates, identified high-confidence MCL-1 BH3 interactors (FIG. 6) (dots). In particular, VLCAD was repeatedly identified as a high stringency interactor (FIG. 6 (black dot) and FIGS. 7A and 7B).

Example 3: The VLCAD/MCL-1 Stapled Peptide Interaction is Selective and Direct

Figure 8:
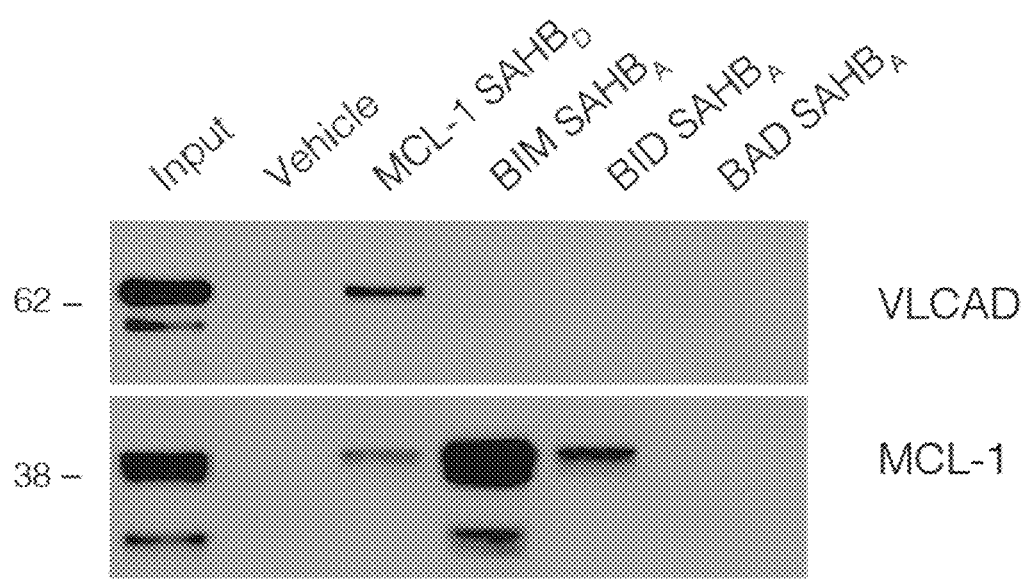
FIG. 8 is a pulldown assay showing that MCL-1 SAHB$_D$ can directly bind to and pull down VLCAD from cellular lysates, in addition to MCL-1, whereas other BH3 SAHBs obey the physiologic pattern of MCL-1 (i.e., BIM and BID yes, BAD no), but do not engage VLCAD.
Figure 9:
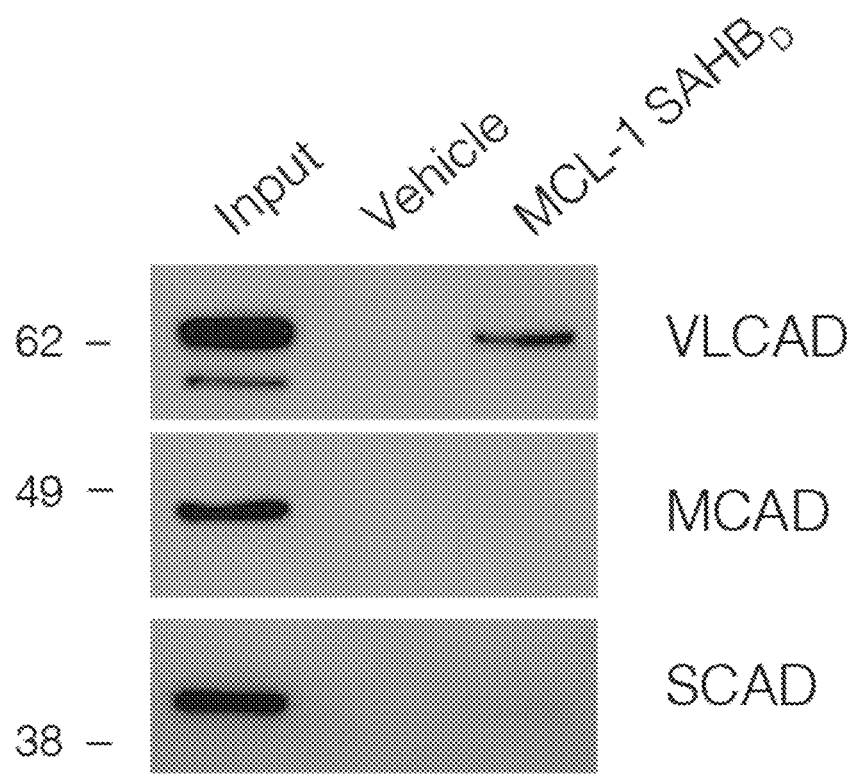
FIG. 9 is a pulldown assay showing that MCL-1 SAHB$_D$ specifically binds VLCAD, but not the other related enzymes that process smaller sized fatty acids, MCAD and SCAD.
Figure 10:
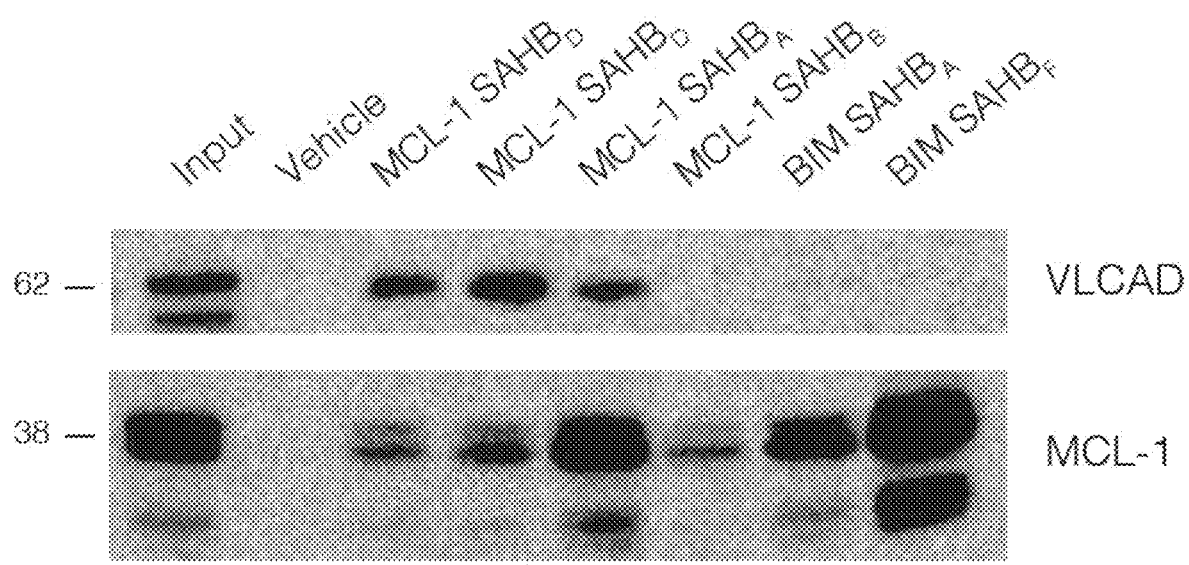
FIG. 10 is a pulldown assay showing that the MCL-1 SAHB/VLCAD interaction is independent of staple position, as an MCL-1 SAHB with the traditional BIM staple position (MCL-1 SAHB$_A$) also engages VLCAD, while a BIM SAHB with the traditional MCL-1 SAHB staple position (BIM SAHB$_F$) does not.
Figure 11:
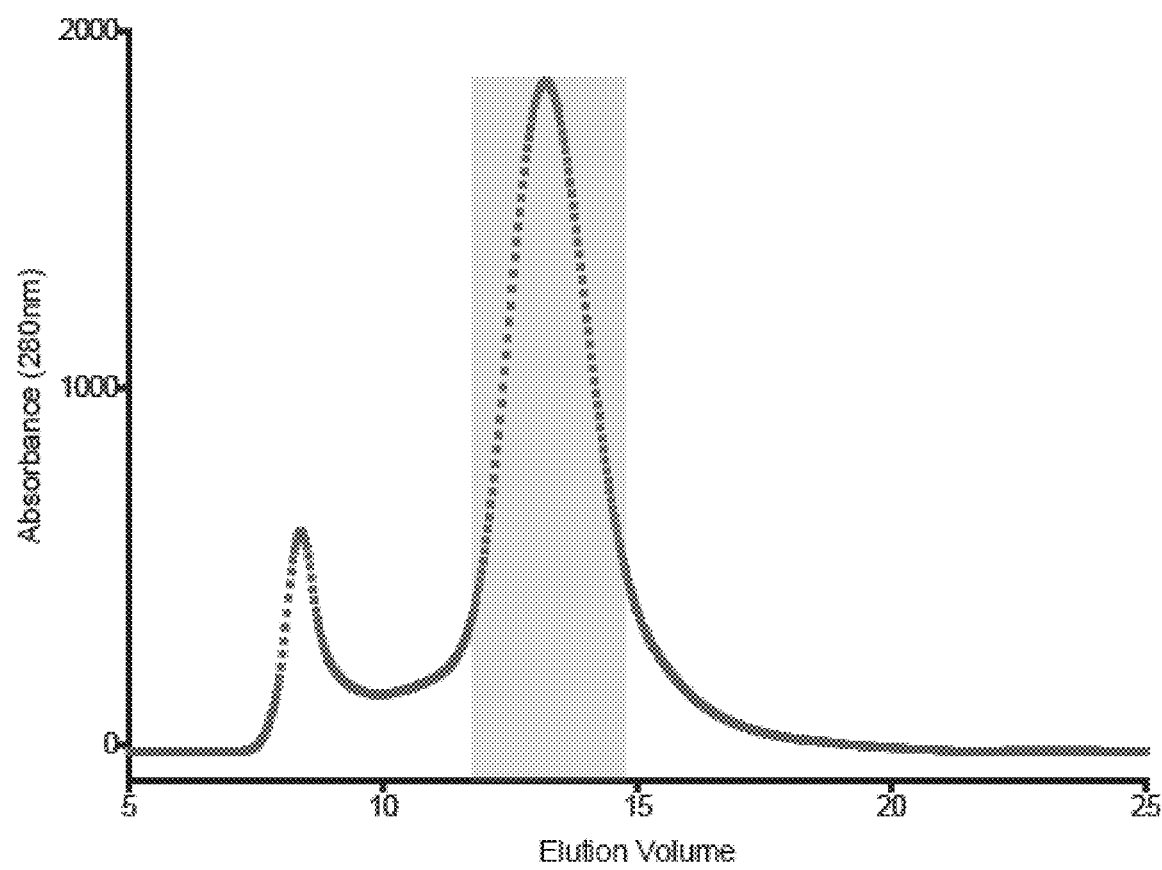
FIG. 11 is a depiction of the size exclusion chromatography elution profile of recombinant VLCAD produced in E. coli, showing a major peak corresponding to the obligate dimer form of the enzyme which was collected for biochemical studies (shaded region).
Figure 12:
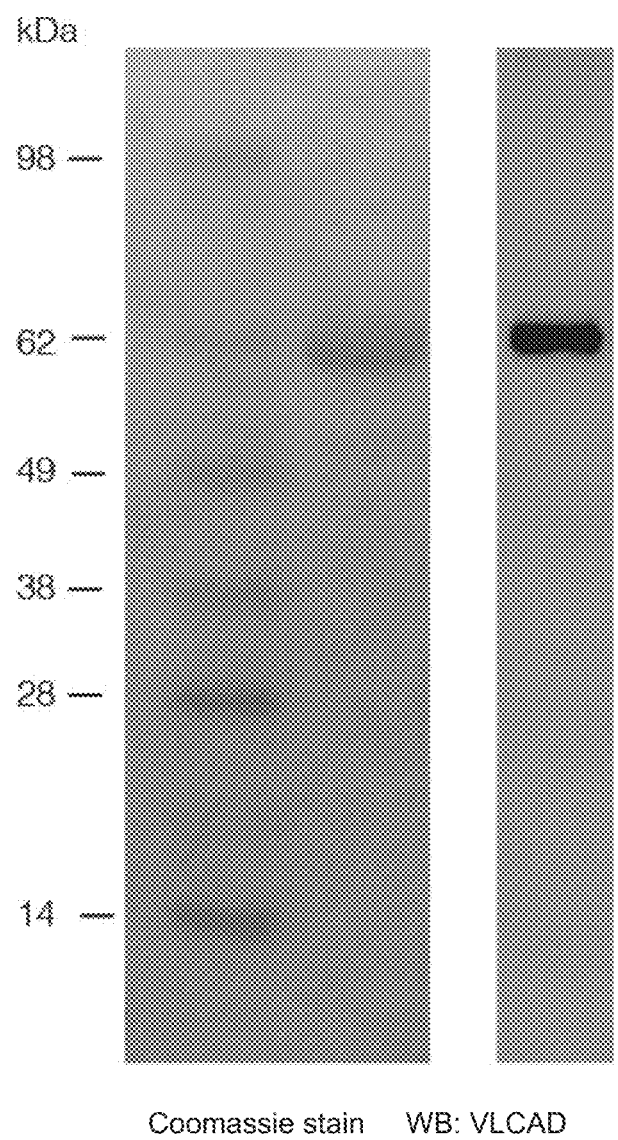
FIG. 12 is a Coomassie gel and Western blot showing that recombinant VLCAD purified by size exclusion chromatography migrates at the expected size on a reducing/denaturing gel (left) and can be identified by an anti-VLCAD polyclonal antibody (right).
Figure 13:
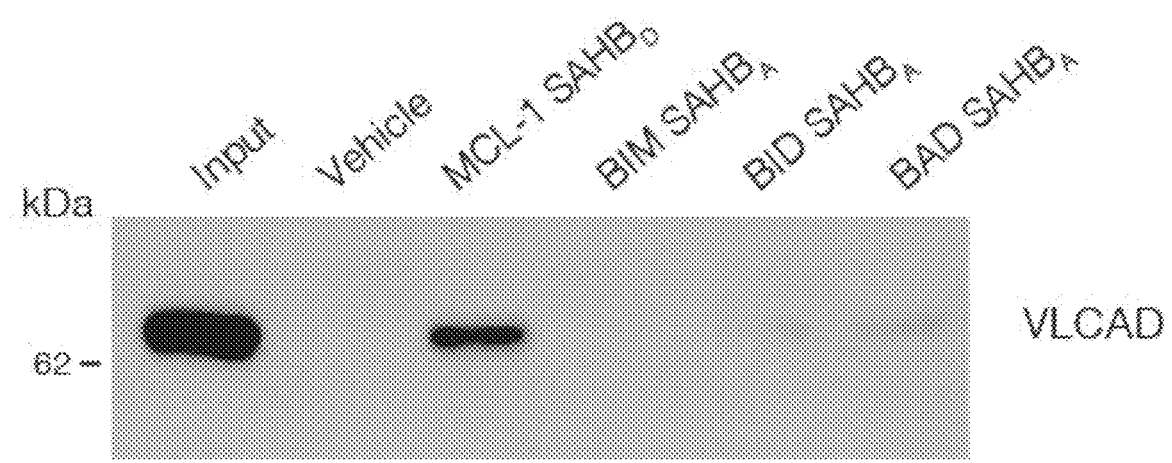
FIG. 13 is a pulldown assay showing that MCL-1 SAHB$_D$, but not the other BH3 SAHBs, directly binds to recombinant VLCAD.

To validate the MS result, the pulldowns were repeated and eluates run on a gel for anti-VLCAD Western blot analysis. VLCAD was detected in the MCL-1 SAHB$_D$ pulldown eluate, confirming the MS results. Importantly, pulldowns conducted with peptide helices modeled after the BH3 domains of BIM, BID, or BAD did not engage VLCAD in lysates, highlighting the specificity of the MCL-1 stapled peptide/VLCAD interaction. All peptides faithfully recapitulated native BH3-binding propensities for endogenous MCL-1 protein (FIG. 8). The eluates were then probed for the other members of the acyl-CoA dehydrogenase family that manifest shorter fatty acid substrate specificities. MCL-1 SAHB$_D$ was able to pull down VLCAD, but not MCAD or SCAD (FIG. 9). Because the traditional MCL-1 staple location differs from that of the BIM, BID, and BAD SAHBs, it was important to confirm that the observed VLCAD binding specificity was due to BH3 sequence selectivity, not staple position. A BIM SAHB with the traditional MCL-1 staple (BIM SAHB$_F$), and a MCL-1 stapled peptide with the traditional BIM staple (MCL-1 SAHB$_A$), were generated. Whereas both MCL-1 stapled peptides (MCL-1 SAHB$_A$ and SAHB$_D$) engaged VLCAD, BIM SAHBs showed no VLCAD binding activity (FIG. 10). To confirm that the selective interaction between MCL-1 SAHB$_D$ and VLCAD is direct, recombinant VLCAD was generated and purified by size exclusion chromatography (FIGS. 11 and 12). As for native VLCAD from MEF lysates, only Btn-MCL-1 SAHB$_D$, but not other BH3 SAHBs, pulled down recombinant VLCAD, which confirmed that the identified interaction between MCL-1 stapled peptides and VLCAD is both selective and direct (FIG. 13).

Figure 14A:
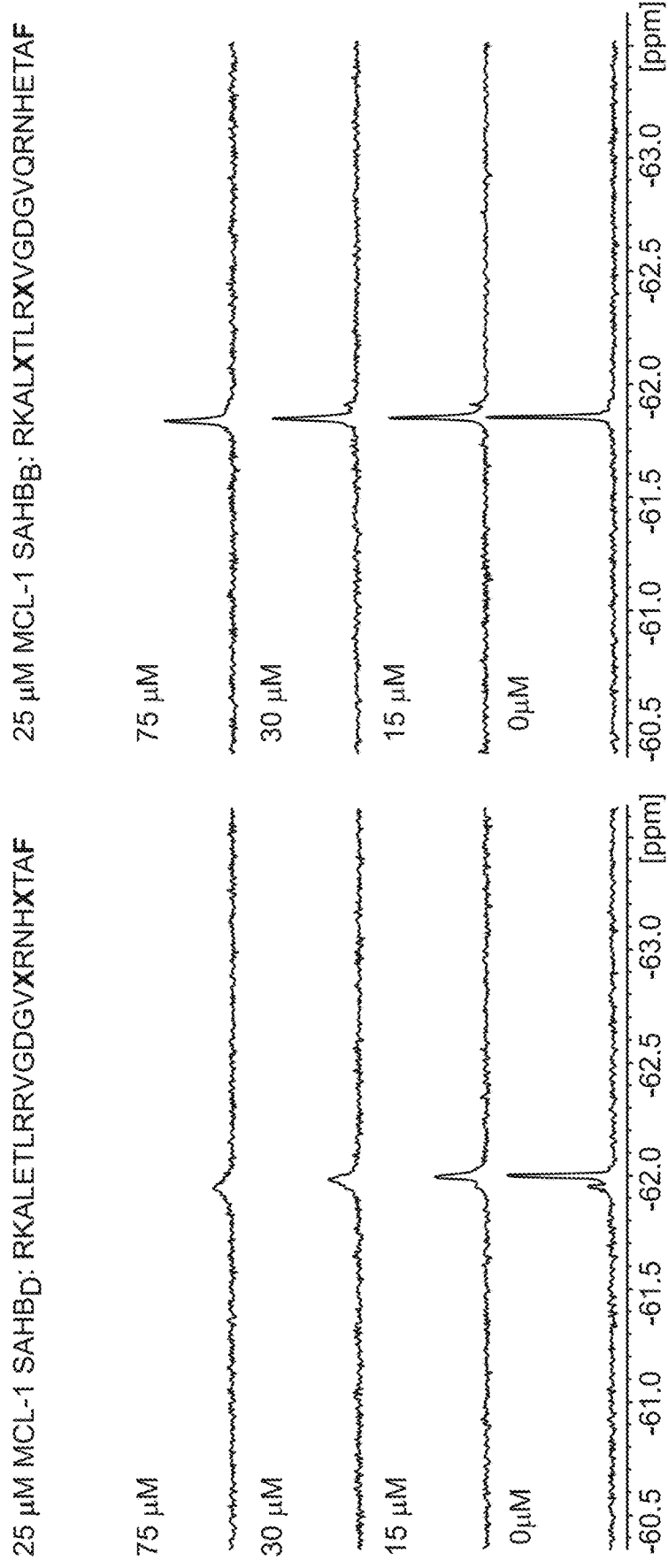
FIG. 14A is a series of $^{19}$F NMR binding assays demonstrating that VLCAD binds directly to MCL-1 SAHB$_D$ (left; SEQ ID NO:19), but not to MCL-1 SAHB$_B$ (right; SEQ ID NO:9), as reflected by broadening of the peptide NMR peak.
Figure 14B:
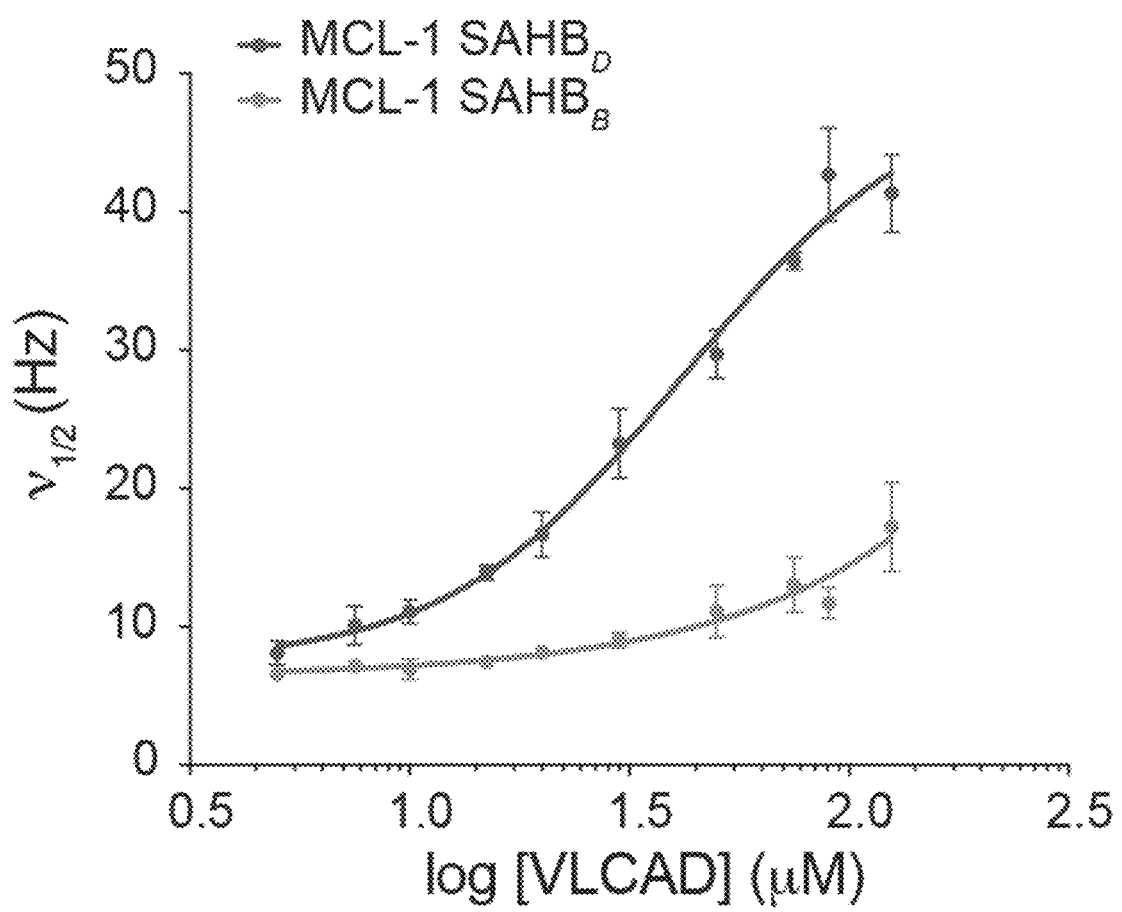
FIG. 14B is a graph depicting the quantification of $^{19}$F NMR binding data in FIG. 14A demonstrating that MCL-1 SAHB$_D$ (upper curve), but not MCL-1 SAHB$_B$ (lower curve), binds directly to recombinant VLCAD.
Figure 15A:
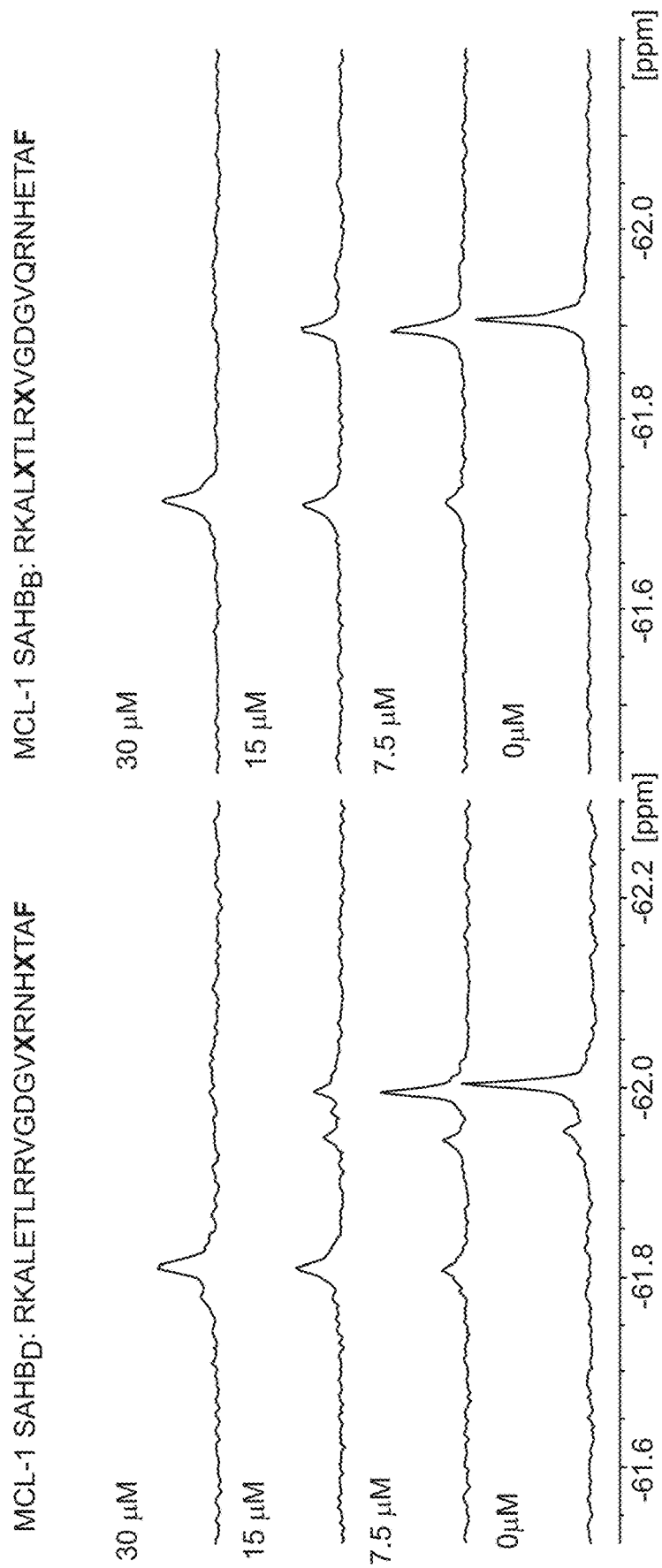
FIG. 15A is a series of $^{19}$F NMR binding assays demonstrating that MCL-TΔNΔC binds directly to MCL-1 SAHB$_D$ (left; SEQ ID NO:19) and MCL-1 SAHB$_B$ (right; SEQ ID NO:9), as reflected by a chemical shift of the peptide NMR peak.
Figure 15B:
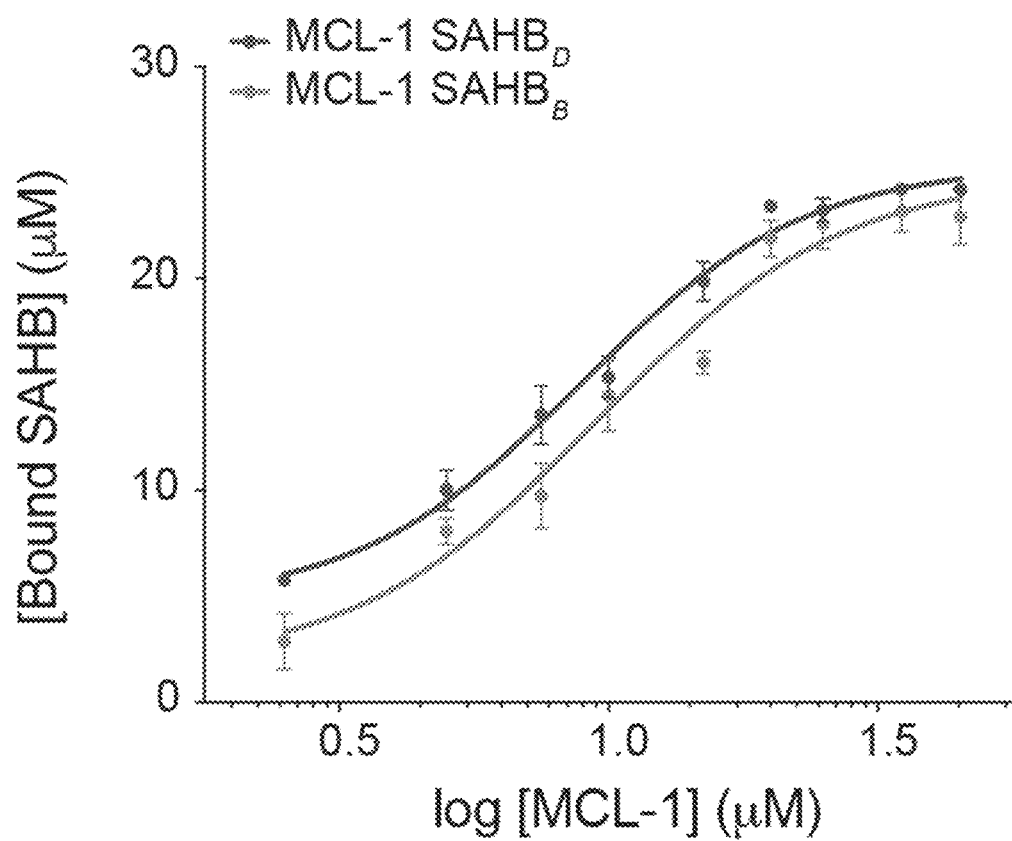
FIG. 15B is a graph depicting the quantification of $^{19}$F NMR binding data in FIG. 15A demonstrating that MCL-1 SAHB$_D$ (upper curve), and MCL-1 SAHB$_B$ (lower curve), bind directly to recombinant MCL-TΔNΔC.
Figure 16:
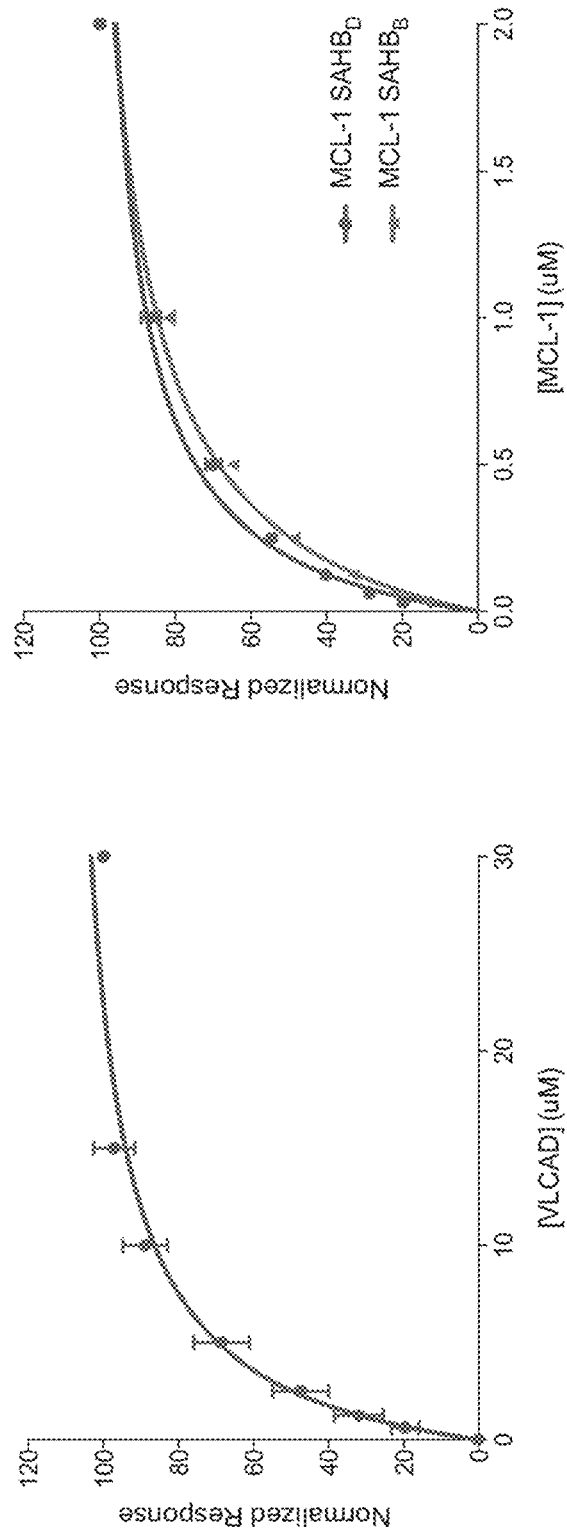
FIG. 16 is a graphical depiction of biolayer interferometry binding assays demonstrating that MCL-1 SAHBs $_B$ and $_D$ both bind to MCL-1 (right), whereas only MCL-1 SAHB$_D$ engages VLCAD (left). (Note: there is no detectable binding interaction between MCL-1 SAHB$_B$ and VLCAD, and therefore there was no association binding data to plot.)

To measure the direct binding interaction, $^{19}$F NMR binding studies were conducted using fluorinated analogs of MCL-1 SAHB$_D$. As VLCAD protein is titrated into a MCL-1 SAHB$_D$ solution, the resultant peak broadens, indicative of a direct binding event. However, the same experiment performed with an MCL-1 SAHB containing a different staple position (MCL-1 SAHB$_B$) showed little to no peak broadening in the presence of the same VLCAD concentrations (FIG. 14). Both SAHBs, however, bind MCL-1ΔNΔC, as illustrated by a chemical shift of the peptide NMR peak in both cases (FIG. 15). Thus, MCL-1 SAHB construct target-binding specificities differ by staple location, suggestive of distinct binding determinants of MCL-1 vs. VLCAD for engaging the MCL-1 BH3 helix. Biolayer interferometry, a completely distinct binding analysis, revealed the same qualitative interaction pattern: both MCL-1 SAHBs associate with MCL-1ΔNΔC, while only MCL-1 SAHB$_D$ engages VLCAD (FIG. 16). To perform these experiments, N-terminal Btn-PEG analogs of the peptides were immobilized onto streptavidin probes that were then placed into protein solutions at a variety of concentrations to measure ligand-target association.

Figure 17:
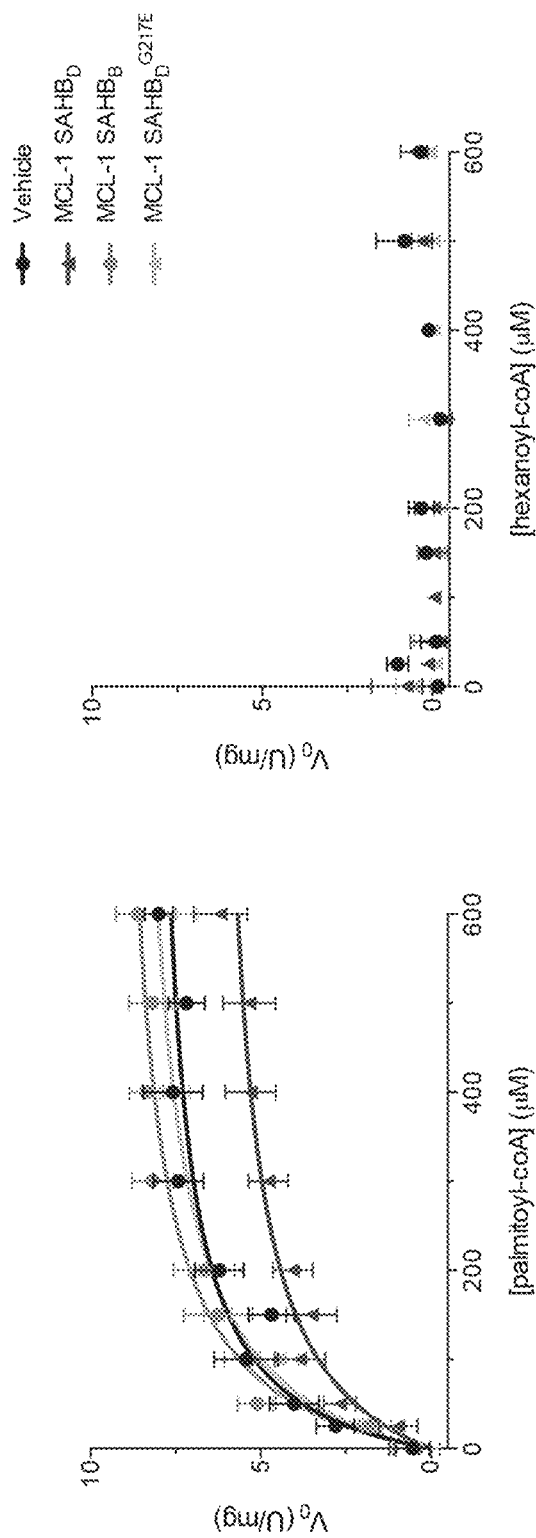
FIG. 17 is a graphical depiction of an in vitro enzymatic activity assay tracking VLCAD activity in the presence of its substrate (palmitoyl-CoA) or lack of activity in the presence of a short acyl-CoA. MCL-1 SAHB$_D$ impairs recombinant VLCAD activity whereas other analogs that don't bind to VLCAD have no effect on VLCAD activity.

To assess whether the direct MCL-1/VLCAD binding interaction influences VLCAD enzymatic activity, an in vitro enzymatic activity assay was conducted. Recombinant VLCAD was incubated with its substrate (palmitoyl-CoA) and ferrocenium hexafluorophosphate, a strong electrophile. As VLCAD acts upon its substrate and oxidizes it, the ferrocenium hexafluorophosphate is reduced, causing a change in absorbance that is readily measured. Addition of a short acyl-CoA, hexanoyl-CoA, resulted in no signal, as this fatty acid substrate lies outside of VLCAD's spectrum of enzymatic activity. Pre-incubation of VLCAD with MCL-1 SAHB$_D$ caused a decrease in enzymatic activity, an effect not observed when MCL-1 SAHBs that do not bind VLCAD were added (FIG. 17).

Of note, the phenomenon of a full-length protein serving as an enzymatic agonist, with a stapled peptide modeled after an interaction helix functioning as an antagonist, has been observed in the context of our SOS1/KRAS work (see, e.g., Leshchiner et al., *Proc NatlAcad Sci USA* 2015). In that example, SOS1 binds to and enhances KRAS nucleotide exchange, with a protein interaction interface composed of a SOS1-helix in the KRAS surface groove. While the SOS1 protein catalyzes KRAS nucleotide exchange, a stapled SOS1 peptide designed based on its KRAS-binding domain inhibits nucleotide exchange both by dissociating the protein-protein complex and independently inhibiting enzymatic activity through direct stapled SOS1 helix/KRAS interaction.

Example 4: Sequence Determinants for MCL-1 SAHB$_D$ Interaction with VLCAD

The binding determinants for the MCL-1 BH3/VLCAD interaction were investigated by generating a series of biotinylated MCL-1 SAHB$_D$ alanine point mutants (FIG. 18A) and performing streptavidin pull-downs from MEF lysates, followed by VLCAD and MCL-1 western analysis of the resulting eluates. In comparing the binding activities toward native VLCAD and MCL-1, a series of alanine mutants that disrupted both binding interactions were identified, in addition to residues that revealed selectivity for each of the targets (FIG. 18B, left). For example, mutagenesis of L213—a conserved residue across all BH3 domains—disrupted biotinylated MCL1-SAHB$_D$ interaction with VLCAD and MCL-1, whereas alanine mutation of L210 or the previously identified MCL-1 selectivity determinant, V220, were uniquely disruptive to VLCAD and MCL-1, respectively. Most striking, the series of disruptive mutations for each target defined partially overlapping binding interfaces that were shifted from one another by approximately 90 degrees (FIG. 18B, right), revealing a distinct mode for MCL-1 BH3 interaction with VLCAD. Alanine mutations that reduced the wild-type interaction by more than 50% (dotted line) are colored dark gray on the helical wheels, whereas those constructs demonstrating less of a negative influence, no effect, or a binding enhancement are colored light gray. Native alanines and residues not mutated are colored white. The dotted semicircles highlight the distinctive MCL-1 BH3 binding interfaces for VLCAD versus MCL-1 engagement, as defined by the differential sensitivities to alanine mutagenesis.

Figure 19B:
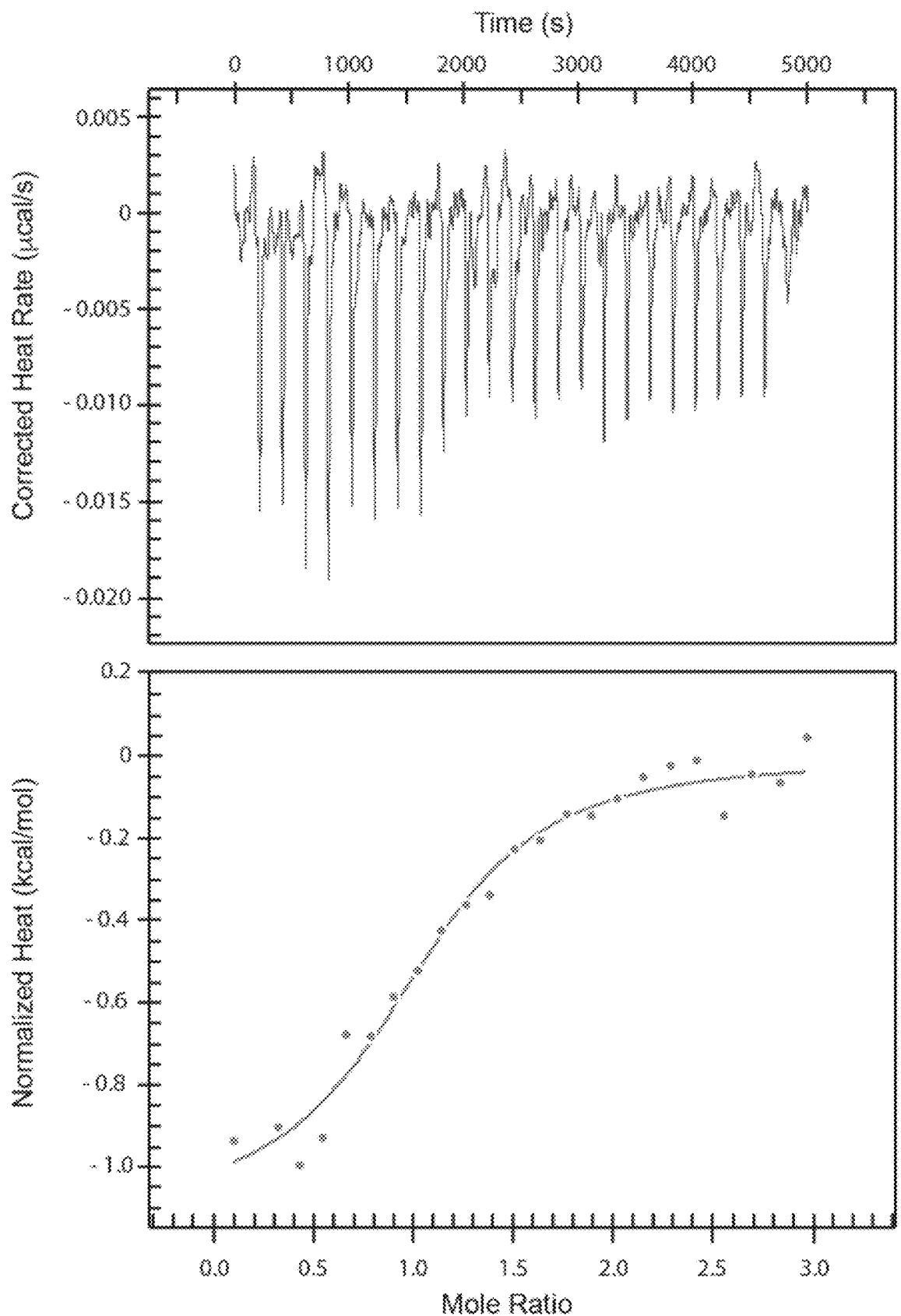
FIG. 19B represents the measurement of the dissociation constant of the MCL-1 SAHB$_D$ V220A/VLCAD interaction.

The alanine mutant peptide panel was then utilized in an isothermal calorimetry (ITC)-based enthalpy screen to assess the relative binding activities of the different peptides to recombinant VLCAD protein (FIG. 19A). Although some differences in binding hierarchy were observed between the pull down (native protein) and ITC (purified recombinant protein) methods, those peptides displaying the strongest and weakest binding activity for VLCAD were similar between the two analyses. For example, MCL-1 SAHBs D218A and V220A showed robust binding in both assays, whereas R207A, L213A, R214A, R215A, and F228A consistently displayed weak VLCAD association. ITC analysis of the strongest binder, MCL-1 SAHB$_D$ V220A, demonstrated a dissociation constant for recombinant VLCAD interaction of 1.7 M (FIG. 19B).

Figure 20:
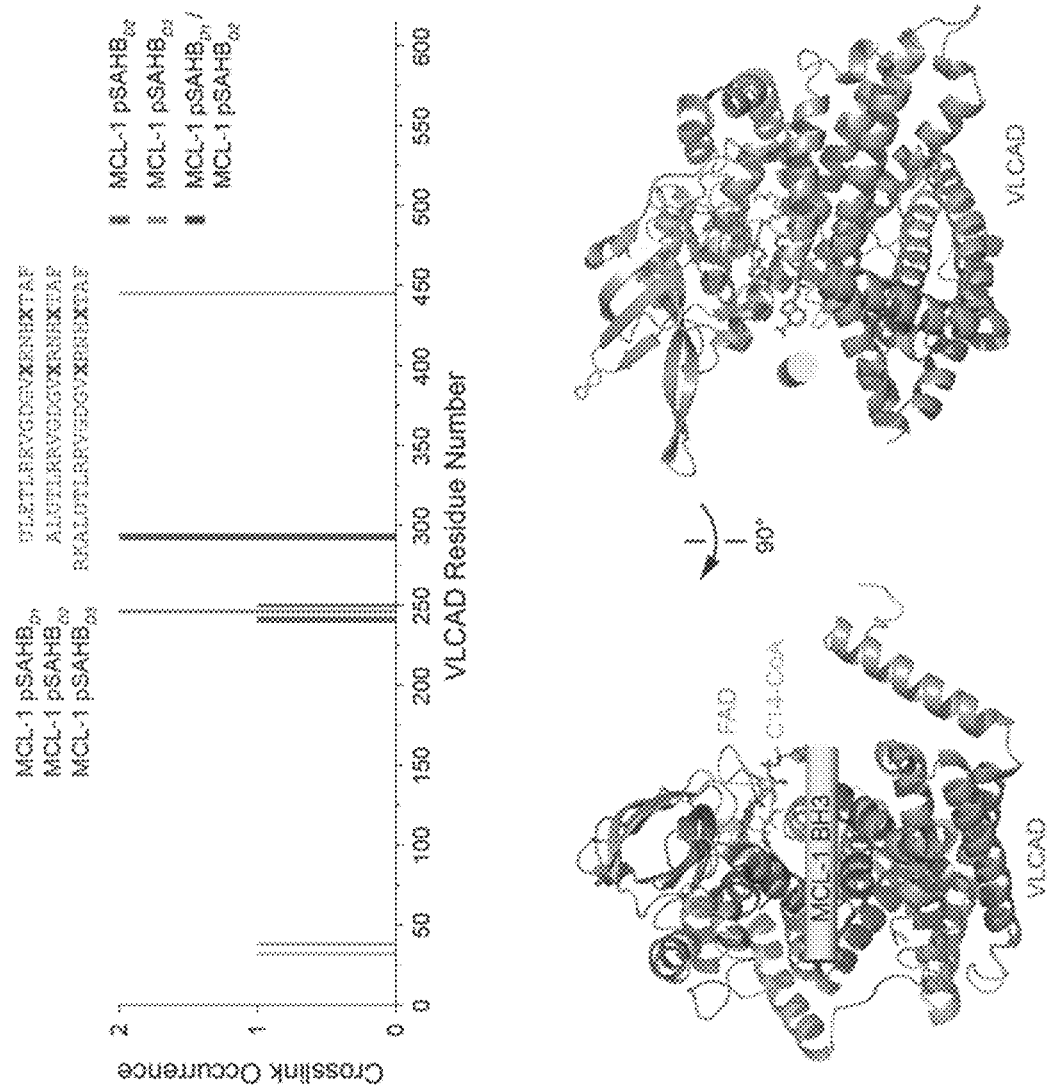
FIG. 20 depicts the utilization of photo-crosslinkable MCL-1 SAHBs [SAHB$_{D1}$ (SEQ ID NO:61), SAHB$_{D2}$ (SEQ ID NO:62), and SAHB$_{D3}$ (SEQ ID NO:63), wherein "U" is a benzophenone moiety] to localize the MCL-1 BH3 binding site on VLCAD.

Below is a summary of the binding properties of the MCL1-SAHB$_D$ and SAHB$_D$ Ala mutants:
  Best overall binders to VLCAD based on pull-downs and ITC: D218A and V220A
  Binds to both VLCAD and MCL-1: SAHB$_D$, E211A, D218A, G219A
  Binds VLCAD but weakly or not to MCL-1: T212A, V216A, G217A, V220A
  Binds MCL-1 but weakly or not to VLCAD: L210A, R215A
  Does not bind either MCL-1 or VLCAD: L213A, R214A, H224A, F228A
  Does not bind to VLCAD and shows diminished binding to MCL-1: R207A
  Shows enhanced binding to VLCAD and diminished binding to MCL-1: K208A
  Shows diminished binding to both VLCAD and MCL-1: T226A Example 5: Localization of the MCL-1 BH3 Binding Site on VLCAD To localize the region of MCL-1 BH3 interaction on VLCAD, a photoaffinity labeling mass spectrometry approach was applied. A panel of biotinylated photoreactive SAHB (pSAHB) peptides bearing a benzophenone moiety in discrete locations were synthesized (FIG. 20 top). pSAHBs were then incubated with recombinant VLCAD and exposed to UV light, which results in the benzophenone covalently attaching to VLCAD residues in the vicinity of the binding site. pSAHBs were then subjected to streptavidin capture and high-stringency washes to remove uncrosslinked protein. Trypsinization of the crosslinked samples and analysis by mass spectrometry then identified the residues on VLCAD that were covalently linked to the pSAHBs (FIG. 20 top). Whereas MCL-1 pSAHBs D1 and D2 both crosslinked to VLCAD residues V292 and M294, MCL-1 pSAHBD2 also captured amino acids T240, F242, R246, and G250, and MCL-1 pSAHB$_{D3}$ crosslinked to S32, F38, and S445. Intriguingly, the series of identified crosslinks all localized to a discrete surface groove formed by the confluence of the β-sheet and α-helical-3 motifs, which lie just proximal to the binding sites of the FAD co-factor and the enzyme substrate itself (FIG. 20 bottom). Using the identified crosslinks as constraints for computational docking, the MCL-1 BH3 domain is predicted to engage VLCAD by a helix-in-groove interaction that is analogous to the established interaction paradigm for BH3 helices with BCL-2 family anti-apoptotic surface grooves.

Figure 21:
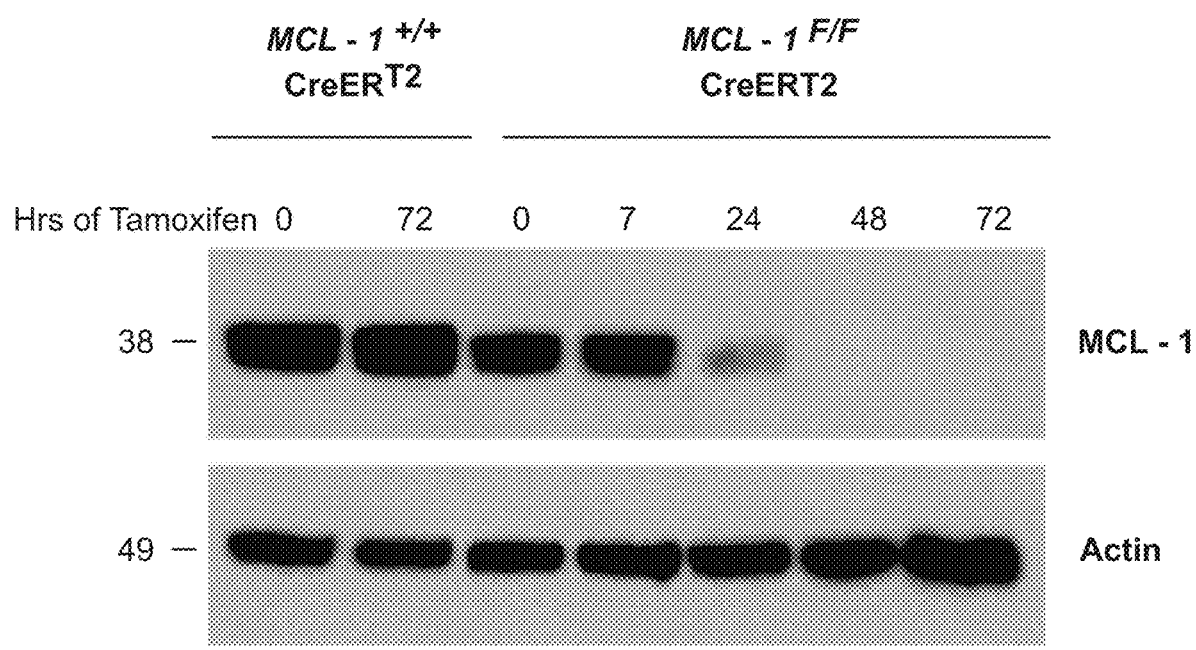
FIG. 21 is a Western blot showing targeted deletion of Mcl-1 in cell culture achieved using the Mcl-1$^{F/F}$ CreER$^{T2}$ cell line system. Tamoxifen treatment of Mcl-1$^{F/F}$ CreER$^{T2}$ cells causes loss of MCL-1 expression, while treatment of the control Mcl-1$^{+/+}$ CreER$^{T2}$ cells has no effect.
Figure 22:
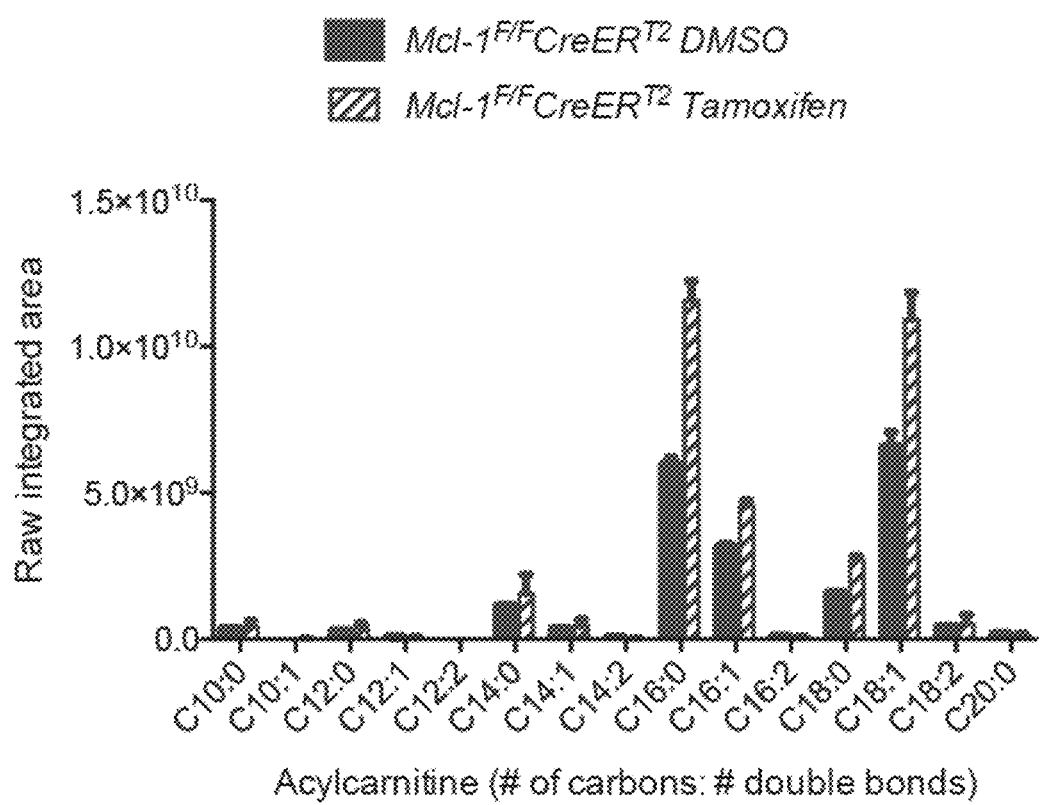
FIG. 22 is a bar graph showing that, upon targeted deletion of MCL-1 in mouse embryonic fibroblasts (MEFs), there is a notable increase in levels of long chain fatty acylcarnitines.
Figure 23:
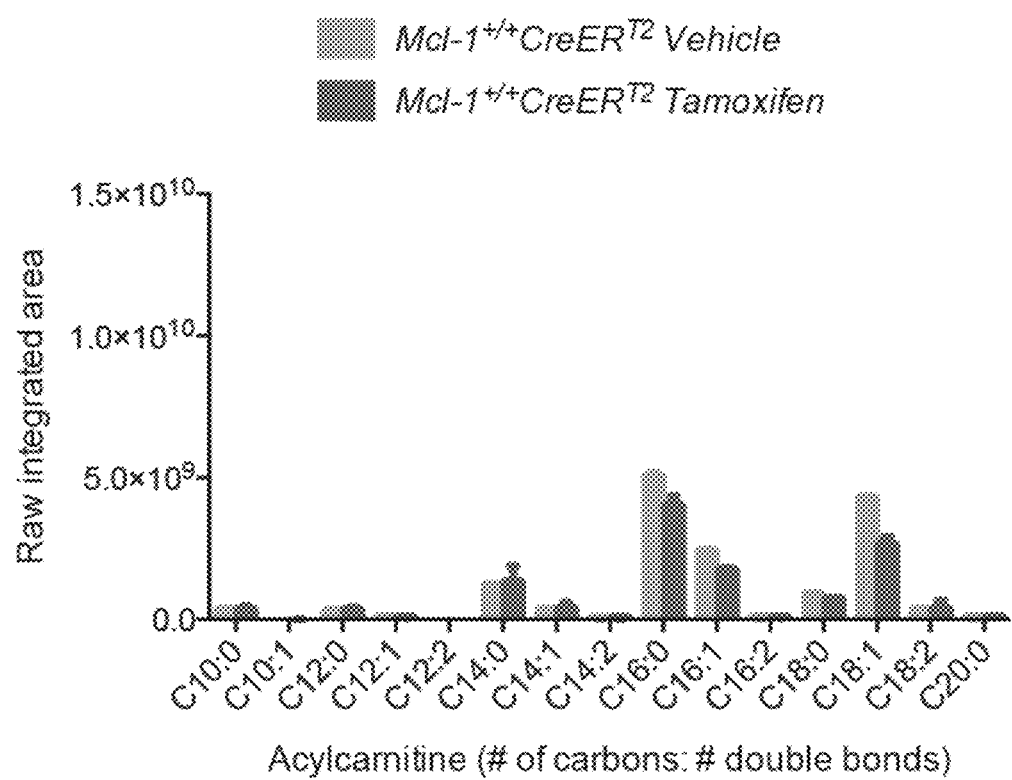
FIG. 23 is a bar graph showing that tamoxifen treatment has no independent effect on acylcarnitine levels, as demonstrated by similar fatty acylcarnitine levels in the indicated MEFs subjected to either vehicle or tamoxifen.
Figure 24:
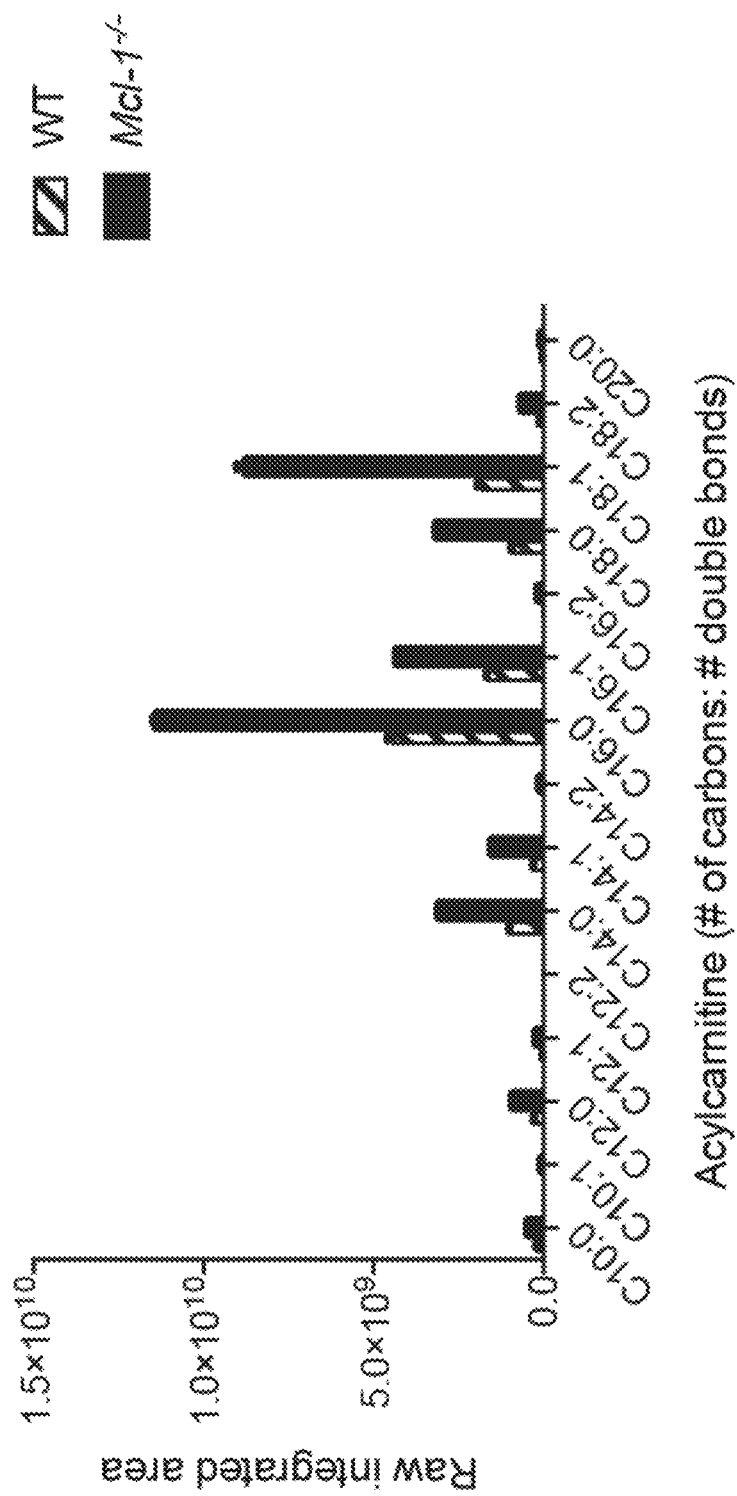
FIG. 24 is a bar graph showing that MEFs that have sustained long term MCL-1 deletion (Mcl-1$^{-/-}$ MEFs) likewise manifest increased levels of long chain fatty acylcarnitines as compared to wild-type MEFs.

Example 6: Mcl-1 Deletion Leads to Elevated Levels of Very Long-Chain Fatty Acylcarnitines To explore the effect of MCL-1 loss on fatty acid β-oxidation, a cellular model system that can acutely delete Mcl-1 was employed. Treatment of Mcl-1$^{F/F}$ CreER$^{T2}$ MEFs with 100 nM tamoxifen resulted in elimination of MCL-1 expression by 48 hours, as detected by MCL-1 Western analysis, whereas tamoxifen has no such effect on Mcl-1$^{+/+}$CreER$^{T2}$ MEFs (FIG. 21). A blockade in β-oxidation manifests as an accumulation of acylcarnitine species, as acyl-CoAs that cannot enter the pathway are rapidly converted into their acylcarnitine analogs. MS-based quantification of acylcarnitines is performed both in the laboratory setting as well as in the clinic to diagnose inborn errors of metabolism that disrupt β-oxidation. Using this technique, intracellular acylcarnitine levels were quantified in Mcl-1$^{F/F}$ CreER$^{T2}$ cells treated with either vehicle or tamoxifen. Upon Mcl-1 deletion, there was a notable increase in the levels of very long-chain fatty acylcarnitines (FIG. 22). To ensure that the acylcarnitine accumulation was unrelated to tamoxifen treatment, the experiment was repeated on Mcl-1$^{+/+}$ CreER$^{T2}$ MEFs treated with vehicle or tamoxifen. Indeed, tamoxifen treatment had no independent effect on acylcarnitine levels (FIG. 23). Acylcarnitine quantification was then repeated using cells that have sustained long term Mcl-1 deletion (Mcl-1$^{-/-}$ MEFs). Compared to wild-type MEFs, Mcl-1$^{-/-}$ MEFs also showed very long-chain acylcarnitine accumulation (FIG. 24), implicating a requirement for MCL-1 to maintain homeostatic VLCAD activity.

Figure 25:
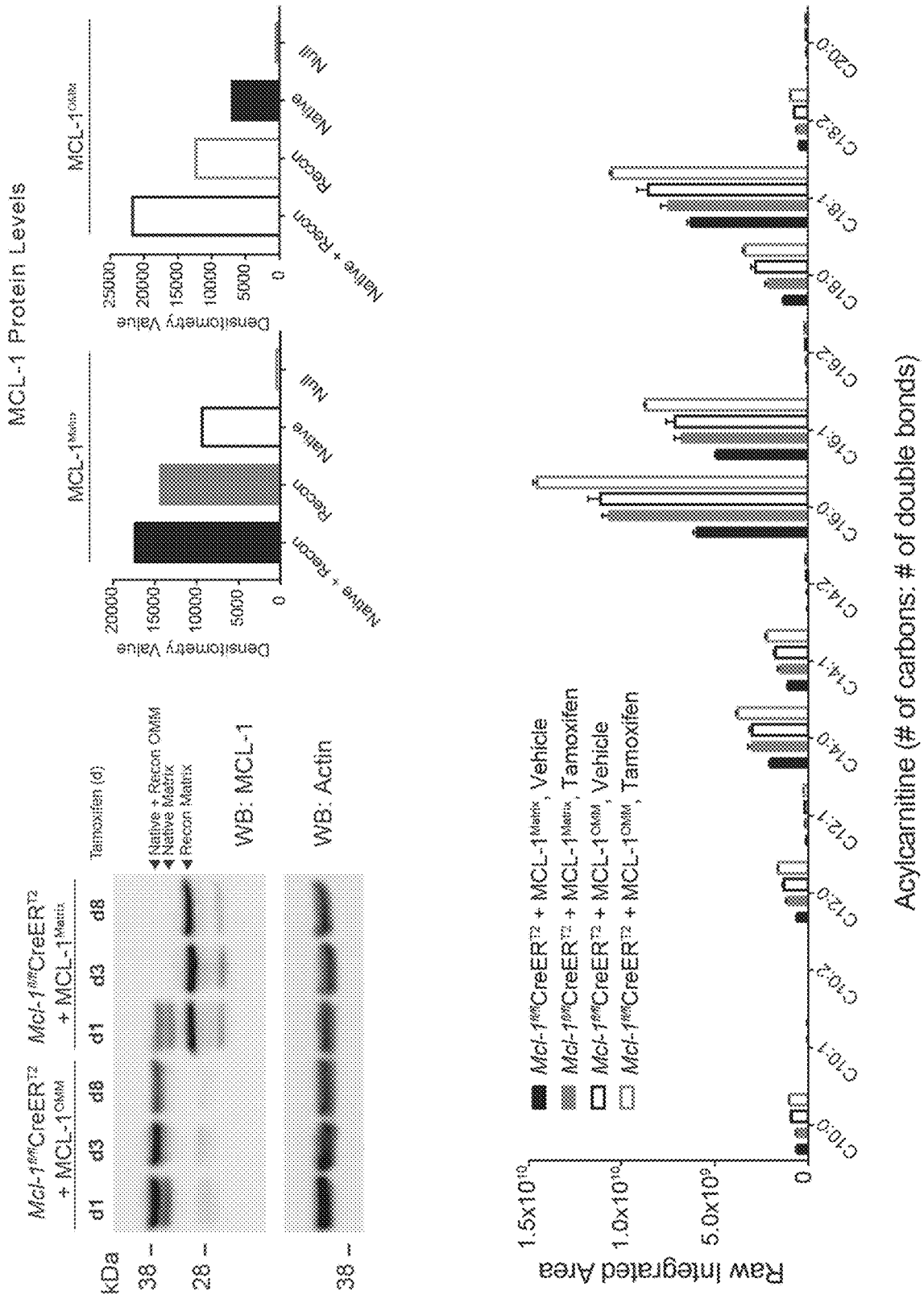
FIG. 25 shows based on acylcarnitine quantification reveals that the elevation in levels of long-chain acylcarnitines correlates with expression of MCL-1$^{Matrix}$, but not MCL-1$^{OMM}$.

Example 7: The Regulatory Role of MCL-1 in Fatty Acid Metabolism is Isoform Specific Given the mitochondrial matrix localization and bioenergetic function of VLCAD, we hypothesized that MCL-1$^{Matix}$ mediated the observed effects on β-oxidation upon deletion of Mcl-1. To test this hypothesis, we performed comparative acylcarnitine quantification on a series of MEFs expressing differential levels of outer mitochondrial membrane (OMM) and matrix forms of MCL-1. Mcl-1$^{fl/fl}$CreER$^{T2}$ MEFs were transfected with constructs that either produced MCL-1$^{OMM}$ or MCL-1$^{Matrix}$. Upon tamoxifen treatment of the generated lines, endogenous Mcl-1 was deleted and the site-specific isoforms of MCL-1 remained (FIG. 25 top left). Mcl-1$^{fl/fl}$CreER$^{T2}$+MCL-1$^{OMM}$ and Mcl-1$^{fl/fl}$CreER$^{T2}$+MCL-1$^{Matrix}$ MEFs were treated with tamoxifen or vehicle for 48 hours and then subjected to palmitic acid-containing media for 96 hours, followed by lipid extraction. Extracts were analyzed by mass spectrometry to quantify cellular acylcarnitine levels. Interestingly, the levels of observed long-chain fatty acylcarnitines were inversely correlated to the cumulative amount of native and/or reconstituted MCL-1$^{Matrix}$, but were unaffected by the presence or absence of MCL-1$^{OMM}$, implicating MCL-1$^{Matrix}$ in the regulation of long-chain fatty acids (FIG. 25 top right, bottom).

Figure 26:
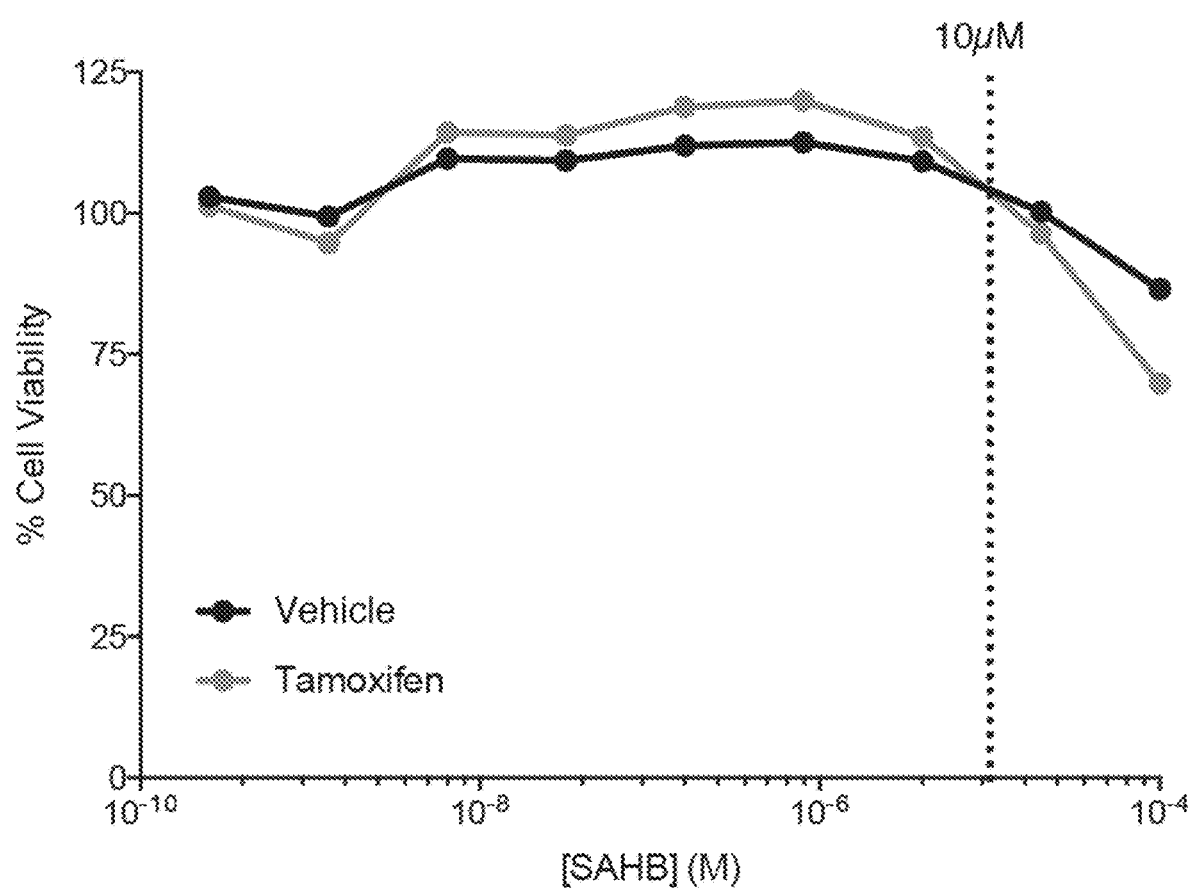
FIG. 26 is a graph depicting MCL-1 SAHB$_D$ dose-response treatment of vehicle and tamoxifen exposedMcl-1$^{F/F}$CreER$^{T2}$ cells to identify the maximal dose of SAHB that does not cause cytotoxicity, for use in acylcarnitine quantification experiments (see below). Essentially no cytotoxicity was observed for MCL-1 SAHB$_D$ treatment except at the highest dose applied (100 μM).
Figure 27:
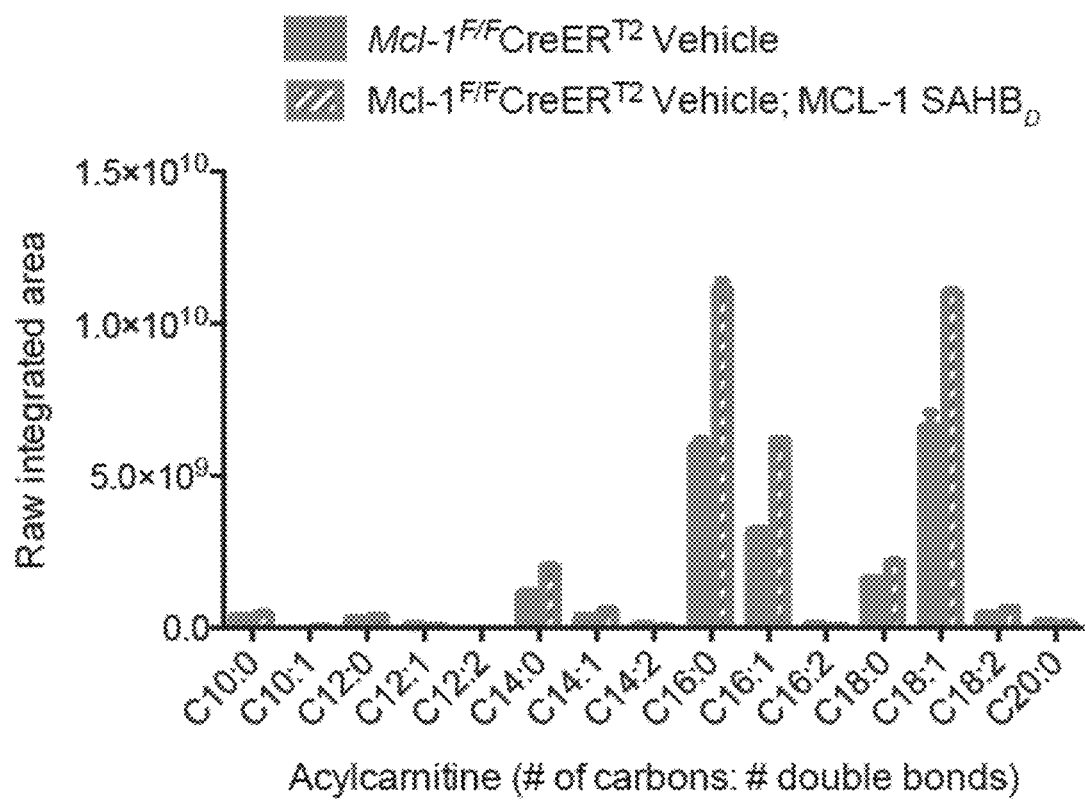
FIG. 27 is a bar graph showing that Mcl-1$^{F/F}$ CreER$^{T2}$ MEFs that maintain wild-type MCL-1 expression (no tamoxifen treatment) manifest increased levels of long chain acyl carnitines upon treatment with MCL-1 SAHB$_D$, which mirrors the phenotype observed for acute or chronic Mcl-1 deletion.
Figure 28:
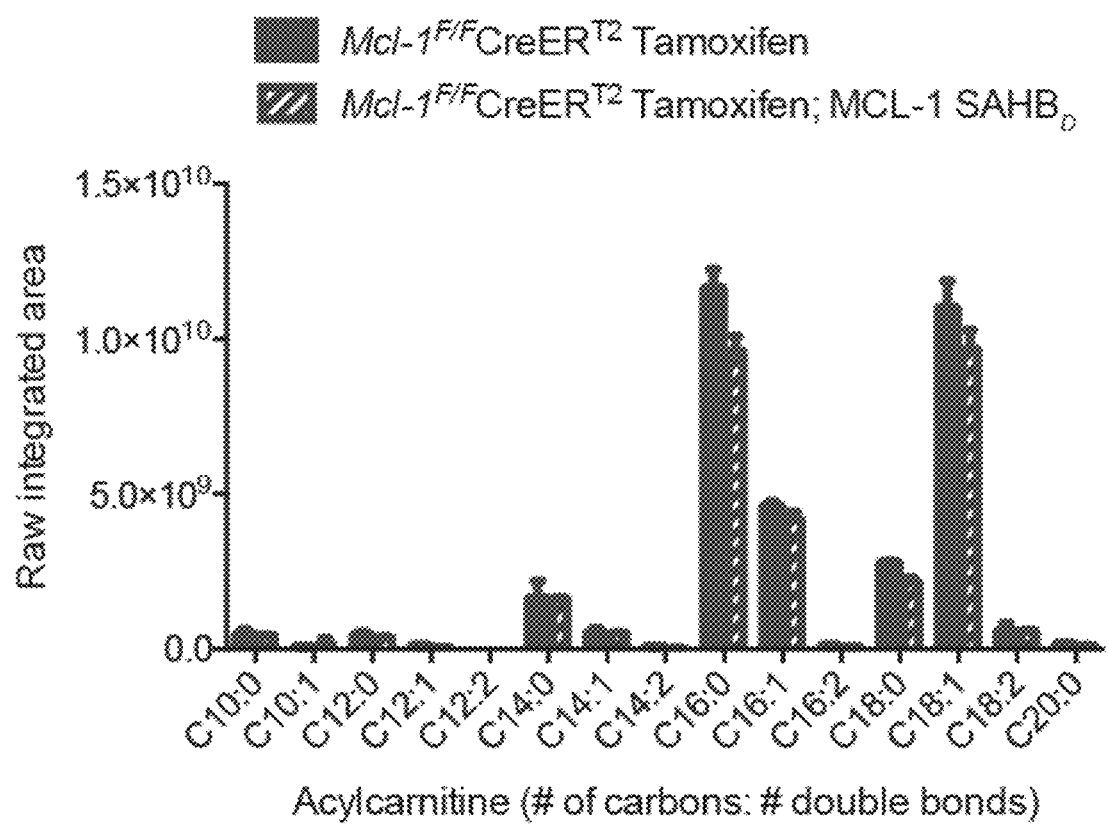
FIG. 28 is a bar graph showing that MCL-1 SAHB$_D$ treatment had no effect on the already elevated levels of acylcarnitines observed in Mcl-1$^{F/F}$ CreER$^{T2}$ MEFs subjected to tamoxifen treatment.

Example 8: Administration of a MCL-1 Stapled Peptide Mimics the Effect of Mcl-1 Deletion The effect of MCL-1 stapled peptide treatment on acylcarnitine levels in cells was evaluated. An ideal non-cytotoxic dose of MCL-1 SAHB$_D$ was identified for use in acylcarnitine quantification experiments, as revealed by a dose-response treatment of vehicle- and tamoxifen-treated Mcl-1$^{F/F}$ CreER$^{T2}$ followed by cell viability read-out (FIG. 26). Mcl-1$^{F/F}$ CreERT2 MEFs, not exposed to tamoxifen, were treated with MCL-1 SAHB$_D$ (10 µM) or vehicle for 48 hours and then harvested for acylcarnitine quantitation. Strikingly, MCL-1 SAHB$_D$ treatment resulted in elevated levels of very long-chain acylcarnitines relative to vehicle-treated control (FIG. 27). In contrast, MCL-1 SAHB$_D$ treatment had no effect on the already elevated levels of acylcarnitines observed in Mcl-1$^{F/F}$ CreER$^{T2}$ MEFs subjected to tamoxifen (FIG. 28). Taken together, these results indicate that administration of MCL-1 stapled peptides induces a loss-of-function effect on the MCL-1/VLCAD-regulated fatty acid oxidation pathway. Correspondingly, in the absence of MCL-1, MCL-1 stapled peptides do not confer a gain-of-function effect on the enzymatic activity of VLCAD.

Example 9: Effect of Mcl-1 Deletion on VLCAD In Vivo

Figure 29:
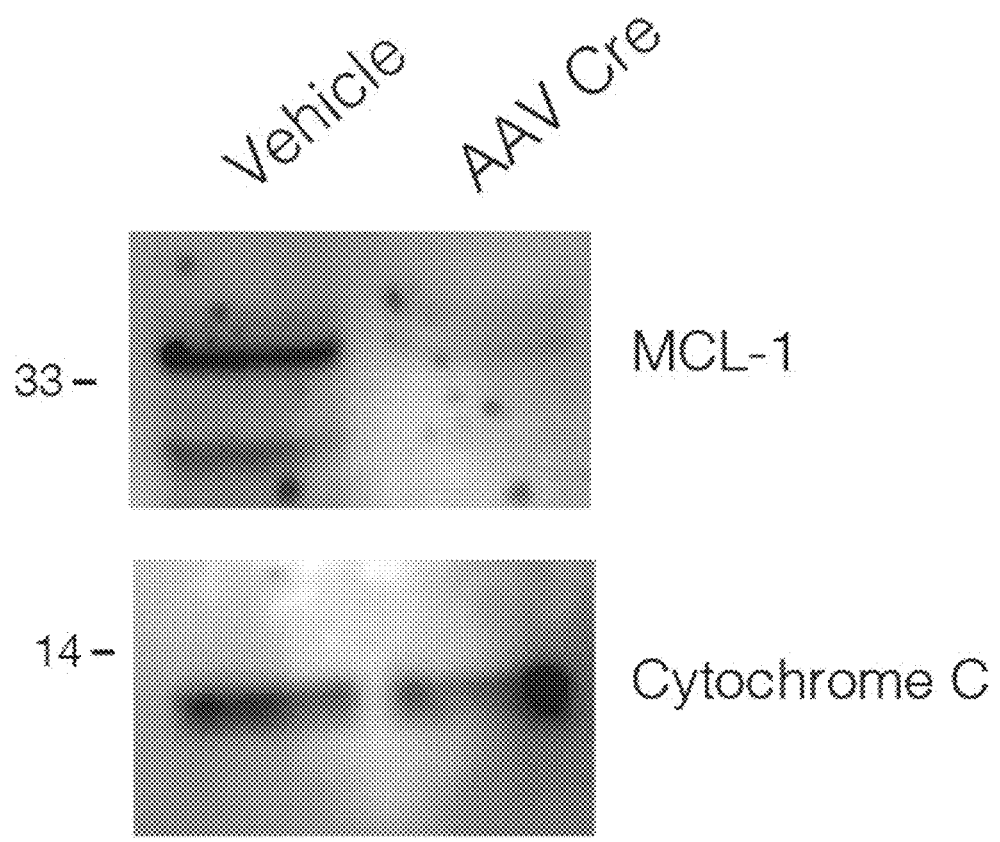
FIG. 29 is a Western blot showing that injection of an AAV.TBG.Cre adenovirus into Mcl-1$^{F/F}$ mice results in hepatocyte-specific knockout of Mcl-1, as illustrated by analysis of liver mitochondrial lysates.
Figure 30:
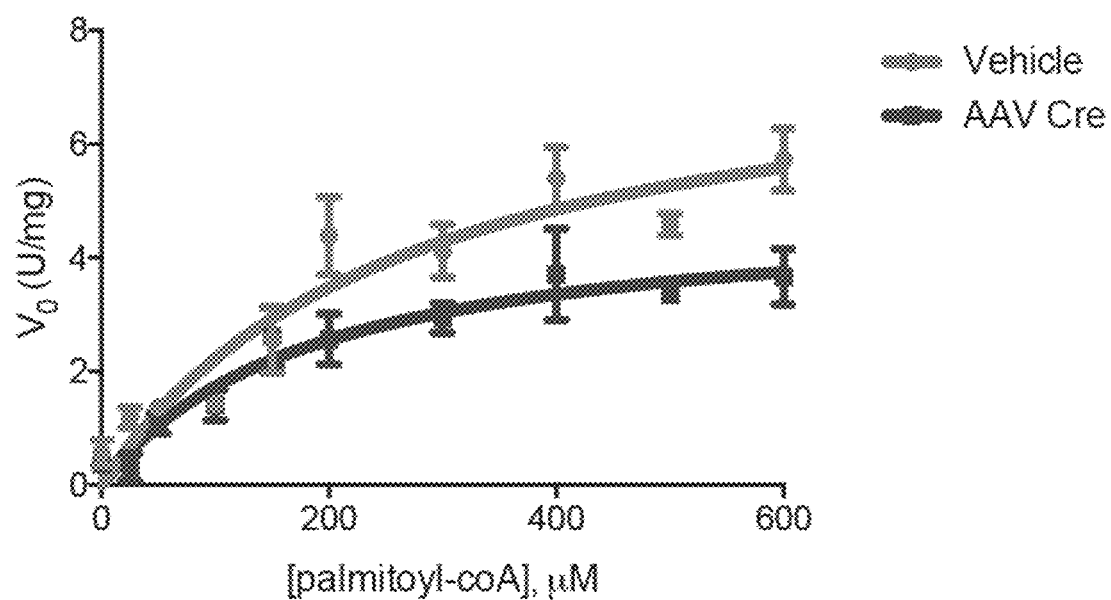
FIG. 30 is a graph depicting a VLCAD enzymatic activity assay of liver mitochondria in mice that undergo AAV.TBG.Cre-induced Mcl-1 deletion. Such mice manifest impaired VLCAD activity, consistent with the requirement of MCL-1 for homeostatic VLCAD function.

To investigate the effect of MCL-1 loss on VLCAD activity in vivo, an acute Mcl-1 knockout mouse model was used. Mcl-1$^{F/F}$ mice injected with an AAV.TBG.Cre adenovirus display hepatocyte-specific knockout of Mcl-1, as illustrated by anti-MCL-1 Western analysis of liver mitochondrial lysates (FIG. 29). In vitro VLCAD enzymatic assays were then performed on mitochondrial lysates from mice injected with either vehicle or Cre. Mice that underwent liver-targeted Mcl-1 deletion manifested impaired VLCAD activity, consistent with the requirement of MCL-1 for homeostatic VLCAD function (FIG. 30).

Figure 31:
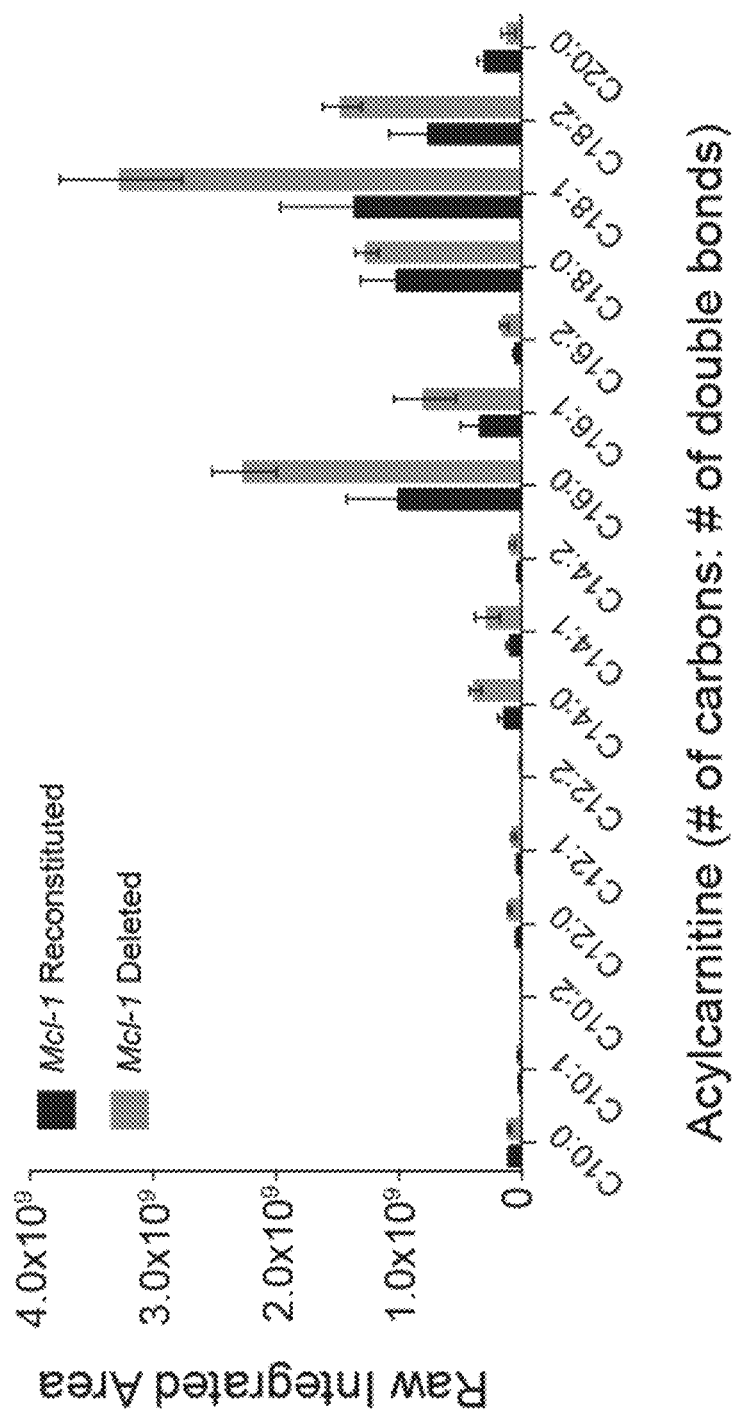
FIG. 31 shows elevated levels of long-chain fatty acylcarnitines in Mcl-1-deficient murine livers.

To further explore the physiologic relevance of the MCL-1/VLCAD interaction in vivo, we performed mass spectrometry-based acylcarnitine quantification on WT versus Mcl-1-deleted murine livers. Mcl-1$^{fl/fl}$ mice were injected with AAV-LP1-Cre viral constructs to delete Mcl-1 in a liver-specific fashion. The mice were then injected with either AAV-LP1-MCL-1 to reconstitute MCL-1 in livers, or with AAV-LP1-GFP as a negative control. Harvested livers were flash frozen, homogenized in acetonitrile and methanol to extract lipids, and extracts were then butylated and analyzed by LC-MS/MS. Consistent with our findings in MEFs, we observed elevation of long-chain acylcarnitines in livers lacking MCL-1 (FIG. 31).

Example 10: MCL-1 and VLCAD Interact Endogenously

Figure 32:
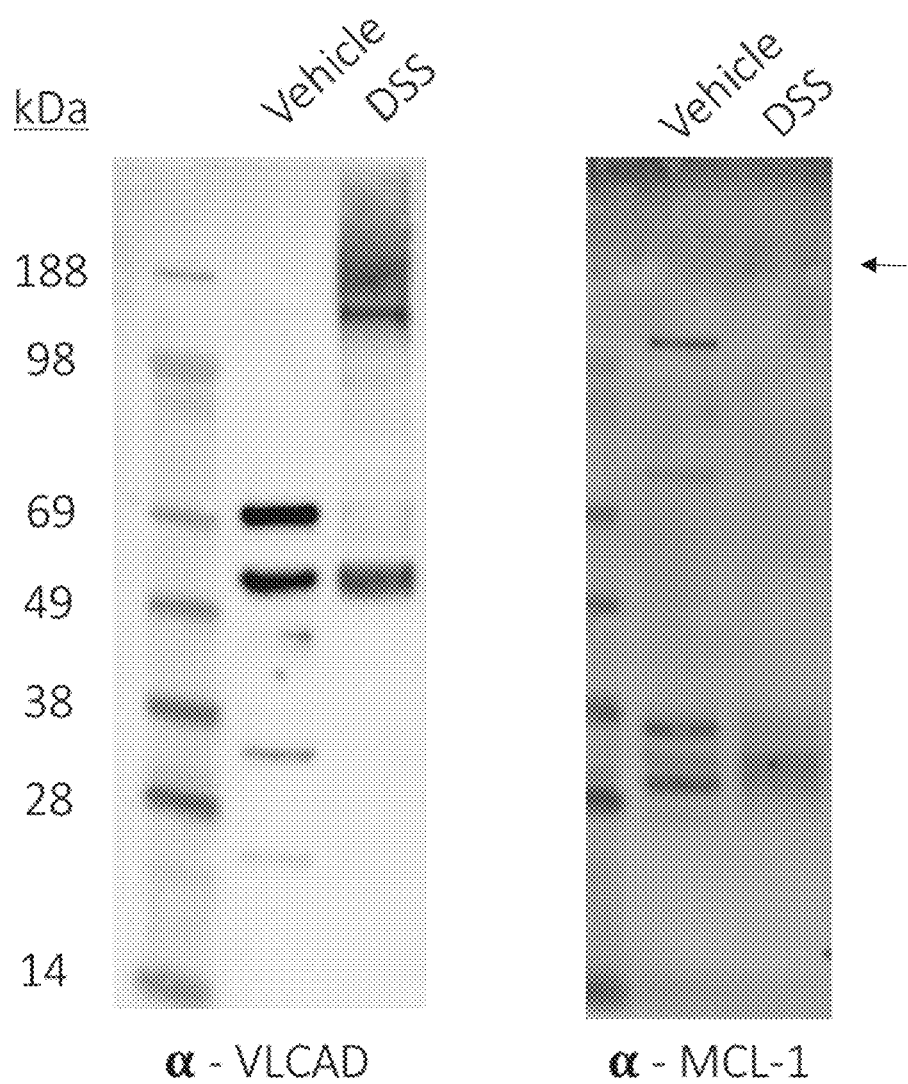
FIG. 32 is a Western blot showing that chemical cross-linking of intact mouse liver mitochondria results in a band at ~188 kDa that is detected both by anti-VLCAD and anti-MCL-1 antibodies, indicative of a native complex that contains both proteins.

To investigate the native interaction between VLCAD and MCL-1, intact mitochondria were isolated from mouse livers and exposed to the chemical crosslinker DSS. Vehicle or DSS-treated mitochondria were then lysed and the resultant lysate run on a reducing/denaturing gel. Both anti-VLCAD and anti-MCL-1 Western analysis revealed a band at ~188 kDa, indicative of a native complex that contains both proteins (FIG. 32).

Example 11: Loss of Mcl-1 Causes a Decrease in Cellular Proliferation

Figure 33:
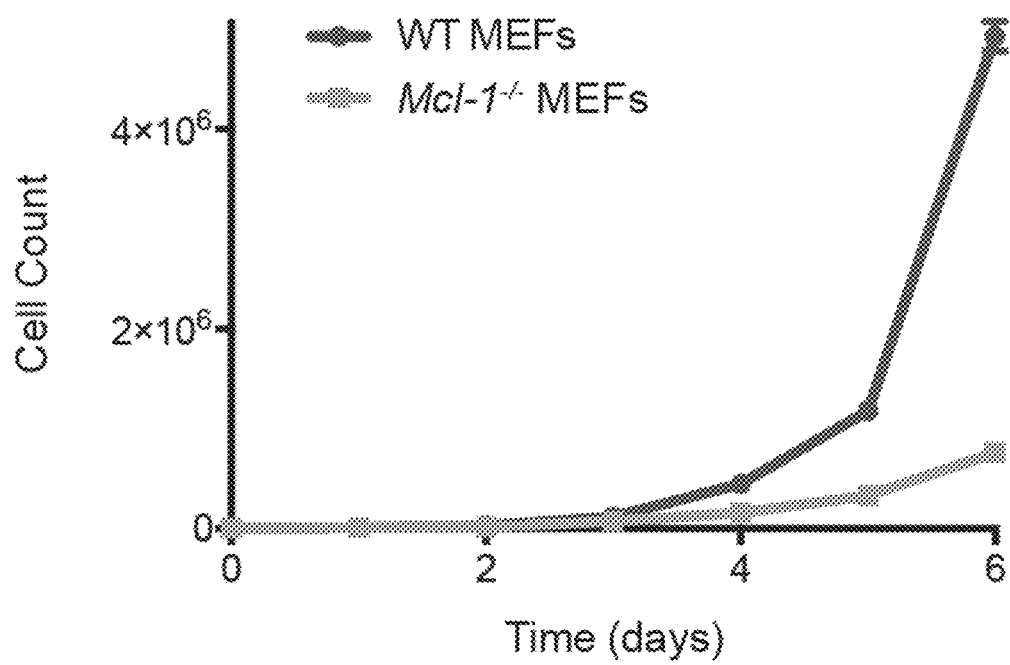
FIG. 33 is a graph showing that Mcl-1$^{-/-}$ MEFs display a decreased proliferation rate compared to wild-type MEFs, as demonstrated by serial cell counting.
Figure 34:
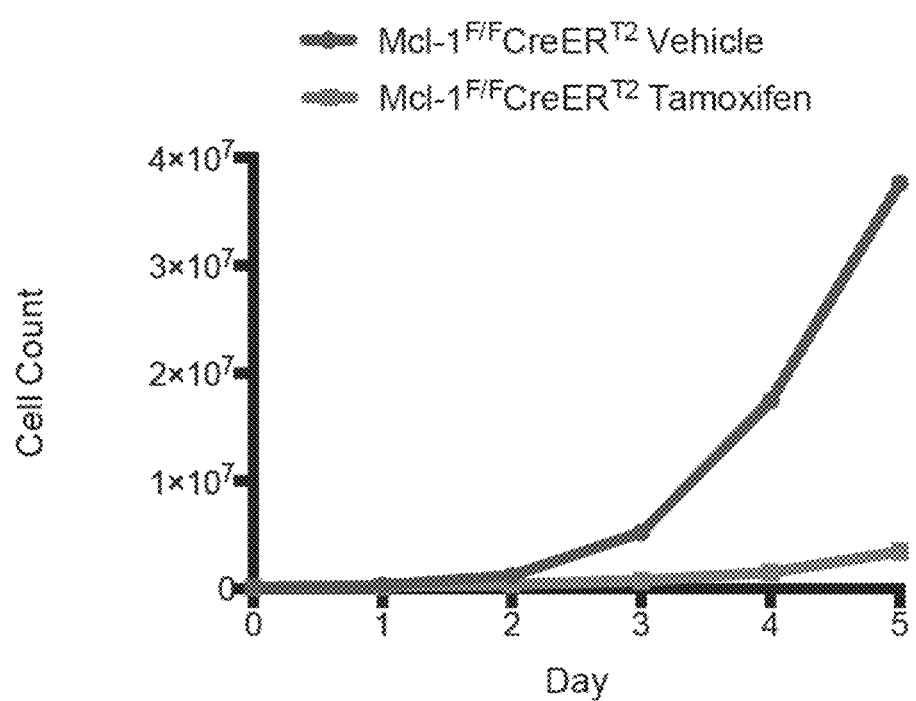
FIG. 34 is a graph showing that Mcl-1$^{F/F}$ CreER$^{T2}$ cells treated with tamoxifen, which results in acute Mcl-1 deletion, display a decreased proliferation rate compared to vehicle-treated cells, indicating that MEFs lacking MCL-1 have a decreased growth capacity.
Figure 35:
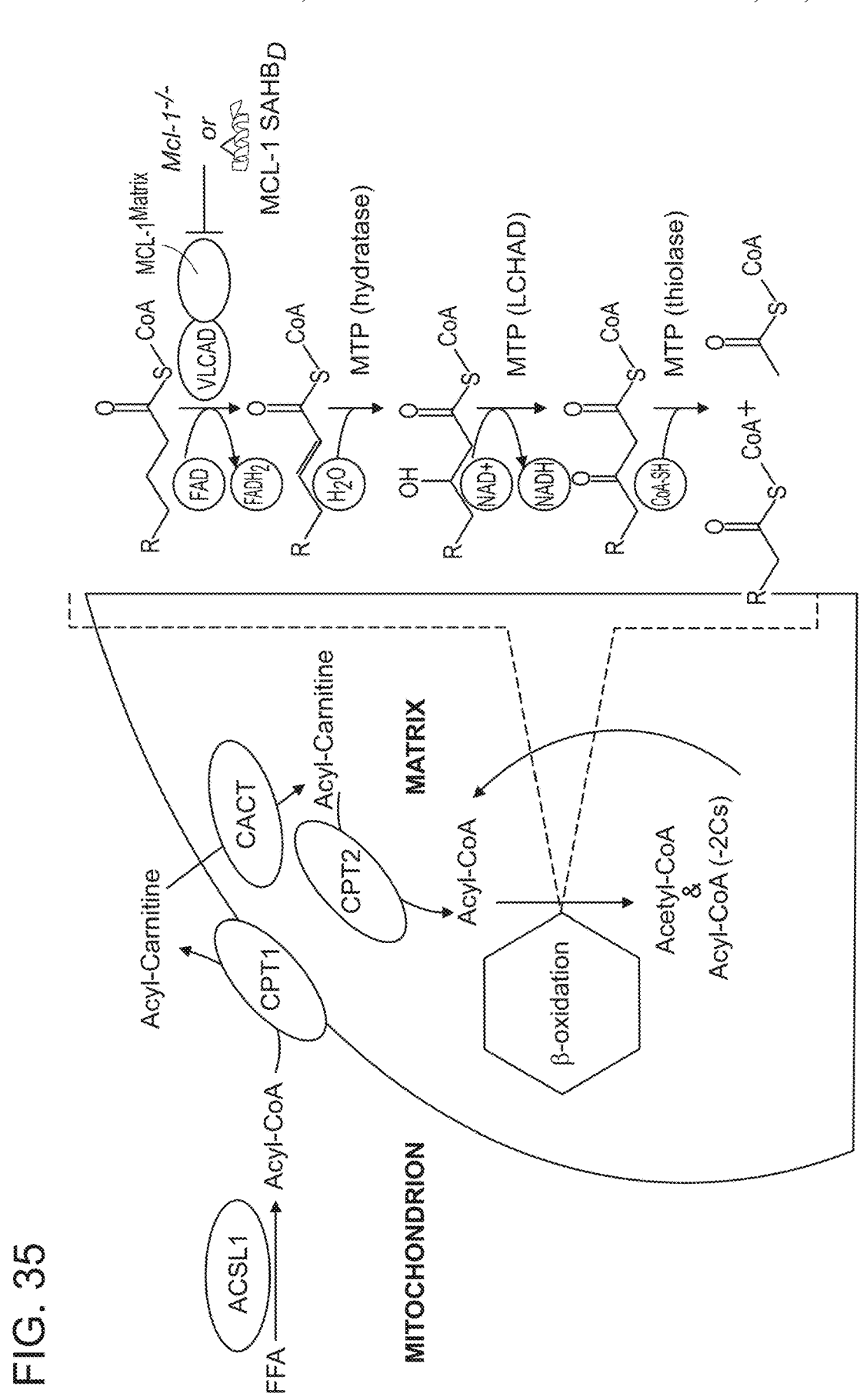
FIG. 35 is a schematic depicting the mitochondrial fatty acid β-oxidation pathway and the MCL-1 control point for VLCAD modulation.

Given the importance of fatty acid β-oxidation in fuel generation for stressed or starved cells, the effect of Mcl-1 deletion on a cell's proliferation rate was investigated. Cells were plated and subsequently counted daily as they expanded. Loss of Mcl-1 in both long-term (FIG. 33) and short-term (FIG. 34) contexts caused a marked decrease in cell proliferation. These results indicate that MCL-1 is required for cell growth and, in the context of cancer, can provide a growth advantage in the setting of cell stress and starvation, including during the metastatic spread of cancer. Thus, putting the brakes on the fatty acid β-oxidation pathway, e.g., by targeting the MCL-1/VLCAD interaction by administering to a subject in need thereof MCL-1 stapled peptides (e.g., SAHBs such as MCL-1 SAHB$_D$ or alanine mutants thereof (see FIG. 18A)) to disrupt the complex and thereby inhibit VLCAD activity can serve as a novel treatment for the wide variety of cancers that express MCL-1, or other conditions characterized by excessive fatty acid β-oxidation.

Example 12: Materials and Methods

Stapled Peptide Synthesis

Stapled peptides were synthesized, derivatized, purified by LC/MS to >95% homogeneity, and quantified by amino acid analysis using techniques known in the art (see, e.g., Bird, Curr Protoc Chem Biol. 2011, Bird, Meth Enzymol. 2008, Braun, Chem Biol. 2010). For CD analysis performed on an Aviv Biomedical spectrophotometer, SAHBs were dissolved in 50 mM potassium phosphate (pH 7.5) to a target final concentration of 50 μM (see, e.g., Bird, Meth Enzymol. 2008).

Cell Culture

SV-40-transformed wild-type, Mcl-1$^{-/-}$, Mcl-1$^{+/+}$CreER$^{T2}$, Mcl-1$^{F/F}$CreER$^{T2}$, Mcl-1$^{fl/fl}$CreER$^{T2}$+MCL-1$^{OMM}$, and Mcl-1$^{fl/fl}$CreER$^{T2}$+MCL-1$^{Matrix}$ have been described previously (see, e.g., Opferman, Nature, 426(6967):671-6 (2003), Perciavalle, Nat Cell Biol., 14(6):575-83 (2012)) and were kindly provided by Joseph Opferman (St. Jude Children's Research Hospital). All mouse embryonic fibroblasts (MEFs) were maintained in Dulbecco's modified Eagle's medium (DMEM) (Invitrogen) supplemented with 10% (v/v) fetal bovine serum, 100 U/ml penicillin/streptomycin, and 2 mM glutamine following standard culture conditions and procedures known in the art. To induce Cre expression, cells were treated with 100 nM (4-hydroxy)-tamoxifen (Sigma) in media for at least 48 hours. All cell lines were ensured to be mycoplasma-free using the MycoAlert™ mycoplasma detection kit (Lonza Biologics).

Biotinylated SAHB Pulldowns

Wild-type MEFs were trypsinized, washed once with cold PBS, and lysed on ice with NP-40 lysis buffer (50 mM Tris, pH 7.4, 150 mM NaCl, 0.5% (v/v) NP-40, complete protease inhibitor pellet (Roche)) using 1 ml of lysis buffer for every 10 million cells lysed. Cellular debris was pelleted at 14,000 g for 10 min at 4° C., and the supernatant was quantified using the BCA Protein Assay Kit (Thermo Fisher Scientific). 2 mg of lysate per pulldown were then exposed to 50 μL of pre-equilibrated High Capacity Streptavidin Agarose beads (Thermo Fisher Scientific). The pre-cleared lysates were then incubated with 15 nmol biotinylated SAHBs (or vehicle, 1.5% (v/v) DMSO) overnight at 4° C., followed by addition of 50 μL of pre-equilibrated High Capacity Streptavidin Agarose beads for 2 hours at 4° C. The beads were then pelleted and washed with NP-40 lysis buffer three times before eluting the protein sample from the beads by heating at 70° C. for 10 min in SDS loading buffer. Samples were then subjected to electrophoresis and either Western analysis or Coomassie stain (SimplyBlue Safe Stain, Thermo Fisher Scientific). The antibodies used for Western analysis were the following: MCL-1 (Rockland 600-401-394; 1:1000 in 3% BSA), VLCAD (Thermo Fisher Scientific PA5-29959; 1:1000 in 1% milk+0.1% Tween-20), MCAD (Thermo Fisher Scientific PA5-27201; 1:1000 in 3% BSA), and SCAD (Abcam ab154823; 1:1000 in 3% BSA). Coomassie stained gels were then processed for proteomics analysis (see below). Biotinylated SAHB pulldowns of recombinant protein were performed as above incubating 5 nmol of SAHB with 10 pmol of rVLCAD in 500 μL total volume. Densitometry analyses were performed using ImageJ software.

Mass Spectrometric Identification of MCL-1 SAHB Interactors

Each lane of Coomassie stained gels was divided into 8 sections and further cut into small 1 mm×1 mm cubes. Gel pieces were then destained in 50% acetonitrile/50 mM ammonium bicarbonate at 37° C. until destaining was complete (approximately 30 min). Gel pieces were then dehydrated by soaking in acetonitrile three times for 5 min at room temperature. In-gel trypsin digests were then performed on the gel pieces by submerging gel slices in 12.5 ng/μL solution of trypsin (Promega, sequencing grade) in 50 mM ammonium bicarbonate and incubating on ice for 45 min, followed by incubation at 37° C. overnight. Tryptic peptides were then extracted from the gel matrix by submerging the gel pieces in a 50% acetonitrile/5% formic acid solution two times for 15 min. The resulting extracts were then dried by SpeedVac™ (Thermo Scientific), purified through OMIX tips according to the manufacturer's instructions (Agilent Technologies), and dried again. Samples were then reconstituted in 4 μL of a 5% acetonitrile/5% formic acid solution and analyzed by LC-MS/MS on a Thermo Orbitrap Discovery as described (see, e.g., Braun 2010). Peptides were identified using both Thermo Protein Discoverer and Xtandem!algorithms and processed using Scaffold (Proteome Software).

Protein Expression

VLCAD. Mature human VLCAD lacking its cleavable leader sequence (aa 40-655) (NP_000009.1) was subcloned into the pET19b vector (Novagen) using NdeI and XhoI restriction sites. Correct insertion was confirmed by DNA sequencing. The 10× His-tagged VLCAD construct was expressed in BL21(DE3) $E.\ coli$, and once cells reached an OD of 0.8 after growing at 37° C., they were induced with 0.5 mM isopropylthio-β-galactosidase (IPTG) (Gold Biotechnology I2481C) at 37° C. for 4 hours. Bacterial pellets were resuspended in lysis buffer (500 mM NaCl, 50 mM HEPES, 5% glycerol, pH 7.5, complete protease inhibitor tablet) and lysed by microfluidization (M-110L; Microfluidics). Cell lysates were then cleared by centrifugation at 20,000 rpm for 45 min (Beckman Avanti J-E, rotor type JA-20). Cleared cellular lysates were then subjected to Ni-NTA (QIAGEN) affinity chromatography, followed by elution with 300 mM imidazole (Sigma 12399) and overnight dialysis at 4° C. Dialyzed VLCAD was then concentrated and subjected to size exclusion chromatography (GE Healthcare Life Sciences Superdex 200 10/300 GL) at 4° C. using 150 mM NaCl, 50 mM Tris, pH 8.0. Protein was used upon isolation and was stored at 4° C. for up to two weeks. Successful protein production was confirmed by SDS-PAGE, Western blot, intact MS, and enzymatic activity assay.

MCL-1ΔNΔC. The MCL-1ΔNΔC construct was grown and expressed in $E.\ coli$ as previously described (see, e.g., Stewart, Nat Chem Biol., 6(6):595-601 (2010)). Transformed BL21(DE3) $E.\ coli$ were grown at 37° C. to an OD of 0.8, after which they were induced with 0.5 mM IPTG. Bacterial pellets were resuspended in lysis buffer (PBS with 1% (v/v) Triton X-100, complete protease inhibitor tablet) and lysed by microfluidization. Cell lysates were then cleared by centrifugation at 20,000 rpm for 45 min. Cleared cellular lysates were then subjected to glutathione sepharose (GE Healthcare) affinity chromatography, followed by cleavage from the column by overnight incubation with thrombin in PBS. Protein was then concentrated and subjected to size exclusion chromatography (GE Healthcare Life Sciences Superdex 75 10/300 GL) at 4° C. using 150 mM NaCl, 50 mM Tris, pH 7.4.

$^{19}$F NMR

To determine binding of SAHBs to VLCAD, fluorinated SAHB (25 μM) and VLCAD (0-125 μM) were mixed together in VLCAD FPLC buffer including 10% $D_2O$ to a final volume of 500 μL. Samples were run on a Bruker Avance-III NMR Spectrometer operating at 500 MHz using a room temperature fluorine inner-coil probe, using a pulse sequence that allows direct observation of $^{19}$F resonances in the presence of $^1$H decoupling. Fluorine resonances were typically in the −60 to −65 ppm range. The extent to which VLCAD bound the peptide was determined by measuring the peak width at half height ($v_{1/2}$) of the peptide $^{19}$F signal. To determine binding of SAHBs to MCL-1ΔNΔC, fluorinated SAHB (25 μM) and MCL-1ΔNΔC (0-45 μM) were mixed together in MCL-1ΔNΔC FPLC buffer including 10% $D_2O$ to a final volume of 500 μL and run as described above. MCL-1ΔNΔC binding to SAHBs causes a change in the $^{19}$F chemical shift of the peptide resulting in two peptide signals (instead of peak broadening), so extent of binding was quantified by measuring the peak height of "unbound" peptide relative to the bound peptide signal.

Biolayer Interferometry

BLI binding measurements were performed using an Octet Red384 System (ForteBio). Super streptavidin (SSA) sensors were pre-soaked in VLCAD FPLC buffer for at least 10 minutes prior to use, loaded with 5 μg/mL Biotin-PEG-MCL-1 SAHB$_D$ or Biotin-PEG-MCL-1 SAHB$_B$ peptides for 400 sec, quenched with 0.1 mg/mL biocytin for 120 sec, and washed with buffer for 120 sec. The sensors were then transferred into serial dilutions of VLCAD (association step), followed by buffer alone (dissociation step). Negative control runs were performed in parallel as above except that no Biotin-PEG peptide was loaded onto the sensors. These served as reference sensors for the analysis. Binding parameters were calculated using the accompanying Octet Software version 9 (ForteBio).

Isothermal Calorimetry

A peptide enthalpy screen was performed by adding 80 μM of recombinant VLCAD to the cell in analysis buffer (20 mM HEPES, pH 7.5, 150 mM NaCl, 1 mM TCEP, and 1% DMSO), followed by injection of 2.0 μL of 100 μM peptide by syringe, using an Affinity ITC (TA instruments) at 25° C. Injections were performed in technical triplicate for each peptide. Binding affinity of Btn-MCL-1 SAHB$_D$ V220A was measured by adding 15 μM of recombinant VLCAD to the cell in analysis buffer (as above, except that 2% DMSO was employed), followed by injection of 2.0 μL of 200 μM peptide by syringe for a total of 24 injections. Data were analyzed with the NanoAnalyze software package (TA instruments) using a single binding site model and thermodynamic parameters calculated as follows: $\Delta G = \Delta H - T\Delta S = -RT\ln K_B$, where $\Delta G$, $\Delta H$, and $\Delta S$ are the changes in free energy, enthalpy and entropy of binding, respectively.

Affinity Labeling and Binding Site Analysis

Recombinant VLCAD protein (10 M) and biotinylated MCL-1 pSAHB (40 μM) were mixed in 3 mL of VLCAD FPLC buffer, incubated at 4° C. overnight, and irradiated (365 nm, Spectroline Handheld UV Lamp Model En280L, Spectronics) for 2 hours on ice. Unreacted peptide was removed by overnight dialysis at 4° C. using 10 kDa molecular-weight cutoff Slide-A-Lyzer™ dialysis cassettes (Thermo Fisher). Biotinylated species were captured by incubating the reaction mixture with high-capacity streptavidin agarose beads for 2 hours at 4° C. On-bead trypsin digestion was performed by incubating the beads at 60° C. for 30 minutes in 100 μL of 50 mM ammonium bicarbonate, 5 mM DTT, and 0.1% Rapigest (Waters), followed by the addition of trypsin (0.1 g) for overnight treatment at 37° C. To remove uncrosslinked VLCAD peptides, the beads were then washed at room temperature three times each in 1% SDS in PBS, 1 M NaCl in PBS, and 10% ethanol in PBS. Biotinylated species were eluted by incubating the beads in a 50% acetonitrile/0.1% TFA solution for 2 minutes at 65° C. MCL-1 pSAHBD3-crosslinked samples were captured on streptavidin beads, washed and eluted as above, and then subjected to in-solution digestion. Samples were then purified through OMIX tips and analyzed using a Thermo Orbitrap Discovery mass spectrometer. To ensure efficient covalent capture by the biotinylated pSAHBs, samples were subjected to electrophoresis and anti-biotin western analysis (Abcam 53494; 1:1000 in 3% BSA).

Mice

Genotyping was performed by Transnetyx. Mice were euthanized by $CO_2$ asphyxiation. All animal experiments were performed in accordance with NIH guidelines and approved by the Dana-Farber Cancer Institute (DFCI) Institutional Animal Care and Use Committee (IACUC).

Mouse Techniques

Hepatocyte-specific deletion of Mcl-1 from Mcl-1$^{fl/fl}$ mice was achieved through retro-orbital injection of AAV8.TBG.PI.Cre.rBG adenoviral particles (Penn Vector Core) at a titer of 1*10$^{11}$/mL (or PBS vehicle control). Sex-matched littermates served as controls whenever possible; otherwise, age-matched and sex-matched animals served as controls. Livers were then harvested after at least 72 hours following injection for mitochondrial isolation as previously described (see, e.g., Walensky, Mol Cell, 24(2): 199-210, (2006), Pitter, Meth Enzymol., 446:387-408, (2008)). To increase fatty acid respiration above baseline, mice were fasted for 24 hours starting 72 hours post-injection.

VLCAD Enzymatic Activity Assay

VLCAD enzymatic activity was measured as previously described (see, e.g., Doulias et al., Sci Signal, 6(256):rs1 (2013); Lehman et al., Anal. Biochem., 186(2):280-284 (1990)). Briefly, ferrocenium hexafluorophosphate (Sigma-Aldrich) was dissolved in 10 mM HCl to a concentration of 1 mM and further diluted to a final concentration of 150 μM in 100 mM potassium phosphate buffer pH 7.2 containing 0.1 mM EDTA and palmitoyl-CoA or hexanoyl-CoA (final concentration ranging from 15 μM to 600 μM) (Sigma-Aldrich). The reaction was initiated by addition of purified recombinant VLCAD protein (final concentration of 0.75 μM) or mouse liver mitochondria homogenate (final concentration of 0.5 μg/μl). Where VLCAD activity was assessed in the presence of MCL-1 SAHBs, 0.75 μM VLCAD was incubated overnight at 4° C. with 75 μM SAHB and the protein-peptide mixture was used to initiate the ferrocenium reaction. Decrease in ferrocenium absorbance as a function of time at 300 nm was recorded and the initial velocity ($V_0$) was calculated in units of U/mg using the molar absorptivity of ferrocenium ($\varepsilon$=4.3 mM$^{-1}$ cm$^{-1}$ at 300 nm) (see, e.g., Izai et al.). Ten concentrations of substrate were used to determine the apparent $V_{max}$ and $K_M$ of VLCAD in each experimental condition, using the Michaelis-Menten non-linear regression with least-squares fit in Prism 6.0 (GraphPad).

Acylcarnitine Analysis

Vehicle or tamoxifen-treated Mcl-1$^{F/F}$CreER$^{T2}$ cells were plated in DMEM containing 200 μM palmitate and 400 μM L-carnitine for 96 hours (see, e.g., Shen et al.). Cells were then trypsinized, washed with cold PBS, and flash frozen in liquid nitrogen. Frozen pellets were thawed in 1 mL of a 3:1 acetonitrile:methanol solution containing 0.1 μM palmitic acid-$^{13}$C (Sigma) as an internal standard. Once thawed, cells were thoroughly resuspended by two rounds of vortexing and sonication of 30 sec each. Debris was pelleted at 12,000 g for 10 min, after which the supernatant was transferred to a clean tube and dried under nitrogen at 45° C. Acylcarnitine species were then butylated by the addition of 100 μL acetyl chloride (Sigma) and 400 μL of 1-butanol (Sigma) for 15 min at 60° C. Samples were then dried again under nitrogen at 45° C., resuspended in 100% acetonitrile and ran on a q-Exactive Plus coupled to a Thermo Ultimate 3000 uHPLC (see, e.g., Chegary et al.). Data was analyzed using the Xcalibur Qual Browser (Thermo v3.0.63). For peptide treatment experiments, 10 μM MCL-1 SAHB was added to the palmitate-containing DMEM for the last 48 hours of the 96-hour total incubation.

For acylcarnitine analysis in livers, frozen tissue was thawed in 750 L of a 3:1 acetonitrile:methanol solution containing 0.1 M $^{13}$C-palmitic acid (Sigma-Aldrich) as an internal standard. Once thawed, tissue was homogenized thoroughly with an IKA T10 Basic homogenizer. Cellular debris was then pelleted at 12,000×g for 10 minutes and further processed and analyzed as described above.

Cell Growth Assay 5000 cells per well were plated in a 100 μL volume in a 96-well plate. For the following 5-6 days, cells were trypsinized, counted, and re-plated in an appropriately-sized well based on the number of cells present.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 70
SEQ ID NO: 1            moltype = AA  length = 350
FEATURE                 Location/Qualifiers
source                  1..350
                        mol_type = protein
                        organism = Homo sapiens
SEQUENCE: 1
MFGLKRNAVI GLNLYCGGAG LGAGSGGATR PGGRLLATEK EASARREIGG GEAGAVIGGS   60
AGASPPSTLT PDSRRVARPP PIGAEVPDVT ATPARLLFFA PTRRAAPLEE MEAPAADAIM  120
SPEEELDGYE PEPLGKRPAV LPLLELVGES GNNTSTDGSL PSTPPPAEEE EDELYRQSLE  180
IISRYLREQA TGAKDTKPMG RSGATSRKAL ETLRRVGDGV QRNHETAFQG MLRKLDIKNE  240
DDVKSLSRVM IHVFSDGVTN WGRIVTLISF GAFVAKHLKT INQESCIEPL AESITDVLVR  300
TKRDWLVKQR GWDGFVEFFH VEDLEGGIRN VLLAFAGVAG VGAGLAYLIR             350

SEQ ID NO: 2            moltype = AA  length = 331
FEATURE                 Location/Qualifiers
source                  1..331
                        mol_type = protein
```

```
                        organism = Mus sp.
SEQUENCE: 2
MFGLRRNAVI GLNLYCGGAS LGAGGGSPAG ARLVAEEEAKA RREGGGEAAL LPGARVVARP     60
PPVGAEDPDV TASAERRLHK SPGLLAVPPE EMAASAAAAI VSPEEELDGC EPEAIGKRPA     120
VLPLLERVSE AAKSSGADGS LPSTPPPPEE EDDLYRQSL EIISRYLREQ ATGSKDSKPL      180
GEAGAAGRRA LETLRRVGDG VQRNHETAFQ GMLRKLDIKN EGDVKSFSRV MVHVFKDGVT     240
NWGRIVTLIS FGAFVAKHLK SVNQESFIEP LAETITDVLV RTKRDWLVKQ RGWDGFVEFF     300
HVQDLEGGIR NVLLAFAGVA GVGAGLAYLI R                                   331

SEQ ID NO: 3            moltype = AA   length = 299
FEATURE                 Location/Qualifiers
source                  1..299
                        mol_type = protein
                        organism = Mus sp.
SEQUENCE: 3
LVAEEEAKARR EGGGEAALLP GARVVARPPP VGAEDPDVTA SAERRLHKSP GLLAVPPEEM    60
AASAAAAIVS PEEELDGCEP EAIGKRPAVL PLLERVSEAA KSSGADGSLP STPPPPEEEE    120
DDLYRQSLEI ISRYLREQAT GSKDSKPLGE AGAAGRRALE TLRRVGDGVQ RNHETAFQGM    180
LRKLDIKNEG DVKSFSRVMV HVFKDGVTNW GRIVTLISFG AFVAKHLKSV NQESFIEPLA    240
ETITDVLVRT KRDWLVKQRG WDGFVEFFHV QDLEGGIRNV LLAFAGVGAV GAGLAYLIR    299

SEQ ID NO: 4            moltype = AA   length = 316
FEATURE                 Location/Qualifiers
source                  1..316
                        mol_type = protein
                        organism = Homo sapiens
SEQUENCE: 4
LLATEKEASA RREIGGGEAG AVIGGSAGAS PPSTLTPDSR RVARPPPIGA EVPDVTATPA     60
RLLFFAPTRR AAPLEEMEAP AADAIMSPEE ELDGYEPEPL GKRPAVLPLL ELVGESGNNT    120
STDGSLPSTP PPAEEEEDEL YRQSLEIISR YLREQATGAK DTKPMGRSGA TSRKALETLR    180
RVGDGVQRNH ETAFQGMLRK LDIKNEDDVK SLSRVMIHVF SDGVTNWGRI VTLISFGAFV    240
AKHLKTINQE SCIEPLAESI TDVLVRTKRD WLVKQRGWDG FVEFFHVEDL EGGIRNVLLA    300
FAGVAGVGAG LAYLIR                                                   316

SEQ ID NO: 5            moltype = AA   length = 22
FEATURE                 Location/Qualifiers
MOD_RES                 1
                        note = S-pentenyl alanine
MOD_RES                 5
                        note = S-pentenyl alanine
source                  1..22
                        mol_type = protein
                        organism = synthetic construct
SEQUENCE: 5
AKALATLRRV GDGVQRNHET AF                                             22

SEQ ID NO: 6            moltype = AA   length = 22
FEATURE                 Location/Qualifiers
MOD_RES                 2
                        note = S-pentenyl alanine
MOD_RES                 6
                        note = S-pentenyl alanine
source                  1..22
                        mol_type = protein
                        organism = synthetic construct
SEQUENCE: 6
RAALEALRRV GDGVQRNHET AF                                             22

SEQ ID NO: 7            moltype = AA   length = 22
FEATURE                 Location/Qualifiers
MOD_RES                 3
                        note = S-pentenyl alanine
MOD_RES                 7
                        note = S-pentenyl alanine
source                  1..22
                        mol_type = protein
                        organism = synthetic construct
SEQUENCE: 7
RKALETARRV GDGVQRNHET AF                                             22

SEQ ID NO: 8            moltype = AA   length = 22
FEATURE                 Location/Qualifiers
MOD_RES                 4
                        note = S-pentenyl alanine
MOD_RES                 8
                        note = S-pentenyl alanine
source                  1..22
                        mol_type = protein
                        organism = synthetic construct
```

```
SEQUENCE: 8
RKAAETLARV GDGVQRNHET AF                                                        22

SEQ ID NO: 9             moltype = AA  length = 22
FEATURE                  Location/Qualifiers
MOD_RES                  5
                         note = S-pentenyl alanine
MOD_RES                  9
                         note = S-pentenyl alanine
source                   1..22
                         mol_type = protein
                         organism = synthetic construct
SEQUENCE: 9
RKALATLRAV GDGVQRNHET AF                                                        22

SEQ ID NO: 10            moltype = AA  length = 22
FEATURE                  Location/Qualifiers
MOD_RES                  6
                         note = S-pentenyl alanine
MOD_RES                  10
                         note = S-pentenyl alanine
source                   1..22
                         mol_type = protein
                         organism = synthetic construct
SEQUENCE: 10
RKALEALRRA GDGVQRNHET AF                                                        22

SEQ ID NO: 11            moltype = AA  length = 22
FEATURE                  Location/Qualifiers
MOD_RES                  7
                         note = S-pentenyl alanine
MOD_RES                  11
                         note = S-pentenyl alanine
source                   1..22
                         mol_type = protein
                         organism = synthetic construct
SEQUENCE: 11
RKALETARRV ADGVQRNHET AF                                                        22

SEQ ID NO: 12            moltype = AA  length = 22
FEATURE                  Location/Qualifiers
MOD_RES                  8
                         note = S-pentenyl alanine
MOD_RES                  12
                         note = S-pentenyl alanine
source                   1..22
                         mol_type = protein
                         organism = synthetic construct
SEQUENCE: 12
RKALETLARV GAGVQRNHET AF                                                        22

SEQ ID NO: 13            moltype = AA  length = 22
FEATURE                  Location/Qualifiers
MOD_RES                  9
                         note = S-pentenyl alanine
MOD_RES                  13
                         note = S-pentenyl alanine
source                   1..22
                         mol_type = protein
                         organism = synthetic construct
SEQUENCE: 13
RKALETLRAV GDAVQRNHET AF                                                        22

SEQ ID NO: 14            moltype = AA  length = 22
FEATURE                  Location/Qualifiers
MOD_RES                  10
                         note = S-pentenyl alanine
MOD_RES                  14
                         note = S-pentenyl alanine
source                   1..22
                         mol_type = protein
                         organism = synthetic construct
SEQUENCE: 14
RKALETLRRA GDGAQRNHET AF                                                        22

SEQ ID NO: 15            moltype = AA  length = 22
FEATURE                  Location/Qualifiers
MOD_RES                  11
                         note = S-pentenyl alanine
```

```
MOD_RES                 15
                        note = S-pentenyl alanine
source                  1..22
                        mol_type = protein
                        organism = synthetic construct
SEQUENCE: 15
RKALETLRRV ADGVARNHET AF                                               22

SEQ ID NO: 16           moltype = AA  length = 22
FEATURE                 Location/Qualifiers
MOD_RES                 12
                        note = S-pentenyl alanine
MOD_RES                 16
                        note = S-pentenyl alanine
source                  1..22
                        mol_type = protein
                        organism = synthetic construct
SEQUENCE: 16
RKALETLRRV GAGVQANHET AF                                               22

SEQ ID NO: 17           moltype = AA  length = 22
FEATURE                 Location/Qualifiers
MOD_RES                 13
                        note = S-pentenyl alanine
MOD_RES                 17
                        note = S-pentenyl alanine
source                  1..22
                        mol_type = protein
                        organism = synthetic construct
SEQUENCE: 17
RKALETLRRV GDAVQRAHET AF                                               22

SEQ ID NO: 18           moltype = AA  length = 22
FEATURE                 Location/Qualifiers
MOD_RES                 14
                        note = S-pentenyl alanine
MOD_RES                 18
                        note = S-pentenyl alanine
source                  1..22
                        mol_type = protein
                        organism = synthetic construct
SEQUENCE: 18
RKALETLRRV GDGAQRNAET AF                                               22

SEQ ID NO: 19           moltype = AA  length = 22
FEATURE                 Location/Qualifiers
MOD_RES                 15
                        note = S-pentenyl alanine
MOD_RES                 19
                        note = S-pentenyl alanine
source                  1..22
                        mol_type = protein
                        organism = synthetic construct
SEQUENCE: 19
RKALETLRRV GDGVARNHAT AF                                               22

SEQ ID NO: 20           moltype = AA  length = 22
FEATURE                 Location/Qualifiers
MOD_RES                 16
                        note = S-pentenyl alanine
MOD_RES                 20
                        note = S-pentenyl alanine
source                  1..22
                        mol_type = protein
                        organism = synthetic construct
SEQUENCE: 20
RKALETLRRV GDGVQANHEA AF                                               22

SEQ ID NO: 21           moltype = AA  length = 22
FEATURE                 Location/Qualifiers
MOD_RES                 17
                        note = S-pentenyl alanine
MOD_RES                 21
                        note = S-pentenyl alanine
source                  1..22
                        mol_type = protein
                        organism = synthetic construct
SEQUENCE: 21
RKALETLRRV GDGVQRAHET AF                                               22
```

```
SEQ ID NO: 22              moltype = AA   length = 22
FEATURE                    Location/Qualifiers
MOD_RES                    18
                           note = S-pentenyl alanine
MOD_RES                    22
                           note = S-pentenyl alanine
source                     1..22
                           mol_type = protein
                           organism = synthetic construct
SEQUENCE: 22
RKALETLRRV GDGVQRNAET AA                                                     22

SEQ ID NO: 23              moltype = AA   length = 22
FEATURE                    Location/Qualifiers
MOD_RES                    1
                           note = R-octenyl alanine
MOD_RES                    8
                           note = S-pentenyl alanine
source                     1..22
                           mol_type = protein
                           organism = synthetic construct
SEQUENCE: 23
AKALETLARV GDGVQRNHET AF                                                     22

SEQ ID NO: 24              moltype = AA   length = 22
FEATURE                    Location/Qualifiers
MOD_RES                    2
                           note = R-octenyl alanine
MOD_RES                    9
                           note = S-pentenyl alanine
source                     1..22
                           mol_type = protein
                           organism = synthetic construct
SEQUENCE: 24
RAALETLRAV GDGVQRNHET AF                                                     22

SEQ ID NO: 25              moltype = AA   length = 22
FEATURE                    Location/Qualifiers
MOD_RES                    3
                           note = R-octenyl alanine
MOD_RES                    10
                           note = S-pentenyl alanine
source                     1..22
                           mol_type = protein
                           organism = synthetic construct
SEQUENCE: 25
RKALETLRRA GDGVQRNHET AF                                                     22

SEQ ID NO: 26              moltype = AA   length = 22
FEATURE                    Location/Qualifiers
MOD_RES                    4
                           note = R-octenyl alanine
MOD_RES                    11
                           note = S-pentenyl alanine
source                     1..22
                           mol_type = protein
                           organism = synthetic construct
SEQUENCE: 26
RKAAETLRRV ADGVQRNHET AF                                                     22

SEQ ID NO: 27              moltype = AA   length = 22
FEATURE                    Location/Qualifiers
MOD_RES                    5
                           note = R-octenyl alanine
MOD_RES                    12
                           note = S-pentenyl alanine
source                     1..22
                           mol_type = protein
                           organism = synthetic construct
SEQUENCE: 27
RKALATLRRV GAGVQRNHET AF                                                     22

SEQ ID NO: 28              moltype = AA   length = 22
FEATURE                    Location/Qualifiers
MOD_RES                    6
                           note = R-octenyl alanine
MOD_RES                    13
                           note = S-pentenyl alanine
```

```
source                  1..22
                        mol_type = protein
                        organism = synthetic construct
SEQUENCE: 28
RKALEALRRV GDAVQRNHET AF                                                22

SEQ ID NO: 29           moltype = AA  length = 22
FEATURE                 Location/Qualifiers
MOD_RES                 7
                        note = R-octenyl alanine
MOD_RES                 14
                        note = S-pentenyl alanine
source                  1..22
                        mol_type = protein
                        organism = synthetic construct
SEQUENCE: 29
RKALETARRV GDGAQRNHET AF                                                22

SEQ ID NO: 30           moltype = AA  length = 22
FEATURE                 Location/Qualifiers
MOD_RES                 8
                        note = R-octenyl alanine
MOD_RES                 15
                        note = S-pentenyl alanine
source                  1..22
                        mol_type = protein
                        organism = synthetic construct
SEQUENCE: 30
RKALETLARV GDGVARNHET AF                                                22

SEQ ID NO: 31           moltype = AA  length = 22
FEATURE                 Location/Qualifiers
MOD_RES                 9
                        note = R-octenyl alanine
MOD_RES                 16
                        note = S-pentenyl alanine
source                  1..22
                        mol_type = protein
                        organism = synthetic construct
SEQUENCE: 31
RKALETLRAV GDGVQANHET AF                                                22

SEQ ID NO: 32           moltype = AA  length = 22
FEATURE                 Location/Qualifiers
MOD_RES                 10
                        note = R-octenyl alanine
MOD_RES                 17
                        note = S-pentenyl alanine
source                  1..22
                        mol_type = protein
                        organism = synthetic construct
SEQUENCE: 32
RKALETLRRA GDGVQRAHET AF                                                22

SEQ ID NO: 33           moltype = AA  length = 22
FEATURE                 Location/Qualifiers
MOD_RES                 11
                        note = R-octenyl alanine
MOD_RES                 18
                        note = S-pentenyl alanine
source                  1..22
                        mol_type = protein
                        organism = synthetic construct
SEQUENCE: 33
RKALETLRRV ADGVQRNAET AF                                                22

SEQ ID NO: 34           moltype = AA  length = 22
FEATURE                 Location/Qualifiers
MOD_RES                 12
                        note = R-octenyl alanine
MOD_RES                 19
                        note = S-pentenyl alanine
source                  1..22
                        mol_type = protein
                        organism = synthetic construct
SEQUENCE: 34
RKALETLRRV GAGVQRNHAT AF                                                22

SEQ ID NO: 35           moltype = AA  length = 22
```

| FEATURE | Location/Qualifiers |
|---|---|
| MOD_RES | 13 |
| | note = R-octenyl alanine |
| MOD_RES | 20 |
| | note = S-pentenyl alanine |
| source | 1..22 |
| | mol_type = protein |
| | organism = synthetic construct |

SEQUENCE: 35
RKALETLRRV GDAVQRNHEA AF                                                    22

| SEQ ID NO: 36 | moltype = AA  length = 22 |
|---|---|
| FEATURE | Location/Qualifiers |
| MOD_RES | 14 |
| | note = R-octenyl alanine |
| MOD_RES | 21 |
| | note = S-pentenyl alanine |
| source | 1..22 |
| | mol_type = protein |
| | organism = synthetic construct |

SEQUENCE: 36
RKALETLRRV GDGAQRNHET AF                                                    22

| SEQ ID NO: 37 | moltype = AA  length = 22 |
|---|---|
| FEATURE | Location/Qualifiers |
| MOD_RES | 15 |
| | note = R-octenyl alanine |
| MOD_RES | 22 |
| | note = S-pentenyl alanine |
| source | 1..22 |
| | mol_type = protein |
| | organism = synthetic construct |

SEQUENCE: 37
RKALETLRRV GDGVARNHET AA                                                    22

| SEQ ID NO: 38 | moltype = AA  length = 616 |
|---|---|
| FEATURE | Location/Qualifiers |
| source | 1..616 |
| | mol_type = protein |
| | organism = Mus sp. |

SEQUENCE: 38
YAREATQAVL DKPETLSSDA STREKPARAE SKSFAVGMFK GQLTIDQVFP YPSVLSEEQA     60
QFLKELVGPV ARFFEEVNDP AKNDALEKVE DDTLQGLKEL GAFGLQVPSE LGGLGLSNTQ    120
YARLAEIVGM HDLGVSVTLG AHQSIGFKGI LLYGTKAQRE KYLPRVASGQ ALAAFCLTEP    180
SSGSDVASIR SSAIPSPCGK YYTLNGSKIW ISNGGLADIF TVFAKTPIKD AATGAVKEKI    240
TAFVVERSFG GVTHGLPEKK MGIKASNTSE VYFDGVKVPS ENVLGEVGDG FKVAVNILNN    300
GRFGMAATLA GTMKSLIAKA VDHATNRTQF GDKIHNFGVI QEKLARMAIL QYVTESMAYM    360
LSANMDQGFK DFQIEAAISK IFCSEAAWKV ADECIQIMGG MGFMKEPGVE RVLRDIRIFR    420
IFEGANDILR LFVALQGCMD KGKELTGLGN ALKNPFGNVG LLMGEAGKQL RRRTGIGSGL    480
SLSGIVHPEL SRSGELAVQA LDQFATVVEA KLVKHKKGIV NEQFLLQRLA DGAIDLYAMV    540
VVLSRASRSL SEGYPTAQHE KMLCDSWCIE AATRIRENMA SLQSSPQHQE LFRNFRSISK    600
AMVENGGLVT GNPLGI                                                    616

| SEQ ID NO: 39 | moltype = AA  length = 655 |
|---|---|
| FEATURE | Location/Qualifiers |
| source | 1..655 |
| | mol_type = protein |
| | organism = Homo sapiens |

SEQUENCE: 39
MQAARMAASL GRQLLRLGGG SSRLTALLGQ PRPGPARRPY AGGAAQLALD KSDHPSDAL     60
TRKKPAKAES KSFAVGMFKG QLTTDQVFPY PSVLNEEQTQ FLKELVEPVS RFFEEVNDPA    120
KNDALEMVEE TTWQGLKELG AFGLQVPSEL GGVGLCNTQY ARLVEIVGMH DLGVGITLGA    180
HQSIGFKGIL LFGTKAQKEK YLPKLASGET VAAFCLTEPS SGSDAASIRT SAVPSPCGKY    240
YTLNGSKLWI SNGGLADIFT VFAKTPVTDP ATGAVKEKIT AFVVERGFGG ITHGPPEKKM    300
GIKASNTAEV FFDGVRVPSE NVLGEVGSGF KVAMHILNNG RFGMAAALAG TMRGIIAKAV    360
DHATNRTQFG EKIHNFGLIQ EKLARMVMLQ YVTESMAYMV SANMDQGATD FQIEAAISKI    420
FGSEAAWKVT DECIQIMGGM GFMKEPGVER VLRDLRIFRI FEGTNDILRL FVALQGCMDK    480
GKELSGLGSA LKNPFGNAGL LLGEAGKQLR RRAGLGSGLS LSGLVHPELS RSGELAVRAL    540
EQFATVVEAK LIKHKKGIVN EQFLLQRLAD GAIDLYAMVV VLSRASRSLS EGHPTAQHEK    600
MLCDTWCIEA AARIREGMAA LQSDPWQQEL YRNFKSISKA LVERGGVVTS NPLGF         655

| SEQ ID NO: 40 | moltype = AA  length = 633 |
|---|---|
| FEATURE | Location/Qualifiers |
| source | 1..633 |
| | mol_type = protein |
| | organism = Homo sapiens |

SEQUENCE: 40
MQAARMAASL GRQLLRLGGG SSRLTALLGQ PRPGPARRPY AGGAAQESKS FAVGMFKGQL     60
TTDQVFPYPS VLNEEQTQFL KELVEPVSRF FEEVNDPAKN DALEMVEETT WQGLKELGAF    120

```
GLQVPSELGG VGLCNTQYAR LVEIVGMHDL GVGITLGAHQ SIGFKGILLF GTKAQKEKYL    180
PKLASGETVA AFCLTEPSSG SDAASIRTSA VPSPCGKYYT LNGSKLWISN GGLADIFTVF    240
AKTPVTDPAT GAVKEKITAF VVERGFGGIT HGPPEKKMGI KASNTAEVFF DGVRVPSENV    300
LGEVGSGFKV AMHILNNGRF GMAAALAGTM RGIIAKAVDH ATNRTQFGEK IHNFGLIQEK    360
LARMVMLQYV TESMAYMVSA NMDQGATDFQ IEAAISKIFG SEAAWKVTDE CIQIMGGMGF    420
MKEPGVERVL RDLRIFRIFE GTNDILRLFV ALQGCMDKGK ELSGLGSALK NPFGNAGLLL    480
GEAGKQLRRR AGLGSGLSLS GLVHPELSRS GELAVRALEQ FATVVEAKLI KHKKGIVNEQ    540
FLLQRLADGA IDLYAMVVVL SRASRSLSEG HPTAQHEKML CDTWCIEAAA RIREGMAALQ    600
SDPWQQELYR NFKSISKALV ERGGVVTSNP LGF                                 633

SEQ ID NO: 41              moltype = AA   length = 678
FEATURE                    Location/Qualifiers
source                     1..678
                           mol_type = protein
                           organism = Homo sapiens
SEQUENCE: 41
MLGGLAAAAG TRIMGKEIEA EAQRPLRQTW RPGQPPAMTA KTMSSRLTAL LGQPRPGPAR     60
RPYAGGAAQL ALDKSDSHPS DALTRKKPAK AESKSFAVGM FKGQLTTDQV FPYPSVLNEE    120
QTQFLKELVE PVSRFFEEVN DPAKNDALEM VEETTWQGLK ELGAFGLQVP SELGGVGLCN    180
TQYARLVEIV GMHDLGVGIT LGAHQSIGFK GILLFGTKAQ KEKYLPKLAS GETVAAFCLT    240
EPSSGSDAAS IRTSAVPSPC GKYYTLNGSK LWISNGGLAD IFTVFAKTPV TDPATGAVKE    300
KITAFVVERG FGGITHGPPE KKMGIKASNT AEVFFDGVRV PSENVLGEVG SGFKVAMHIL    360
NNGRFGMAAA LAGTMRGIIA KAVDHATNRT QFGEKIHNFG LIQEKLARMV MLQYVTESMA    420
YMVSANMDQG ATDFQIEAAI SKIFGSEAAW KVTDECIQIM GGMGFMKEPG VERVLRDLRI    480
FRIFEGTNDI LRLFVALQGC MDKGKELSGL GSALKNPFGN AGLLLGEAGK QLRRRAGLGS    540
GLSLSGLVHP ELSRSGELAV RALEQFATVV EAKLIKHKKG IVNEQFLLQR LADGAIDLYA    600
MVVVLSRASR SLSEGHPTAQ HEKMLCDTWC IEAAARIREG MAALQSDPWQ QELYRNFKSI    660
SKALVERGGV VTSNPLGF                                                  678

SEQ ID NO: 42              moltype = AA   length = 655
FEATURE                    Location/Qualifiers
source                     1..655
                           mol_type = protein
                           organism = Mus sp.
SEQUENCE: 42
MQSARMTPSV GRQLLRLGAR SSRSTTVLQG QPRPISAQRL YAREATQAVL DKPETLSSDA     60
STREKPARAE SKSFAVGMFK GQLTIDQVFP YPSVLSEEQA QFLKELVGPV ARFFEEVNDP    120
AKNDALEKVE DDTLQGLKEL GAFGLQVPSE LGGLGLSNTQ YARLAEIVGM HDLGVSVTLG    180
AHQSIGFKGI LLYGTKAQRE KYLPRVASGG ALAAFCLTEP SSGSDVASIR SSAIPSPCGK    240
YYTLNGSKIW ISNGGLADIF TVFAKTPIKD AATGAVKEKI TAPVVERSFG GVTHGLPEKK    300
MGIKASNTSE VYFDGVKVPS ENVLGEVGDG FKVAVNILNN GRFGMAATLA GTMKSLIAKA    360
VDHATNRTQF GDKIHNFGVI QEKLARMAIL QYVTESMAYM LSANMDQGFK DFQIEAAISK    420
IFCSEAAWKV ADECIQIMGG MGFMKEPGVE RVLRDIRIFR IFEGANDILR LFVALQGCMD    480
KGKELTGLGN ALKNPFGNVG LLMGEAGKQL RRRTGIGSGL SLSGIVHPEL SRSGELAVQA    540
LDQFATVVEA KLVKHKKGIV NEQFLLQRLA DGAIDLYAMV VVLSRASRSL SEGYPTAQHE    600
KMLCDSWCIE AATRIRENMA SLQSSPQHQE LFRNFRSISK AMVENGGLVT GNPLG         655

SEQ ID NO: 43              moltype = AA   length = 22
FEATURE                    Location/Qualifiers
source                     1..22
                           mol_type = protein
                           organism = synthetic construct
VARIANT                    19
                           note = Any non-natural amino acid
VARIANT                    15
                           note = Any non-natural amino acid
SEQUENCE: 43
AKALETLRRV GDGVXRNHXT AF                                              22

SEQ ID NO: 44              moltype = AA   length = 22
FEATURE                    Location/Qualifiers
source                     1..22
                           mol_type = protein
                           organism = synthetic construct
VARIANT                    15
                           note = Any non-natural amino acid
VARIANT                    19
                           note = Any non-natural amino acid
SEQUENCE: 44
RAALETLRRV GDGVXRNHXT AF                                              22

SEQ ID NO: 45              moltype = AA   length = 22
FEATURE                    Location/Qualifiers
source                     1..22
                           mol_type = protein
                           organism = synthetic construct
VARIANT                    15
                           note = Any non-natural amino acid
VARIANT                    19
```

```
                        note = Any non-natural amino acid
SEQUENCE: 45
RKAAETLRRV GDGVXRNHXT AF                                                22

SEQ ID NO: 46           moltype = AA   length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 46
RKALATLRRV GDGVXRNHXT AF                                                22

SEQ ID NO: 47           moltype = AA   length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 47
RKALEALRRV GDGVXRNHXT AF                                                22

SEQ ID NO: 48           moltype = AA   length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 48
RKALETARRV GDGVXRNHXT AF                                                22

SEQ ID NO: 49           moltype = AA   length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 49
RKALETLARV GDGVXRNHXT AF                                                22

SEQ ID NO: 50           moltype = AA   length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 50
RKALETLRAV GDGVXRNHXT AF                                                22

SEQ ID NO: 51           moltype = AA   length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 51
RKALETLRRA GDGVXRNHXT AF                                                22

SEQ ID NO: 52           moltype = AA   length = 22
FEATURE                 Location/Qualifiers
source                  1..22
```

```
                        mol_type = protein
                        organism = synthetic construct
VARIANT                 15
                        note = Any non-natural amino acid
VARIANT                 19
                        note = Any non-natural amino acid
SEQUENCE: 52
RKALETLRRV ADGVXRNHXT AF                                                22

SEQ ID NO: 53           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 53
RKALETLRRV GAGVXRNHXT AF                                                22

SEQ ID NO: 54           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 54
RKALETLRRV GDAVXRNHXT AF                                                22

SEQ ID NO: 55           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 55
RKALETLRRV GDGAXRNHXT AF                                                22

SEQ ID NO: 56           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 56
RKALETLRRV GDGVXANHXT AF                                                22

SEQ ID NO: 57           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 57
RKALETLRRV GDGVXRAHXT AF                                                22

SEQ ID NO: 58           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 58
```

```
RKALETLRRV GDGVXRNAXT AF                                          22

SEQ ID NO: 59           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 59
RKALETLRRV GDGVXRNHXA AF                                          22

SEQ ID NO: 60           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SEQUENCE: 60
RKALETLRRV GDGVXRNHXT AA                                          22

SEQ ID NO: 61           moltype = AA  length = 20
FEATURE                 Location/Qualifiers
source                  1..20
                        mol_type = protein
                        organism = synthetic construct
VARIANT                 13
                        note = Any non-natural amino acid
VARIANT                 17
                        note = Any non-natural amino acid
SITE                    1
                        note = benzophenone moiety
SEQUENCE: 61
XLETLRRVGD GVXRNHXTAF                                             20

SEQ ID NO: 62           moltype = AA  length = 20
FEATURE                 Location/Qualifiers
source                  1..20
                        mol_type = protein
                        organism = synthetic construct
VARIANT                 13
                        note = Any non-natural amino acid
VARIANT                 17
                        note = Any non-natural amino acid
SITE                    3
                        note = benzophenone moiety
SEQUENCE: 62
ALXTLRRVGD GVXRNHXTAF                                             20

SEQ ID NO: 63           moltype = AA  length = 22
FEATURE                 Location/Qualifiers
source                  1..22
                        mol_type = protein
                        organism = synthetic construct
VARIANT                 15
                        note = Any non-natural amino acid
VARIANT                 19
                        note = Any non-natural amino acid
SITE                    5
                        note = benzophenone moiety
SEQUENCE: 63
RKALXTLRRV GDGVXRNHXT AF                                          22

SEQ ID NO: 64           moltype = AA  length = 14
FEATURE                 Location/Qualifiers
VARIANT                 14
                        note = Ala or Val
source                  1..14
                        mol_type = protein
                        organism = synthetic construct
SEQUENCE: 64
RKALETLRRV GDGX                                                   14

SEQ ID NO: 65           moltype = AA  length = 11
```

```
FEATURE                 Location/Qualifiers
source                  1..11
                        mol_type = protein
                        organism = unidentified
SEQUENCE: 65
LETLRRVGDG V                                                                    11

SEQ ID NO: 66           moltype = AA  length = 14
FEATURE                 Location/Qualifiers
source                  1..14
                        mol_type = protein
                        organism = unidentified
SEQUENCE: 66
LETLRRVGDG VQRN                                                                 14

SEQ ID NO: 67           moltype = AA  length = 17
FEATURE                 Location/Qualifiers
source                  1..17
                        mol_type = protein
                        organism = unidentified
SEQUENCE: 67
ALETLRRVGD GVQRNHE                                                              17

SEQ ID NO: 68           moltype = AA  length = 22
FEATURE                 Location/Qualifiers
source                  1..22
                        mol_type = protein
                        organism = Homo sapiens
SEQUENCE: 68
RKALETLRRV GDGVQRNHET AF                                                        22

SEQ ID NO: 69           moltype = AA  length = 10
FEATURE                 Location/Qualifiers
source                  1..10
                        mol_type = protein
                        organism = synthetic construct
SEQUENCE: 69
HHHHHHHHHH                                                                      10

SEQ ID NO: 70           moltype = AA  length = 4
FEATURE                 Location/Qualifiers
source                  1..4
                        mol_type = protein
                        organism = synthetic construct
SEQUENCE: 70
RKAL                                                                            4
```

What is claimed is:

1. An MCL-1 Stabilized Alpha-Helix of BCL-2 domain (SAHB) peptide comprising an amino acid sequence that is identical to the amino acid sequence set forth in any one of SEQ ID NOs: 53, 55, 44, 46, 47, 51, 52, 54, and 59, except for one amino acid substitution, wherein the MCL-1 SAHB peptide binds to VLCAD and/or MCL-1,
   wherein positions 12, 15, and 19 of SEQ ID NO:53 are not substituted,
   wherein positions 14, 15, and 19 of SEQ ID NO:55 are not substituted,
   wherein positions 2, 15, and 19 of SEQ ID NO:44 are not substituted,
   wherein positions 5, 15, and 19 of SEQ ID NO:46 are not substituted,
   wherein positions 6, 15, and 19 of SEQ ID NO:47 are not substituted,
   wherein positions 10, 15, and 19 of SEQ TD NO:51 are not substituted,
   wherein positions 11, 15, and 19 of SEQ ID NO:52 are not substituted,
   wherein positions 13, 15, and 19 of SEQ ID NO:54 are not substituted,
   wherein positions 15, 19, and 20 of SEQ ID NO:59 are not substituted;
   wherein the amino acid at each of positions 15 and 19 of any one of SEQ ID NOs: 53, 55, 44, 46, 47, 51, 52, 54, and 59 is a non-natural stapling amino acid, and wherein position 15 of any one of SEQ ID NOs: 53, 55, 44, 46, 47, 51, 52, 54, and 59 is cross-linked to position 19 of any one of SEQ ID NOs: 53, 55, 44, 46, 47, 51, 52, 54, and 59, respectively.

2. An MCL-1 Stabilized Alpha-Helix of BCL-2 domain (SAHB) peptide comprising the amino acid sequence set forth in any one of SEQ ID NOs: 53, 55, 44, 46, 47, 51, 52, 54, or 59.

3. A photoreactive SAHB (pSAHB) comprising the MCL-1 SAHB peptide of claim 1.

4. A photoreactive SAHB (pSAHB) comprising (a) an amino acid sequence set forth in any one of SEQ ID NOs:61-63; or (b) an amino acid sequence set forth in any one of SEQ ID NOs: 5-11, 15, 20-22, 24, 26, 28, 30, and 32.

5. The pSAHB of claim 4, wherein the pSAHB comprises the amino acid sequence set forth in any one of SEQ ID NOs:61-63.

6. The pSAHB of claim 3, which is biotinylated, comprises a benzophenone moiety, or a combination thereof.

7. The pSAHB of claim 4, which is biotinylated, comprises a benzophenone moiety, or a combination thereof.

8. A pharmaceutical composition comprising the pSAHB of claim 3 and a pharmaceutically acceptable carrier.

9. The MCL-1 SAHB peptide of claim 1, wherein the one amino acid substitution is not at position 1, 4, 7, 8, 9, 18, or 22 in any one of SEQ ID NOs: 53, 55, 44, 46, 47, 51, 52, 54, and 59.

10. The MCL-1 SAHB peptide of claim 1, wherein the one amino acid substitution is with a benzophenone moiety.

11. A pharmaceutical composition comprising the MCL-1 SAHB peptide of claim 1, and a pharmaceutically acceptable carrier.

12. An MCL-1 Stabilized Alpha-Helix of BCL-2 domain (SAHB) peptide comprising the amino acid sequence set forth in any one of SEQ ID NOs: 5-11, 15, 20-22, 24, 26, 28, 30, and 32.

13. The pSAHB of claim 4, wherein the pSAHB comprises the amino acid sequence set forth in any one of SEQ ID NOs: 5-11, 15, 20-22, 24, 26, 28, 30, and 32.

14. The MCL-1 SAHB peptide of claim 2, wherein the MCL-1 SAHB peptide comprises the amino acid sequence set forth in SEQ ID NO: 53, wherein the amino acid at each of positions 15 and 19 of SEQ ID NO: 53 is a non-natural stapling amino acid, and wherein position 15 of SEQ ID NO: 53 is cross-linked to position 19 of SEQ ID NO: 53.

15. The MCL-1 SAHB peptide of claim 2, wherein the MCL-1 SAHB peptide comprises the amino acid sequence set forth in SEQ ID NO: 55, wherein the amino acid at each of positions 15 and 19 of SEQ ID NO: 55 is a non-natural stapling amino acid, and wherein position 15 of SEQ ID NO: 55 is cross-linked to position 19 of SEQ ID NO: 53.

16. A pharmaceutical composition comprising the MCL-1 SAHB peptide of claim 14, and a pharmaceutically acceptable carrier.

17. A pharmaceutical composition comprising the MCL-1 SAHB peptide of claim 15, and a pharmaceutically acceptable carrier.

18. The MCL-1 SAHB peptide of claim 2, the amino acid at each of positions 15 and 19 of any one of SEQ ID NOs: 53, 55, 44, 46, 47, 51, 52, 54, and 59 is a non-natural stapling amino acid, and wherein position 15 of any one of SEQ ID NOs: 53, 55, 44, 46, 47, 51, 52, 54, and 59 is cross-linked to position 19 of any one of SEQ ID NOs: 53, 55, 44, 46, 47, 51, 52, 54, and 59, respectively.

19. The MCL-1 SAHB peptide of claim 18, wherein the non-natural stapling amino acid at each of positions 15 and 19 of any one of SEQ ID NOs: 53, 55, 44, 46, 47, 51, 52, 54, and 59 is (S)-2-(4-pentenyl)Ala-OH.

20. The MCL-1 SAHB peptide of claim 2, wherein the MCL-1 SAHB peptide comprises the amino acid sequence set forth in SEQ ID NO: 53, wherein the amino acid at each of positions 15 and 19 of SEQ ID NO: 53 is (S)-2-(4-pentenyl)Ala-OH, and wherein position 15 of SEQ ID NO: 53 is cross-linked to position 19 of SEQ ID NO: 53.

21. The MCL-1 SAHB peptide of claim 2, wherein the MCL-1 SAHB peptide comprises the amino acid sequence set forth in SEQ ID NO: 55, wherein the amino acid at each of positions 15 and 19 of SEQ ID NO: 55 is (S)-2-(4-pentenyl)Ala-OH, and wherein position 15 of SEQ ID NO: 55 is cross-linked to position 19 of SEQ ID NO: 55.

22. The MCL-1 SAHB peptide of claim 2, wherein the MCL-1 SAHB peptide consists of the amino acid sequence of any one of SEQ ID NOs: 53, 55, 44, 46, 47, 51, 52, 54, and 59, wherein the amino acid at each of positions 15 and 19 of any one of SEQ ID NOs: 53, 55, 44, 46, 47, 51, 52, 54, and 59 is (S)-2-(4-pentenyl)Ala-OH, and wherein position 15 is cross-linked to position 19.

23. The MCL-1 SAHB peptide of claim 2, wherein the MCL-1 SAHB peptide consists of the amino acid sequence set forth in SEQ ID NO: 53, wherein the amino acid at each of positions 15 and 19 of SEQ ID NO: 53 is (S)-2-(4-pentenyl)Ala-OH, and wherein position 15 of SEQ ID NO: 53 is cross-linked to position 19 of SEQ ID NO: 53.

24. The MCL-1 SAHB peptide of claim 2, wherein the MCL-1 SAHB peptide consists of the amino acid sequence set forth in SEQ ID NO: 55, wherein the amino acid at each of positions 15 and 19 of SEQ ID NO: 55 is (S)-2-(4-pentenyl)Ala-OH, and wherein position 15 of SEQ ID NO: 55 is cross-linked to position 19 of SEQ ID NO: 55.

25. A pharmaceutical composition comprising the MCL-1 SAHB peptide of claim 2, and a pharmaceutically acceptable carrier.

26. A pharmaceutical composition comprising the MCL-1 SAHB peptide of claim 12, and a pharmaceutically acceptable carrier.

27. A pharmaceutical composition comprising the MCL-1 SAHB peptide of claim 18, and a pharmaceutically acceptable carrier.

28. A pharmaceutical composition comprising the MCL-1 SAHB peptide of claim 19, and a pharmaceutically acceptable carrier.

* * * * *